(12) United States Patent
Hyde et al.

(10) Patent No.: US 10,080,823 B2
(45) Date of Patent: Sep. 25, 2018

(54) SUBSTRATES FOR NITRIC OXIDE RELEASING DEVICES

(75) Inventors: Roderick A. Hyde, Redmond, WA (US); Muriel Y. Ishikawa, Livermore, CA (US); Leif T. Stordal, Issaquah, WA (US); Lowell L. Wood, Jr., Bellevue, WA (US)

(73) Assignee: Gearbox LLC, Bellevue, WA (US)

( * ) Notice: Subject to any disclaimer, the term of this patent is extended or adjusted under 35 U.S.C. 154(b) by 903 days.

(21) Appl. No.: 12/927,610

(22) Filed: Nov. 17, 2010

(65) Prior Publication Data

US 2011/0166536 A1    Jul. 7, 2011

Related U.S. Application Data

(63) Continuation-in-part of application No. 12/008,708, filed on Jan. 11, 2008, now Pat. No. 7,846,400, and a continuation-in-part of application No. 11/981,743, filed on Oct. 30, 2007, now Pat. No. 8,642,093, and a continuation-in-part of application No. 11/998,864, filed on Nov. 30, 2007, now Pat. No. 8,221,690, and a continuation-in-part of application No. 12/005,045, filed on Dec. 21, 2007, now abandoned, and a continuation-in-part of application No. 12/005,065, filed on Dec. 21, 2007, now Pat. No. 7,862,598, and a continuation-in-part of application No. 12/005,132, filed on Dec. 21, 2007, now Pat. No. 7,897,399, and a continuation-in-part of application No. 12/005,136, filed on Dec. 21, 2007, now abandoned, and a continuation-in-part of application No. 12/005,170,
(Continued)

(51) Int. Cl.
*A61F 6/04* (2006.01)
*A61L 31/16* (2006.01)
*A61K 33/00* (2006.01)

(52) U.S. Cl.
CPC .............. *A61L 31/16* (2013.01); *A61K 33/00* (2013.01); *A61L 2300/114* (2013.01); *Y10T 29/49826* (2015.01)

(58) Field of Classification Search
CPC .......... G01N 1/00; G01N 23/00; G01N 27/00; G01N 27/02; G01N 27/125; G01N 27/129; A61F 6/04; A61F 6/043; A61L 31/16; A61L 2300/114; A61K 33/00; Y10T 29/49826
USPC ....... 422/98, 186, 186.3; 435/286.1; 436/55; 600/40, 377; 602/1, 40, 41; 604/23, 500; 607/88; 702/24
See application file for complete search history.

(56) References Cited

U.S. PATENT DOCUMENTS 3,918,967 A    11/1975    Krohn et al.
4,162,536 A    7/1979    Morley
(Continued)

FOREIGN PATENT DOCUMENTS

DE    20115123 U1    6/2001
EP    1 704 877 A1    9/2006
(Continued)

OTHER PUBLICATIONS

Walt et al.; "Biological Warfare"; Analytical Chemistry; Dec. 1, 2000; pp. 738 A-747 A.
(Continued)

*Primary Examiner* — Ophelia A Hawthorne

(57) ABSTRACT

The present disclosure relates to substrates associated with nitric oxide.

22 Claims, 23 Drawing Sheets

Related U.S. Application Data filed on Dec. 21, 2007, now Pat. No. 7,975,699, and a continuation-in-part of application No. 12/006,090, filed on Dec. 28, 2007, now abandoned, and a continuation-in-part of application No. 12/006,069, filed on Dec. 28, 2007, now abandoned, and a continuation-in-part of application No. 12/006,049, filed on Dec. 28, 2007, now abandoned, and a continuation-in-part of application No. 12/008,694, filed on Jan. 11, 2008, now Pat. No. 8,349,262.

(56) References Cited

U.S. PATENT DOCUMENTS

| | | | |
|---|---|---|---|
| 4,210,697 | A | 7/1980 | Adiletta |
| 4,248,214 | A | 2/1981 | Hannah et al. |
| 4,561,429 | A | 12/1985 | Sato et al. |
| 4,611,594 | A | 9/1986 | Grayhack et al. |
| 4,919,149 | A | 4/1990 | Stang |
| 5,109,871 | A | 5/1992 | Thornton |
| 5,262,165 | A | 11/1993 | Govil et al. |
| 5,279,294 | A | 1/1994 | Anderson et al. |
| 5,351,698 | A | 10/1994 | Wheeler et al. |
| 5,366,997 | A | 11/1994 | Keefer et al. |
| 5,374,710 | A | 12/1994 | Tsien et al. |
| 5,405,919 | A | 4/1995 | Keefer et al. |
| 5,495,961 | A | 3/1996 | Maestre |
| 5,530,263 | A | 6/1996 | DiVincenzo |
| 5,567,302 | A | 10/1996 | Song et al. |
| 5,571,152 | A | 11/1996 | Chen et al. |
| 5,580,433 | A | 12/1996 | Baker et al. |
| 5,582,170 | A | 12/1996 | Soller |
| 5,665,077 | A | 9/1997 | Rosen et al. |
| 5,676,963 | A | 10/1997 | Keefer et al. |
| 5,683,668 | A | 11/1997 | Hrabie et al. |
| 5,690,777 | A | 11/1997 | Kuethe et al. |
| 5,692,520 | A | 12/1997 | Lavoisier |
| 5,736,152 | A | 4/1998 | Dunn |
| 5,741,815 | A | 4/1998 | Lai |
| 5,765,558 | A | 6/1998 | Psaros et al. |
| 5,814,666 | A | 9/1998 | Green et al. |
| 5,858,799 | A | 1/1999 | Yee et al. |
| 5,900,433 | A | 5/1999 | Igo et al. |
| 5,910,316 | A | 6/1999 | Keefer et al. |
| 5,943,160 | A | 8/1999 | Downing |
| 5,956,172 | A | 9/1999 | Downing |
| 5,958,427 | A | 9/1999 | Salzman et al. |
| 5,980,705 | A | 11/1999 | Allen et al. |
| 5,994,444 | A | 11/1999 | Trescony et al. |
| 6,000,398 | A | 12/1999 | Alla et al. |
| 6,037,346 | A | 3/2000 | Doherty, Jr. et al. |
| 6,080,110 | A | 6/2000 | Thorgersen |
| 6,100,096 | A | 8/2000 | Bollinger et al. |
| 6,103,765 | A | 8/2000 | Neal |
| 6,127,363 | A | 10/2000 | Doherty, Jr. et al. |
| 6,143,314 | A | 11/2000 | Chandrashekar et al. |
| 6,149,606 | A | 11/2000 | Alving et al. |
| 6,156,753 | A | 12/2000 | Doherty, Jr. et al. |
| 6,182,661 | B1 | 2/2001 | Solanki et al. |
| 6,190,704 | B1 | 2/2001 | Murrell |
| 6,223,747 | B1 | 5/2001 | Rudge et al. |
| 6,241,752 | B1 | 6/2001 | Sheinman et al. |
| 6,265,420 | B1 | 7/2001 | Lai |
| 6,280,604 | B1 | 8/2001 | Allen et al. |
| 6,287,601 | B1 | 9/2001 | Russell |
| 6,306,609 | B1 | 10/2001 | Lai |
| 6,308,708 | B2 | 10/2001 | Strauss et al. |
| 6,321,751 | B1 | 11/2001 | Strauss et al. |
| 6,327,074 | B1 | 12/2001 | Bass et al. |
| 6,341,607 | B1 | 1/2002 | Couvreur |
| 6,369,071 | B1 | 4/2002 | Haj-Yehia |
| 6,432,077 | B1 | 8/2002 | Stenzler |
| 6,436,470 | B1 | 8/2002 | Iacocca et al. |
| 6,440,498 | B2 | 8/2002 | Schaller |
| 6,443,978 | B1 | 9/2002 | Zharov |
| 6,451,337 | B1 * | 9/2002 | Smith et al. ............ 424/445 |
| 6,469,051 | B2 | 10/2002 | Nagano et al. |
| 6,559,184 | B2 | 5/2003 | Neal |
| 6,612,306 | B1 | 9/2003 | Mault |
| 6,621,687 | B2 | 9/2003 | Lewis, Jr. et al. |
| 6,635,273 | B1 | 10/2003 | Loscalzo et al. |
| 6,635,415 | B1 | 10/2003 | Bollinger et al. |
| 6,636,652 | B1 | 10/2003 | Kopelman et al. |
| 6,639,007 | B2 | 10/2003 | Plamthottam |
| 6,651,667 | B2 | 11/2003 | Osterberg |
| 6,673,338 | B1 | 1/2004 | Arnold et al. |
| 6,673,871 | B2 | 1/2004 | Warneke et al. |
| 6,682,863 | B2 | 1/2004 | Rivers et al. |
| 6,696,072 | B1 | 2/2004 | Podolski |
| 6,706,274 | B2 | 3/2004 | Herrmann et al. |
| 6,743,249 | B1 | 6/2004 | Alden |
| 6,747,062 | B2 | 6/2004 | Murrell |
| 6,773,714 | B2 | 8/2004 | Dunn et al. |
| 6,812,500 | B2 | 11/2004 | Reeh et al. |
| 6,818,356 | B1 | 11/2004 | Bates |
| 6,840,244 | B2 | 1/2005 | Kemp |
| 6,841,166 | B1 | 1/2005 | Zhang et al. |
| 6,900,891 | B2 | 5/2005 | Kopelman et al. |
| 6,943,166 | B1 | 9/2005 | Pullman et al. |
| 6,969,507 | B2 | 11/2005 | Weisskoff et al. |
| 6,983,751 | B2 | 1/2006 | Osterberg |
| 6,994,934 | B2 | 2/2006 | Stanish et al. |
| 7,052,711 | B2 | 5/2006 | West et al. |
| 7,088,040 | B1 | 8/2006 | Ducharme et al. |
| 7,105,502 | B2 | 9/2006 | Arnold et al. |
| 7,105,607 | B2 | 9/2006 | Chen |
| 7,122,046 | B2 | 10/2006 | Augustine et al. |
| 7,122,529 | B2 | 10/2006 | Ruane et al. |
| 7,144,655 | B2 | 12/2006 | Jenson et al. |
| 7,181,174 | B2 | 2/2007 | Fitzgibbon et al. |
| 7,181,261 | B2 | 2/2007 | Silver et al. |
| 7,183,001 | B1 | 2/2007 | Ederle et al. |
| 7,189,471 | B2 | 3/2007 | Jankowksi et al. |
| 7,194,801 | B2 | 3/2007 | Jenson et al. |
| 7,206,605 | B2 | 4/2007 | Hattori |
| 7,210,817 | B2 | 5/2007 | Lee et al. |
| 7,215,687 | B2 | 5/2007 | Kawai et al. |
| 7,215,887 | B2 | 5/2007 | Ternullo et al. |
| 7,217,882 | B2 | 5/2007 | Walukiewicz et al. |
| 7,218,900 | B2 | 5/2007 | Suzuki |
| 7,220,258 | B2 | 5/2007 | Myhr |
| 7,227,956 | B1 | 6/2007 | Onishi |
| 7,235,189 | B2 | 6/2007 | Höhn et al. |
| 7,235,361 | B2 | 6/2007 | Bawendi et al. |
| 7,235,505 | B2 | 6/2007 | Gromelski et al. |
| 7,236,595 | B1 | 6/2007 | Bean et al. |
| 7,238,628 | B2 | 7/2007 | Demaray et al. |
| 7,245,894 | B2 | 7/2007 | Sekiguchi et al. |
| RE39,785 | E | 8/2007 | Fuse |
| 7,252,677 | B2 | 8/2007 | Burwell et al. |
| 7,253,953 | B2 | 8/2007 | Browning |
| 7,254,160 | B2 | 8/2007 | Kawamoto et al. |
| 7,256,923 | B2 | 8/2007 | Liu et al. |
| 7,257,327 | B2 | 8/2007 | Small |
| 7,260,155 | B2 | 8/2007 | Stonick et al. |
| 7,260,402 | B1 | 8/2007 | Ahmed |
| 7,260,764 | B2 | 8/2007 | Chen |
| 7,260,768 | B1 | 8/2007 | Matsumoto et al. |
| 7,261,693 | B2 | 8/2007 | Wilcox et al. |
| 7,264,602 | B1 | 9/2007 | Longsworth |
| 7,273,567 | B1 | 9/2007 | Wellinghoff et al. |
| 7,280,811 | B2 | 10/2007 | Sugiyama et al. |
| 7,283,710 | B2 | 10/2007 | Sano et al. |
| 7,294,678 | B2 | 11/2007 | McGlothlin et al. |
| 7,294,779 | B2 | 11/2007 | Watabe et al. |
| 7,295,737 | B2 | 11/2007 | Moorjani et al. |
| 7,295,741 | B2 | 11/2007 | Sako et al. |
| 7,298,605 | B2 | 11/2007 | Itoh et al. |
| 7,298,977 | B2 | 11/2007 | Ohsawa et al. |
| 7,301,751 | B2 | 11/2007 | Lee et al. |
| 7,301,754 | B1 | 11/2007 | Knowles |
| 7,303,333 | B2 | 12/2007 | Yu |
| 7,418,399 | B2 | 8/2008 | Schaeffer et al. |
| 7,449,595 | B2 | 11/2008 | Garvey et al. |

(56) References Cited

U.S. PATENT DOCUMENTS

| | | | |
|---|---|---|---|
| 7,582,623 B2 | 9/2009 | Mascharak | |
| 7,603,166 B2 | 10/2009 | Casscells, III et al. | |
| 7,829,553 B2 | 11/2010 | Arnold et al. | |
| 7,899,539 B2 | 3/2011 | Whitehurst et al. | |
| 8,241,650 B2* | 8/2012 | Peters | 424/402 |
| 2001/0007080 A1 | 7/2001 | Sheinman et al. | |
| 2002/0022046 A1 | 2/2002 | Tedeschi et al. | |
| 2002/0026937 A1 | 3/2002 | Mault | |
| 2002/0055702 A1 | 5/2002 | Atala et al. | |
| 2002/0068365 A1 | 6/2002 | Kuhrts | |
| 2002/0138051 A1 | 9/2002 | Hole et al. | |
| 2002/0155164 A1 | 10/2002 | Figley et al. | |
| 2002/0165179 A1 | 11/2002 | Baker, Jr. | |
| 2002/0188323 A1 | 12/2002 | Penner et al. | |
| 2003/0009127 A1 | 1/2003 | Trescony et al. | |
| 2003/0039697 A1 | 2/2003 | Zhao et al. | |
| 2003/0073133 A1 | 4/2003 | Leyland-Jones | |
| 2003/0077243 A1 | 4/2003 | Fitzhugh et al. | |
| 2003/0088191 A1 | 5/2003 | Freeman et al. | |
| 2003/0093143 A1 | 5/2003 | Zhao et al. | |
| 2003/0165578 A1 | 9/2003 | Murrell | |
| 2003/0203915 A1 | 10/2003 | Fang et al. | |
| 2004/0009238 A1 | 1/2004 | Miller et al. | |
| 2004/0013747 A1 | 1/2004 | Tucker et al. | |
| 2004/0072360 A1 | 4/2004 | Naaman et al. | |
| 2004/0081580 A1 | 4/2004 | Hole et al. | |
| 2004/0087831 A1 | 5/2004 | Michels et al. | |
| 2004/0158048 A1 | 8/2004 | Ruane et al. | |
| 2004/0166146 A1* | 8/2004 | Holloway | A61F 15/00 424/449 |
| 2004/0193218 A1 | 9/2004 | Butler | |
| 2004/0202692 A1 | 10/2004 | Shanley et al. | |
| 2004/0209869 A1 | 10/2004 | Landau et al. | |
| 2004/0247640 A1 | 12/2004 | Zhao et al. | |
| 2005/0053106 A1 | 3/2005 | Herron et al. | |
| 2005/0079148 A1 | 4/2005 | Fitzhugh et al. | |
| 2005/0136483 A1 | 6/2005 | Carlson | |
| 2005/0181026 A1 | 8/2005 | Davis et al. | |
| 2005/0197682 A1* | 9/2005 | Fox | A61N 5/0613 607/88 |
| 2005/0203069 A1 | 9/2005 | Arnold et al. | |
| 2005/0220838 A1 | 10/2005 | Zhao et al. | |
| 2005/0238704 A1 | 10/2005 | Zumbrunn et al. | |
| 2005/0249667 A1 | 11/2005 | Tuszynski et al. | |
| 2005/0267090 A1 | 12/2005 | Mascharak | |
| 2005/0286916 A1 | 12/2005 | Nakazato et al. | |
| 2006/0074282 A1 | 4/2006 | Ward et al. | |
| 2006/0134728 A1 | 6/2006 | MacDonald et al. | |
| 2006/0206171 A1 | 9/2006 | Gertner et al. | |
| 2006/0206173 A1 | 9/2006 | Gertner et al. | |
| 2006/0235493 A1 | 10/2006 | Dotson | |
| 2006/0275350 A1 | 12/2006 | Davis et al. | |
| 2006/0280307 A1 | 12/2006 | Ikushima et al. | |
| 2007/0021382 A1 | 1/2007 | Assaf et al. | |
| 2007/0053996 A1 | 3/2007 | Boyden et al. | |
| 2007/0054319 A1 | 3/2007 | Boyden et al. | |
| 2007/0059351 A1 | 3/2007 | Murrell et al. | |
| 2007/0065473 A1 | 3/2007 | Miller | |
| 2007/0088316 A1 | 4/2007 | Stenzler et al. | |
| 2007/0148117 A1 | 6/2007 | Davis et al. | |
| 2007/0166357 A1 | 7/2007 | Shaffer et al. | |
| 2007/0181444 A1 | 8/2007 | Bernstein et al. | |
| 2007/0190122 A1 | 8/2007 | Davis et al. | |
| 2007/0208395 A1* | 9/2007 | Leclerc | A61N 5/0616 607/86 |
| 2007/0233208 A1 | 10/2007 | Kurtz et al. | |
| 2007/0238918 A1 | 10/2007 | Squicciarini | |
| 2007/0274874 A1 | 11/2007 | Miller et al. | |
| 2007/0288071 A1* | 12/2007 | Rogers | A61N 5/062 607/88 |
| 2007/0298354 A1 | 12/2007 | Ding et al. | |
| 2008/0069863 A1 | 3/2008 | Peters | |
| 2008/0097282 A1* | 4/2008 | Hole | A61F 13/8405 604/23 |
| 2008/0220048 A1 | 9/2008 | Chen et al. | |
| 2008/0281383 A1 | 11/2008 | Butler | |
| 2008/0286321 A1 | 11/2008 | Reneker et al. | |
| 2008/0311163 A1 | 12/2008 | Peters | |
| 2009/0024063 A1 | 1/2009 | Kalvatanond | |
| 2009/0081279 A1 | 3/2009 | Jezek et al. | |
| 2009/0118710 A1 | 5/2009 | Kortzeborn | |
| 2009/0137988 A1 | 5/2009 | Kurtz | |
| 2009/0202617 A1 | 8/2009 | Ward et al. | |
| 2009/0204057 A1 | 8/2009 | Woo et al. | |
| 2009/0214618 A1 | 8/2009 | Schoenfisch et al. | |
| 2009/0214624 A1 | 8/2009 | Smith et al. | |
| 2010/0010593 A1* | 1/2010 | Wagennar Cacciola | A61N 5/0616 607/91 |
| 2010/0081144 A1 | 4/2010 | Holmes et al. | |
| 2010/0098733 A1 | 4/2010 | Stasko | |
| 2010/0152683 A1 | 6/2010 | Lindgren et al. | |
| 2010/0197802 A1 | 8/2010 | Jezek et al. | |
| 2011/0008815 A1 | 1/2011 | Stamler et al. | |
| 2011/0033437 A1 | 2/2011 | Smith et al. | |

FOREIGN PATENT DOCUMENTS

| | | |
|---|---|---|
| WO | WO 92/09962 | 6/1992 |
| WO | WO 96/08966 A1 | 3/1996 |
| WO | WO 00/53193 | 9/2000 |
| WO | WO 01/10344 A1 | 2/2001 |
| WO | WO 02/17898 A2 | 3/2002 |
| WO | WO 02/057738 A2 | 7/2002 |
| WO | WO 03/006427 A1 | 1/2003 |
| WO | WO 03/086282 A2 | 10/2003 |
| WO | WO 2005/070008 A2 | 8/2005 |
| WO | WO 2005/112954 A1 | 12/2005 |
| WO | WO 2006/084912 A1 | 8/2006 |
| WO | WO 2006/095193 A2 | 9/2006 |
| WO | WO 2006/100155 A1 | 9/2006 |
| WO | WO 2006/107122 A1 | 10/2006 |
| WO | WO 2006/108420 A1 | 10/2006 |
| WO | WO 2007/130702 A2 | 11/2007 |
| WO | WO 2008/046211 A1 | 4/2008 |
| WO | WO 2009/131931 A1 | 10/2009 |

OTHER PUBLICATIONS

U.S. Appl. No. 12/148,284, Hyde et al.
U.S. Appl. No. 12/148,283, Hyde et al.
Andrews, Karen L. et al.; "A Photosensitive Vascular Smooth Muscle Store of Nitric Oxide in Mouse Aorta: No Dependence on Expression of Endothelial Nitric Oxide Synthase"; British Journal of Pharmacology; 2003; pp. 932-940; vol. 138; Nature Publishing Group.
"A Method of Nitric Oxide Delivery for Healing and Organ Preservation"; University of Texas at Dallas; bearing a date of May 18, 2009; p. 1; located at: http://utdallas.technologypublisher.com/TechnologyProject.aspx?id=2302.
Birkeland et al.; "On the Oxidation of Atmospheric Nitrogen in Electric Arcs"; Nature; bearing a date of 1898; pp. 98-116; No. 1,506, vol. 58.
Bonaventura, Daniella et al.; "A Macrocyclic Nitrosyl Ruthenium Complex is a NO Donor that Induces Rat Aorta Relaxation"; Nitric Oxide; Mar. 2004; pp. 83-91 (p. 1); vol. 10, Issue 2; located at: http://www.sciencedirect.com; printed on Oct. 26, 2007 (Abstract Only).
Burrell, María A. et al.; "Detection of Nitric Oxide Synthase (NOS) in Somatostatin-Producing Cells of Human and Murine Stomach and Pancreas"; The Journal of Histochemistry and Cytochemistry; 1996; pp. 339-346; vol. 44, No. 4; The Histochemical Society, Inc.
Butler, P. et al.; "Cell Transplantation from Limb Allografts"; Plastic and Reconstructive Surgery; Bearing a date of Jul. 1998; pp. 161-168 (11 total pages); vol. 102, No. 1; American Society of Plastic Surgeons; located at: http://www.plasreconsurg.com; printed on Apr. 25, 2008.
Butler, A.R.; Nicholson, R.; *Life, Death and Nitric Oxide*; Bearing a date of Oct. 17, 2003; 1st edition; Royal Society of Chemistry; ISBN 978-0854046867 (Not Provided).

(56) References Cited

OTHER PUBLICATIONS

Chmura, Antonina et al.; "The Role of Photoinduced Electron Transfer Processes in Photodegradation of the $[Fe_4(\mu_3-S)_3(NO)_7]^-$ Cluster"; Nitric Oxide; Dec. 2006; pp. 370-379 (p. 1); vol. 15, Issue 4; located at: http://www.sciencedirect.com; printed on Oct. 26, 2007 (Abstract Only).
Chen, X; Gillis, CN; "Methylene Blue Enhanced Photorelaxation in Aorta, Pulmonary Artery and Corpus Cavernosum"; Biochem. Biophys. Res. Commun.; Jan. 29, 1993; pp. 559-563 (pp. 1-2); vol. 190, No. 2; located at: http://www.pubmed.gov; printed on Oct. 26, 2007 (Abstract Only).
De Lima, R.G. et al.; "Controlled Nitric Oxide Photo-Release From Nitro Ruthenium Complexes: The Vasodilator Response Produced by UV Light Irradiation"; Inorganica Chimica Acta; Bearing a date of 2005; pp. 2643-2650; vol. 358; Elsevier B.V.; located at: http://www.sciencedirect.com.
Dujić, Željko et al; "Aerobic Exercise Before Diving Reduces Venous Gas Bubble Formation in Humans"; J. Physiol.; 2004; pp. 637-642; vol. 555.3; The Physiological Society.
"Easy Life II"; Photon Technology International; pp. 1-3; located at: http://www.pti-nj.com/EasyLife/easylife.html; printed on Oct. 6, 2007.
Ferezin, Camila Z. et al; "The Complex $Trans$-$[RuCl([15]aneN_4)NO]^{2+}$ Induces Rat Aorta Relaxation by Ultraviolet Light Irradiation"; Nitric Oxide; Nov. 2005; pp. 170-175 (p. 1); vol. 13, Issue 3; located at: http://www.sciencedirect.com; printed on Oct. 26, 2007 (Abstract Only).
Flitney, FW et al.; "Iron-Sulphur Cluster Nitrosyls, a Novel Class of Nitric Oxide Generator: Mechanism of Vasodilator Action on Rat Isolated Tail Artery"; Br. J. Pharmacol.; Nov. 1992; pp. 842-848 (pp. 1-2); vol. 107, No. 3; located at: http://www.pubmed.gov; printed on Oct. 26, 2007 (Abstract Only).
Flitney, Frederick Werner; Megson, Ian L.; "Nitric Oxide and the Mechanism of Rat Vascular Smooth Muscle Photorelaxation"; J. Physiol.; 2003; pp. 819-828; vol. 550.3; The Physiological Society.
Flitney, FW et al.; "Vasodilator Responses of Rat Isolated Tail Artery Enhanced by Oxygen-Dependent, Photochemical Release of Nitric Oxide from Iron-Sulphur-Nitrosyls"; Br. J. Pharmacol.; Apr. 1996; pp. 1549-1557 (pp. 1-2); vol. 117, No. 7; located at: http://www.pubmed.gov; printed on Oct. 26, 2007 (Abstract Only).
Frank, S. et al.; "Nitric Oxide Triggers Enhanced Induction of Vascular Endothelial Growth Factor Expression in Cultured Keratinocytes (HaCaT) and During Cutaneous Wound Repair"; The FASEB Journal; Bearing a date of 1999; pp. 2002-2014; vol. 13.
Fukuhara, Kiyoshi et al.; "Photochemical Generation of Nitric Oxide from 6-Nitrobenzo[α]pyrene"; J. Am. Chem. Soc.; 2001; pp. 8662-8666 (p. 1); vol. 123, No. 36; located at: http://pubs.acs.org/cgi-bin/abstract.cgi/jacsat/2001/123/i36/abs/ja0109038.html; printed on Oct. 26, 2007 (Abstract Only).
Gaston, Benjamin; "Summary: Systemic Effects of Inhaled Nitric Oxide"; Proceedings of the American Thoracic Society; 2006; pp. 170-172; vol. 3.
Gau, Jen-Jr et al.; "A MEMS Based Amperometric Detector for *E. coli* Bacteria Using Self-Assembled Monolayers"; Biosensors & Bioelectronics; 2001; pp. 745-755; vol. 16; Elsevier Science B.V.
Ghaffari, A. et al.; "A Direct Nitric Oxide Gas Delivery System for Bacterial and Mammalian Cell Cultures"; Nitric Oxide; Bearing a date of 2005; pp. 129-140; vol. 12; Elsevier Inc.; located at: http://www.sciencedirect.com.
Ghaffari, A. et al.; "Efficacy of Gaseous Nitric Oxide in the Treatment of Skin and Soft Tissue Infections"; Wound Repair and Regeneration; Bearing a date of 2007; pp. 368-377; vol. 15; Wound Healing Society.
Ghaffari, A. et al.; "Potential Application of Gaseous Nitric Oxide as a Topical Antimicrobial Agent"; Nitric Oxide; Bearing a date of 2006; pp. 21-29; vol. 14; Elsevier Inc.; located at: http://www.sciencedirect.com.

Goldsmith, P.C. et al.; "Inhibitors of Nitric Oxide Synthase in Human Skin"; The Journal of Investigative Dermatology; Bearing a date of Jan. 1996; pp. 113-118; vol. 106, No. 1; The Society for Investigative Dermatology, Inc.
Govers, R.; Rabelink, T.J.; "Cellular Regulation of Endothelial Nitric Oxide Synthase"; Am. J. Physiol. Renal. Physiol.; Bearing a date of 2001; pp. F193-F206; vol. 280; The American Physiological Society; located at: http://www.ajprenal.org.
Graham-Rowe, Duncan; "Photonic Fabrics Take Shape"; Nature Photonics; Jan. 2007; pp. 6-7; vol. 1; Nature Publishing Group.
Guo, H.; "Two-and Three-Photon Upconversion of $LaOBr:Er^{3+}$"; Optical Materials; Bearing a date of 2007; pp. 1840-1843; vol. 29; Elsevier B.V.; located at: http://www.sciencedirect.com.
Hassett, D.J.; Imlay, J.A.; "Bactericidal Antibiotics and Oxidative Stress: A Radical Proposal"; ACS Chemical Biology; Bearing a date of 2007; pp. 708-710; vol. 2, No. 11; located at: http://www.acschemicalbiology.org.
Hardwick, J.B.J. et al.; "A Novel Method for the Delivery of Nitric Oxide Therapy to the Skin of Human Subjects Using a Semi-Permeable Membrane"; Clinical Science; 2001; pp. 395-400; vol. 100; The Biochemical Society and the Medical Research Society.
Hattenbach, Lars-Olof et al.; "Detection of Inducible Nitric Oxide Synthase and Vascular Endothelial Growth Factor in Choroidal Neovascular Membranes"; Ophthalmologica; 2002; pp. 209-214; vol. 216; S. Karger AG, Basel.
Hou, Yongchun et al.; "Nanomolar Scale Nitric Oxide Generation from Self-Assembled Monolayer Modified Gold Electrodes"; Chem. Commun.; 2000; pp. 1831-1832; The Royal Society of Chemistry.
Hrabie, Joseph A.; Keefer, Larry K.; "Chemistry of the Nitric Oxide-Releasing Diazeniumdiolate ("Nitrosohydroxylamine") Functional Group and Its Oxygen-Substituted Derivatives"; Chem. Rev.; 2002; pp. 1135-1154; vol. 102; American Chemical Society.
Ikeda, Osamu et al.; "Nitric Oxide Detection with Glassy Carbon Electrodes Coated with Charge-Different Polymer Films"; Sensors; Apr. 26, 2005; pp. 161-170; vol. 5; ISSN 1424-8220; MDPI.
"InNo-T Nitric Oxide Measurement System"; Warner Instruments; Bearing dates of 1998-2007; pp. 1-2; located at: http://www.warneronline.com/product_info.cfm?ID=220; printed on Oct. 24, 2007.
Keefer, Larry K.; "Nitric Oxide-Releasing Compounds: From Basic Research to Promising Drugs"; Chemtech; Aug. 1998; pp. 30-35 (pp. 1-8); vol. 28, No. 8; located at: http://pubs.acs.org/hotartcl/chemtech/98/aug/nitric.html; printed on Oct. 2, 2007; The American Chemical Society.
Khan, MA et al.; "The Effect of Superoxide Dismutase on Nitric Oxide-Mediated and Electrical Field-Stimulated Diabetic Rabbit Cavernosal Smooth Muscle Relaxation"; BJU Int.; Jan. 2001; pp. 98-103 (p. 1); vol. 87, No. 1; located at: http://www.pubmed.gov; printed on Sep. 27, 2007 (Abstract Only).
Kim, SC et al.; "Effects of Ultraviolet Light on the Tension of Isolated Human Cavernosal Smooth Muscle from Non-Diabetic and Diabetic Impotent Men"; Urol. Res.; 1997; pp. 149-152 (p. 1); vol. 25, No. 2; located at: http://www.pubmed.gov; printed on Sep. 27, 2007 (Abstract Only).
Kim, JH et al; "Mechanism of UV Light-Induced Photorelaxation in Isolated Rat Aorta"; J. Vet. Sci.; Dec. 2000; pp. 81-86 (p. 1); vol. 1, No. 2; located at: http://www.pubmed.gov; printed on Oct. 26, 2007 (Abstract Only).
Levine et al.; "A New, Highly Efficient Red-Emitting Cathodoluminescent Phosphor ($YVO_4$:Eu) for Color Television"; Applied Physics Letters; bearing a date of Sep. 15, 1964; pp. 1-3; vol. 5, No. 6.
Li, Chang Ming et al.; "Electrochemical Detection of Nitric Oxide on a SWCNT/RTIL Composite Gel Microelectrode"; Electroanalysis; 2006; pp. 713-718; vol. 18, No. 7; Wiley-VCH Verlag GmbH & Co. KGaA, Weinheim.
"Light-Emitting Diode (LED)"; Fiber Optics; Bearing a date of 2005; pp. 1-10; located at: http://www.fiber-optics.info/articles/LEDs.htm; printed on Oct. 6, 2007.
Lin, Hong-Yu et al.; "Side-Polished Multimode Fiber Biosensor Based on Surface Plasmon Resonance with Halogen Light"; Applied Optics; Feb. 10, 2007; pp. 800-806; vol. 46, No. 5; Optical Society of America.

(56) References Cited

OTHER PUBLICATIONS

Liu et al.; "Novel Delivery System for the Bioregulatory Agent Nitric Oxide"; Chemistry of Materials; bearing a date of 2009; pp. 5032-5041; vol. 21, No. 21; © 2009 American Chemical Society.
Matthews, EK et al.; "Photon Pharmacology of an Iron-Sulphur Cluster Nitrosyl Compound Acting on Smooth Muscle"; Br. J. Pharmacol.; Sep. 1994; pp. 87-94 (p. 1); vol. 113, No. 1; located at: http://www.pubmed.gov; printed on Oct. 26, 2007 (Abstract Only).
Mellor, J. W.; "Modern Inorganic Chemistry"; excerpt from Modern Inorganic Chemistry; bearing a date of 1912; pp. 1-19; Longmans, Greene, and Co.
Mendioroz, A. et al.; "Infrared to Visible and Ultraviolet Upconversion Processes in $Nd^{3+}$-Doped Potassium Lead Chloride Crystal"; Optical Materials; Sep. 2004; pp. 351-357 (p. 1); vol. 26, Issue 4; located at http://www.sciencedirect.com; printed on Oct. 29, 2007 (Abstract Only).
Miller, C.C. et al.; "Treatment of Chronic Nonhealing Leg Ulceration with Gaseous Nitric Oxide: A Case Study"; Journal of Cutaneous Medicine and Surgery; Bearing a date of Aug. 2004; pp. 233-238; vol. 8, No. 4.
Nablo, Brian J. et al.; "Inhibition of Implant-Associated Infections Via Nitric Oxide Release"; Biomaterials; Dec. 2005; pp. 6984-6990 (p. 1); vol. 26, Issue 34; located at: http://www.sciencedirect.com; printed on Oct. 26, 2007 (Abstract Only).
"Nanotechnology bandage speeds up healing"; Nanowerk News; Source: Akron Beacon Journal (Paula Schleis); bearing a date of Dec. 15, 2006; pp. 1-2; printed on Jul. 14, 2009; located at http://www.nanowerk.com/news/newsid=1156.php.
"Nanotechnology—the new Viagra?"; Nanowerk News; bearing a date of Apr. 26, 2009; p. 1; located at http://www.nanowerk.com/news/newsid=10273.php.
"Nitric oxide-releasing wrap for donor organs and cloth for therapeutic socks"; e! Science News; bearing a date of Jan. 6, 2010; pp. 1-2; located at http://esciencenews.com/articles/2010/01/06/nitric.oxide.releasing.wrap.donor.organs.and.cloth.therapeutic.socks; printed on Jan. 19, 2010.
"NO Electrodes"; WPI-Europe-Biosensing-NO Electrodes; Bearing a date of Nov. 29, 2007; pp. 1-5; World Precision Instruments; located at: http://www.wpi-europe.com/products/biosensing/noelectrodes.htm; printed on Nov. 29, 2007.
"OL 770-LED: High-Speed LED Measurement System"; Bearing a date of 2001; pp. 1-6; located at: http://www.optroniclabs.com; Optronic Laboratories, Inc.
Pacher, P. et al.; "Nitric Oxide and Peroxynitrite in Health and Disease"; Physiol. Rev.; Bearing a date of Jan. 2007; pp. 315-424; vol. 87; The American Physiological Society; located at: http://www.prv.org.
"Particulate Effects on Immunologic Function"; OST 1997AR; Bearing a date of 1997; pp. 1-2; located at: http://www.fda.gov/cdrh/ost/rpt97/OST1997AR9.HTML; printed on Oct. 16, 2007.
Patel, D.N. et al.; "Spectroscopic and Two-Photon Upconversion Studies of $Ho^{3+}$-Doped $Lu_3Al_5O_{12}$"; Optical Materials; Bearing a date of Jul. 1998; pp. 225-234; vol. 10; Elsevier Science B.V.
Peng, H. et al.; "Ultraviolet Light-Emitting Diodes Operating in the 340 nm Wavelength Range and Application to Time-Resolved Fluorescence Spectroscopy"; Applied Physics Letters; Aug. 23, 2004; pp. 1436-1438 (p. 1); vol. 85, Issue 8; located at: http://scitation.aip.org; printed on Oct. 26, 2007 (Abstract Only).
Pou, SJ et al.; "Biological Studies of a Nitroso Compound that Releases Nitric Oxide Upon Illumination"; Molecular Pharmacology; Oct. 1, 1994; pp. 709-715 (p. 1); Vo. 46, Issue 4; located at: http://molpharm.aspetjournals.org/cgi/content/abstract/46/7/709; printed on Oct. 26, 2007 (Abstract Only).
"Probes for Nitric Oxide (NO) Research"; EMD-Calbiochem: Nitric Oxide Probes; Bearing a date of 2007; pp. 1-2; Calbiochem, Novabiochem, & Novagen; located at: http://www.emdbiosciences.com/html/cbc/nitric_oxide_probes.htm; printed on Nov. 29, 2007.
Rapaport, A. et al.; "Review of the Properties of Up-Conversion Phosphors for New Emissive Displays"; Journal of Display Technology; Bearing a date of Mar. 2006; pp. 68-78; vol. 2, No. 1; IEEE.

Räthel, Thomas R. et al.; "Application of 4,5-Diaminofluorescein to Reliably Measure Nitric Oxide Released from Endothelial Cells In Vitro"; Biological Procedures Online; Jun. 2, 2003; pp. 136-142; vol. 5, No. 1.
Roméro-Graillet, C. et al.; "Nitric Oxide Produced by Ultraviolet-Irradiated Keratinocytes Stimulates Melanogenesis"; J. Clin. Invest.; Bearing a date of Feb. 1997; pp. 635-642; vol. 99, No. 4; The American Society of Clinical Investigation, Inc.
Rotta, J.C.G. et al.; "Nitric Oxide Release from the S-Nitrosothiol Zinc Phthalocyanine Complex by Flash Photolysis"; Brazilian Journal of Medical and Biological Research; 2003; pp. 587-594; vol. 36, No. 5; located at: http://www.scielo.br/pdf/bjmbr/v36n5/4604.pdf.
Seabra, A.B. et al.; "S-Nitrosoglutathione Incorporated in Poly(Ethylene Glycol) Matrix: Potential Use for Topical Nitric Oxide Delivery"; Nitric Oxide; Bearing a date of 2004; pp. 263-272; vol. 11; Elsevier Inc.; located at: http://www.sciencedirect.com.
Seo, K.K. et al.; "Synergistic Effects of Sildenafil on Relaxation of Rabbit and Rat Cavernosal Smooth Muscles when Combined with Various Vasoactive Agents"; BJU International; 2001; pp. 596-601; vol. 88.
Shabani, M. et al.; "Enhancement of Wound Repair with a Topically Applied Nitric Oxide-Releasing Polymer"; Wound Repair and Regeneration; Bearing dates of Jul.-Sep. 1996; pp. 353-362; vol. 4, No. 3; The Wound Healing Society.
Singh, Ravinder Jit et al.; "Photosensitized Decomposition of S-Nitrosothiols and 2-Methyl-2-Nitrosopropane Possible Use for Site-Directed Nitric Oxide Production"; FEBS Letters; 1995; pp. 47-51; vol. 360; Federation of European Biochemical Societies.
Smith, DJ et al.; "Nitric Oxide-Releasing Polymers Containing the [N(O)NO]-Group"; J. Med. Chem.; Mar. 1, 1996; pp. 1148-1156 (p. 1); vol. 39, No. 5; located at: http://www.pubmed.gov; printed on Oct. 26, 2007 (Abstract Only).
Sonoki, T. et al.; "Detection of Inducible Nitric Oxide Synthase (iNOS) mRNA by RT-PCR in ATL Patients and HTLV-1 Infected Cell Lines: Clinical Features and Apoptosis by NOS Inhibitor"; Leukemia; 1999; pp. 713-718; vol. 13; Stockton Press.
Sussman, C.; *Wound Care: A Collaborative Practice Manual*; Bearing a date of Jan. 2007; ISBN 0781774446 (Not Provided).
Suzuki, H.; Hewitt, C.W.; "Cell Transplantation from Limb Allografts: Discussion"; Plastic and Reconstructive Surgery; Bearing a date of Jul. 1998; pp. 169-170 (2 total pages); vol. 102, No. 1; American Society of Plastic Surgeons; located at: http://www.plasreconsurg.com; printed on May 2, 2008.
Tamir, S.; Tannenbaum, S.R.; "The Role of Nitric Oxide (NO) in the Carcinogenic Process"; Biochimica et Biophysica Acta; Bearing a date of 1996; pp. F31-F36; vol. 1288; Elsevier Science B.V.
"The Shadow Mask and Aperture Grill"; The PC Guide; bearing a date of Apr. 17, 2001; pp. 1-3; © Copyright 1997-2004 Charles M. Kozierok; printed Oct. 6, 2009; located at http://www.pcguide.com/ref/crt/crtMask-c.html.
Tu, H. et al.; "A Novel Electrochemical Microsensor for Nitric Oxide Based on Electropolymerized Film of o-Aminobenzaldehyde-Ethylene-Diamine Nickel"; Electroanalysis; Bearing a date of 1999; pp. 70-74; vol. 11, No. 1; Wiley-VCH.
Van Faassen, E.; Vanin, A. (Eds); *Radicals for Life: The Various Forms of Nitric Oxide*; Bearing a date of Mar. 2007; 442 pages; ISBN 978-0-444-52236-8; Elsevier (Not Provided).
Wadsworth, Roger et al.; "Physiologically Relevant Measurements of Nitric Oxide in Cardiovascular Research Using Electrochemical Microsensors"; Journal of Vascular Research; 2006; pp. 70-85; vol. 43; S. Karger AG, Basel.
Wang, Peng George et al.; "Nitric Oxide Donors: Chemical Activities and Biological Applications"; Chem. Rev.; 2002; pp. 1091-1134 (pp. 1-53); vol. 102, No. 4; American Chemical Society; located at: http://pubs.acs.org/cgi-bin/abstract.cgi/chreay/2002/102/i04/abs/cr0000401.html; printed on Oct. 6, 2007.
Wang, Tianlong et al.; "Inhaled Nitric Oxide in 2003: A Review of its Mechanisms of Action"; Canadian Journal of Anesthesia; 2003; pp. 839-846; vol. 50, No. 8.
Weller, R. et al.; "Antimicrobial Effect of Acidified Nitrite on Dermatophyte Fungi, *Candida* and Bacterial Skin Pathogens"; Journal of Applied Microbiology; Bearing a date of 2001; pp. 648-652; vol. 90; The Society for Applied Microbiology.

(56) References Cited

OTHER PUBLICATIONS

Weller, R. et al.; "Nitric Oxide is Generated on the Skin Surface by Reduction of Sweat Nitrate"; The Journal of Investigative Dermatology; Bearing a date of Sep. 1996; pp. 327-331; vol. 107, No. 3; The Society of Investigative Dermatology, Inc.

Williamson, David; "Study: Nitric Oxide-Releasing Materials Might Reduce Medical Implant Infections"; UNC News Services; Sep. 7, 2001; pp. 1-2; No. 416; located at: http://www.unc.edu/news/archives/sep01/schoen090701.htm; printed on Oct. 4, 2007.

Xie, Rong-Jun; "Highly Efficient White-Light-Emitting Diodes Fabricated with Short-Wavelength Yellow Oxynitride Phosphors"; Applied Physics Letters; Mar. 6, 2006; pp. 101104.1-101104.3 (pp. 1-2); vol. 88; located at: http://scitation.aip.org/; printed on Oct. 26, 2007 (Abstract Only).

Yamasaki, K. et al.; "Reversal of Impaired Wound Repair in iNOS-Deficient Mice by Topical Adenoviral-Mediated iNOS Gene Transfer"; J. Clin. Invest.; Bearing a date of Mar. 1998; pp. 967-971; vol. 101, No. 5; The American Society for Clinical Investigation, Inc.; located at: http://www.jci.org.

Zhelyaskov, V.R.; Godwin, D.W.; "Photolytic Generation of Nitric Oxide Through a Porous Glass Partitioning Membrane"; Nitric Oxide: Biology and Chemistry; Bearing a date of 1998; pp. 454-459; vol. 2, No. 6; Article No. NO980195; Academic Press.

U.S. Appl. No. 12/928,029, Hyde et al.
U.S. Appl. No. 12/928,028, Hyde et al.
U.S. Appl. No. 12/930,351, Hyde et al.

Jamal, Sophie A. et al.; "Effect of Nitroglycerin Ointment on Bone Density and Strength in Postmenopausal Women"; JAMA; bearing a date of Feb. 23, 2011; pp. 800-807; vol. 305, No. 8; American Medical Association.

Khosla, Sundeep; "Is Nitroglycerin a Novel and Inexpensive Treatment for Osteoporosis?"; JAMA; bearing a date of Feb. 23, 2011; pp. 826-827; vol. 305, No. 8; American Medical Association.

Mims, Christopher; "Erectile Dysfunction Treatment to Save Soldiers' Lives"; Technology Review; bearing a date of Feb. 22, 2011; 2 pages; MIT; located at http://www.technologyreview.com/blog/mimssbits/26427/?pl=A5.

Stubbington, Tommy; "New Condom Nears Approval"; The Wall Street Journal Online; bearing at date of Apr. 20, 2011; pp. 1-2; 13:18; Dow Jones & Company, Inc.

U.S. Appl. No. 13/452,502, Hyde et al.

Dictionary.com; "Patch"; printed on Jul. 20, 2012; pp. 1-8; located at: http://dictionary.reference.com/browse/patch.

"Using Skin Patch Medicines (Transdermal Patches)"; The Poison Post; Aug. 2012; pp. 1-3; The National Capital Poison Center.

* cited by examiner

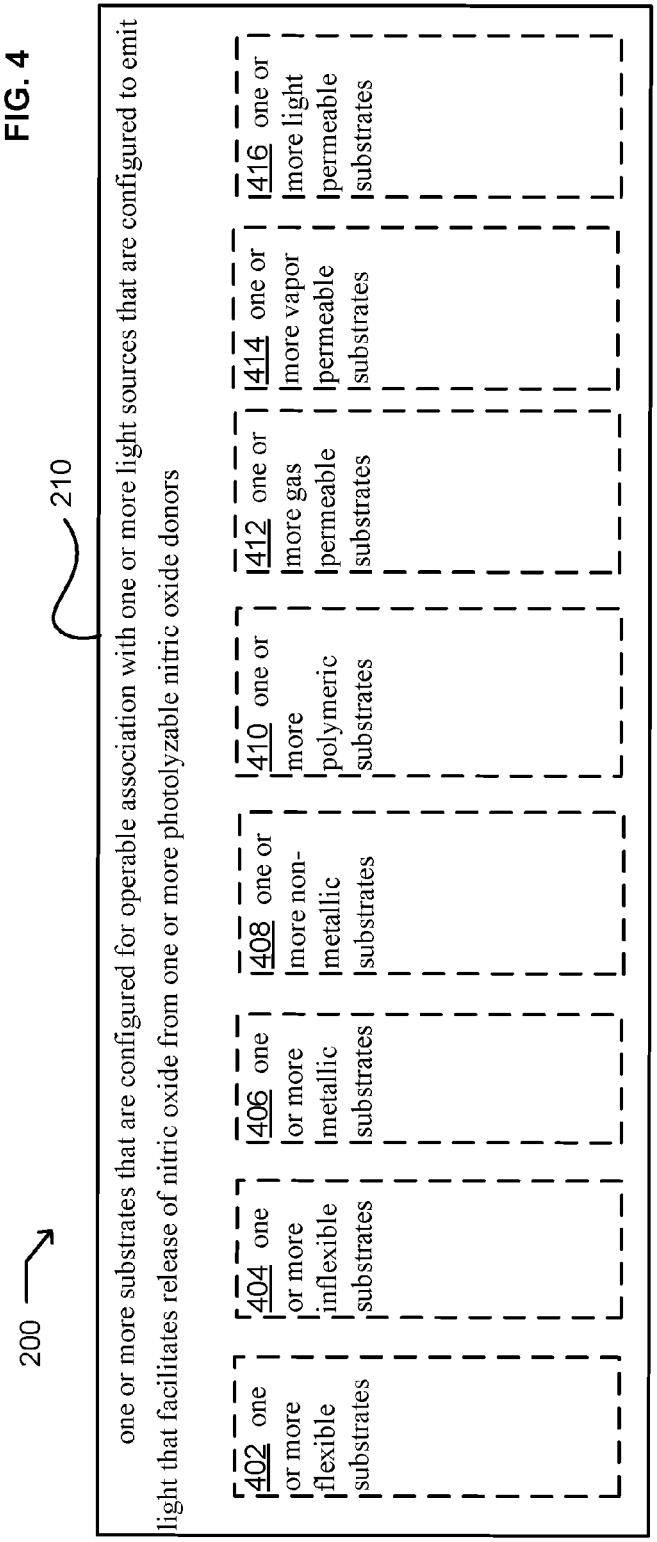

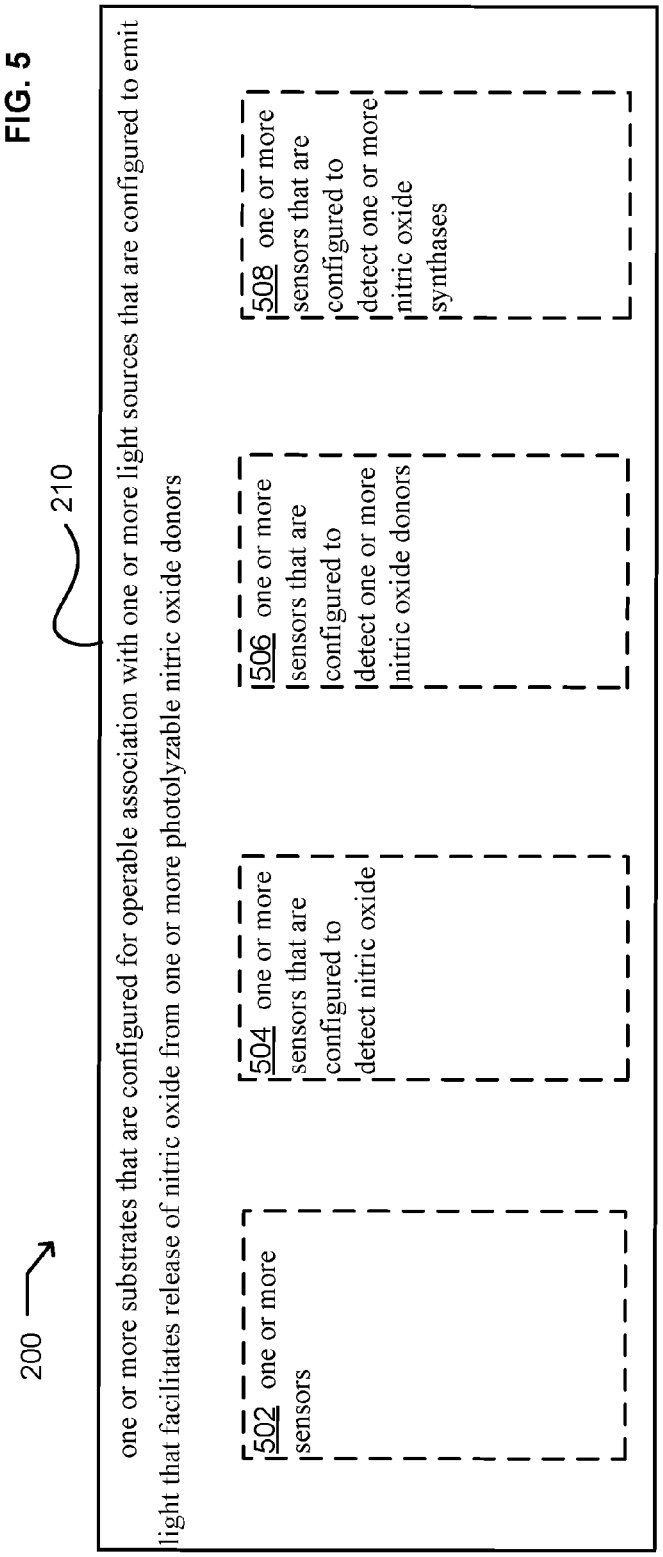

210 one or more substrates that are configured for operable association with one or more light sources that are configured to emit light that facilitates release of nitric oxide from one or more photolyzable nitric oxide donors

| 602 one or more substrates that include one or more connections configured for operable association with the one or more light sources | 604 one or more substrates that are configured to associate with one or more batteries | 606 one or more substrates that are configured to associate with one or more light emitting diodes | 608 one or more substrates that are configured to associate with one or more nitric oxide donors | 610 one or more substrates that include one or more operably coupled photolyzable nitric oxide donors | 612 one or more substrates that are configured as a sheet, a hood, a glove, a body wrap, a condom, a penile sleeve, a surgical drape, a mask, pants, a shirt, underwear, a sock, a mitten, a cap, a bag, a bed, a table, a chamber, or tape | 614 one or more status indicators | 616 one or more control units that are configured to control one or more remote light sources |

910 — one or more substrates that are configured for operable association with one or more light sources that are configured to emit light that facilitates release of nitric oxide from one or more photolyzable nitric oxide donors 930 — one or more light sources that are configured to emit light that facilitates release of nitric oxide from the one or more photolyzable nitric oxide donors

- 1102 one or more optical fibers
- 1104 one or more light emitting diodes
- 1106 one or more power supplies
- 1108 one or more power supplies that include one or more batteries
- 1110 one or more power supplies that include one or more solar cells
- 1112 one or more power supplies that include one or more capacitors
- 1114 one or more electromagnetic receivers
- 1116 one or more light sources that are coated with at least one of the one or more photolyzable nitric oxide donors

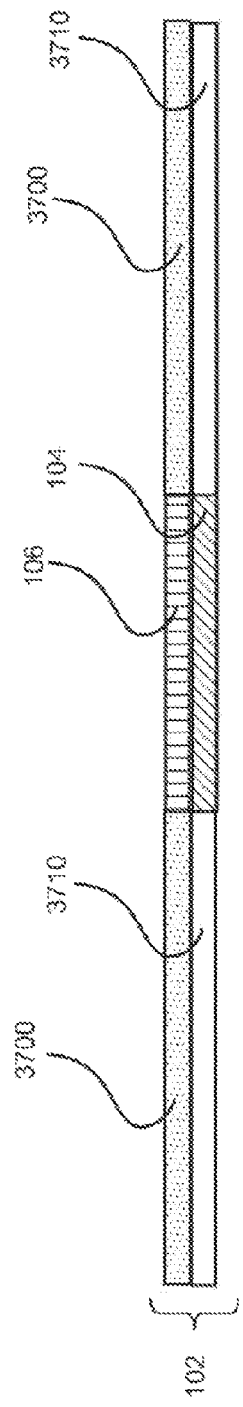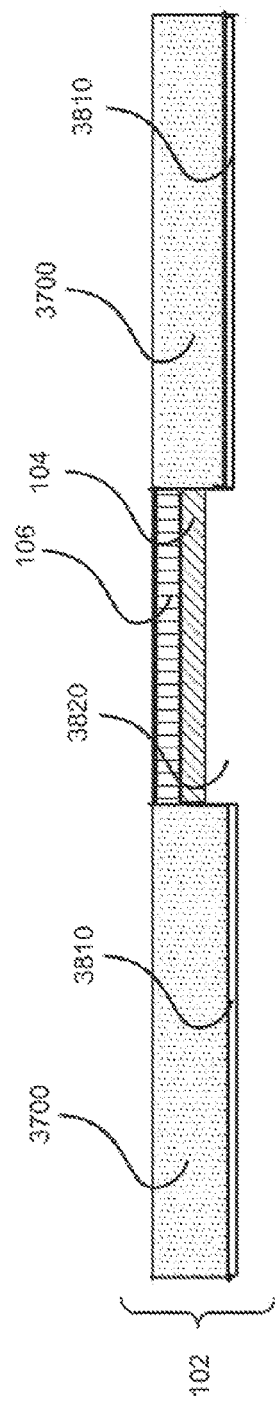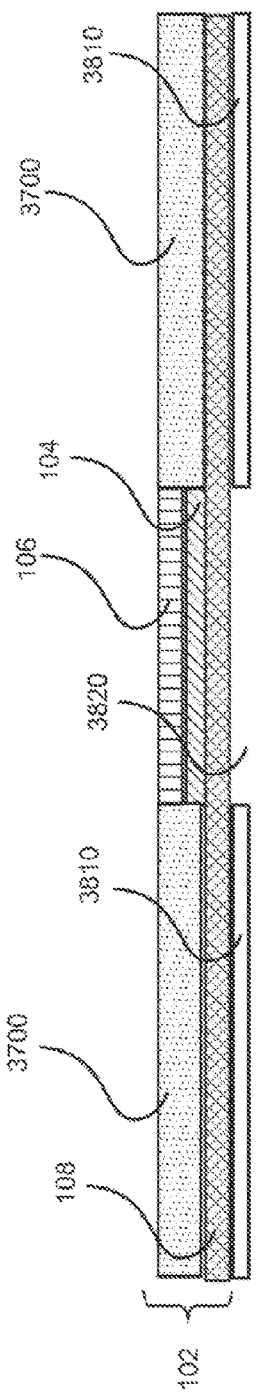

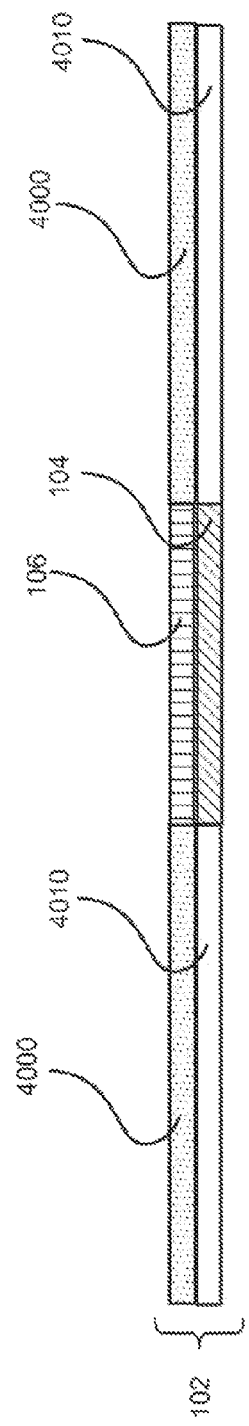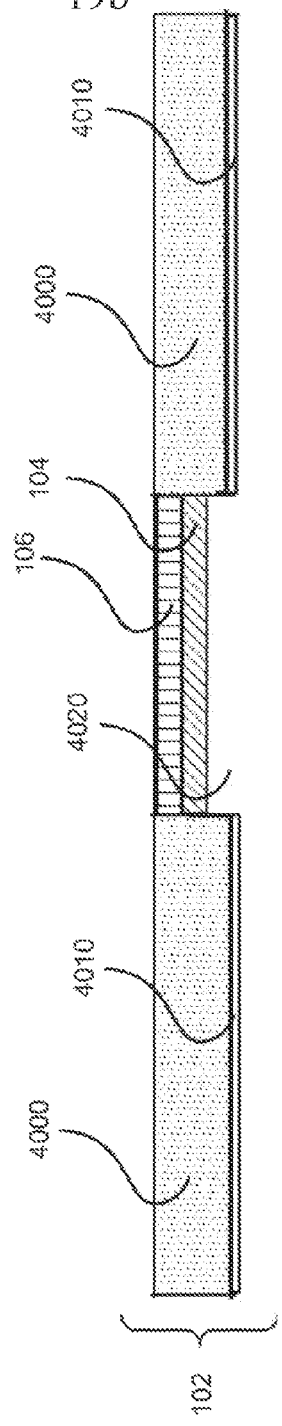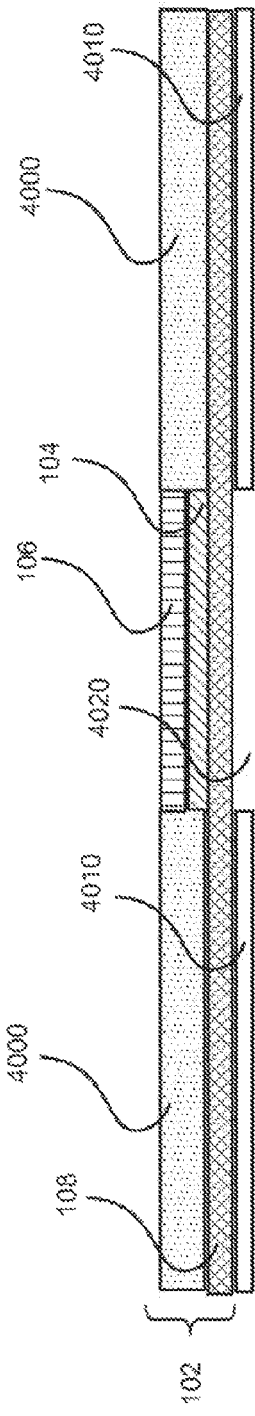

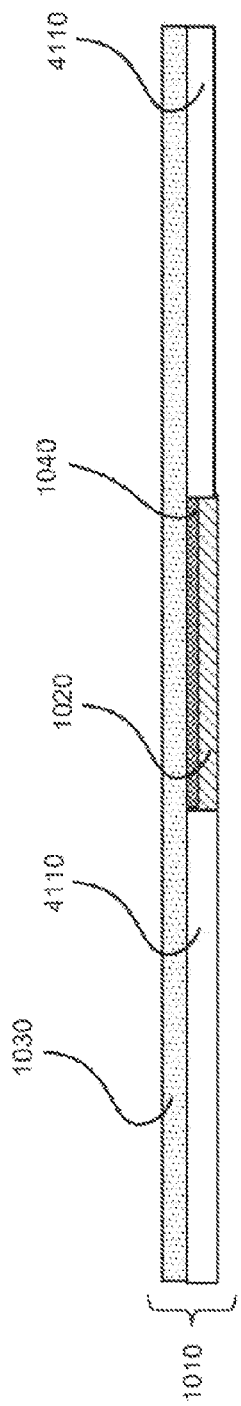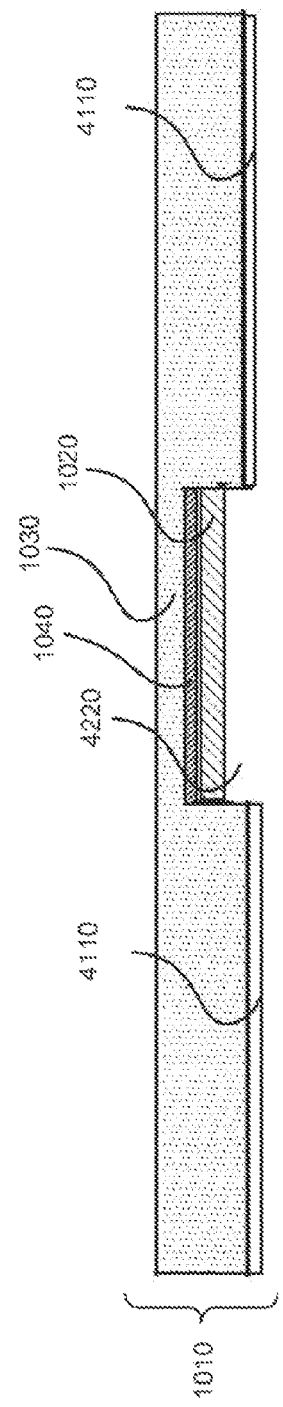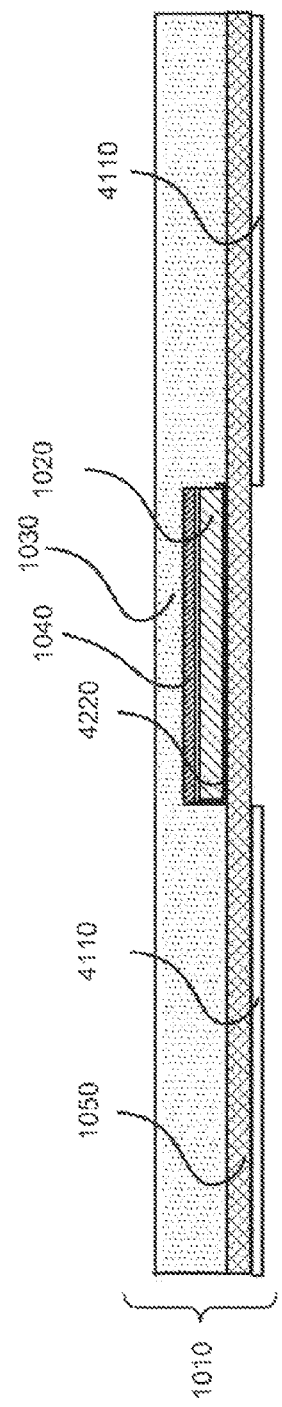

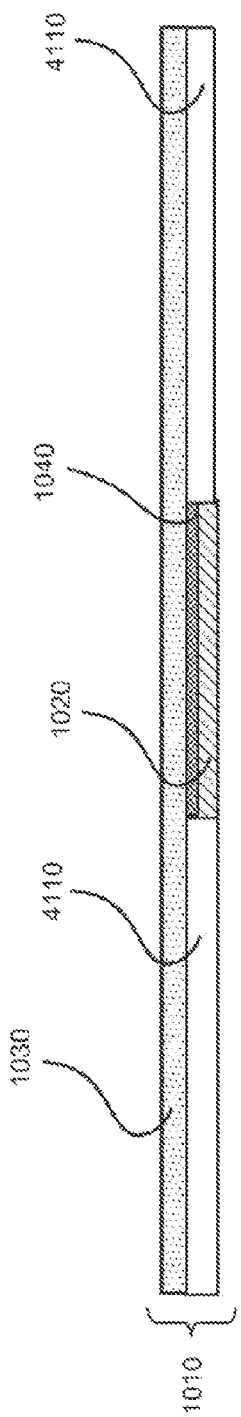
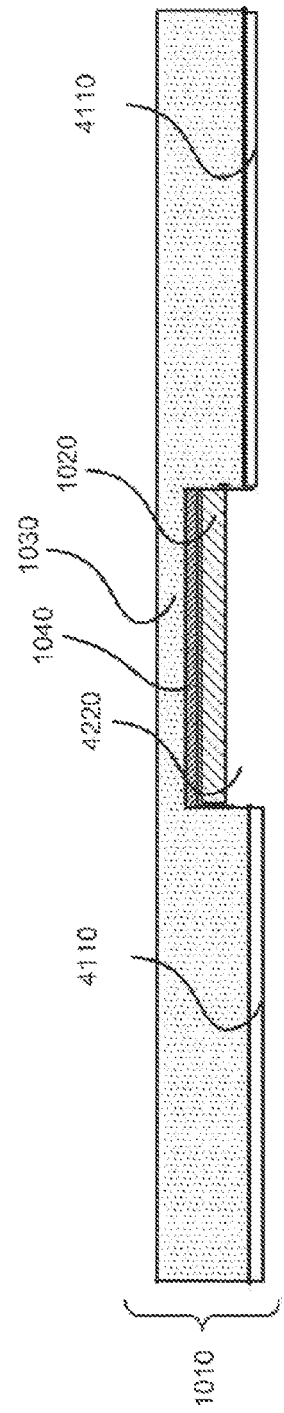
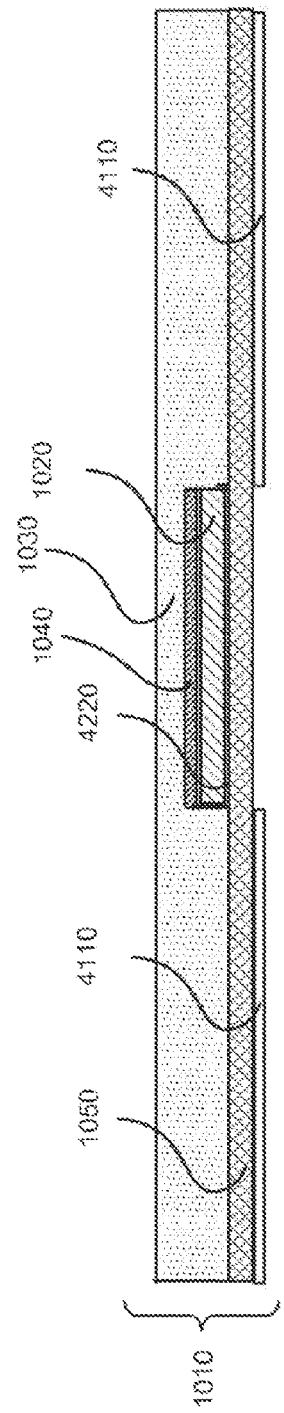

SUBSTRATES FOR NITRIC OXIDE RELEASING DEVICES

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a continuation-in-part of U.S. patent application Ser. No. 11/981,743 now U.S. Pat. No. 8,642,093, entitled Methods and Systems for Use of Photolyzable Nitric Oxide Donors, naming Roderick A. Hyde, Muriel Y. Ishikawa and Lowell L. Wood, Jr. as inventors, filed Oct. 30, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 11/998,864 now U.S. Pat. No. 8,221,690, entitled Systems and Devices that Utilize Photolyzable Nitric Oxide Donors, naming Roderick A. Hyde, Muriel Y. Ishikawa and Lowell L. Wood, Jr. as inventors, filed Nov. 30, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/005,045 now abandoned, entitled Systems and Devices Related to Nitric Oxide Releasing Materials, naming Roderick A. Hyde, Muriel Y. Ishikawa, Leif T. Stordal and Lowell L. Wood, Jr. as inventors, filed Dec.21, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/005,065 now U.S. Pat. No. 7,862,598, entitled Devices and Systems that Deliver Nitric Oxide, naming Roderick A. Hyde, Muriel Y. Ishikawa, Leif T. Stordal and Lowell L. Wood, Jr. as inventors, filed Dec. 21, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/005,132 now U.S. Pat. No. 7,897,399, entitled Nitric Oxide Sensors And Systems, naming Roderick A. Hyde, Muriel Y. Ishikawa, Leif T. Stordal and Lowell L. Wood, Jr. as inventors, filed Dec. 27, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/005,136 now abandoned, entitled Devices Configured to Facilitate Release of Nitric Oxide, naming Roderick A. Hyde, Muriel Y. Ishikawa and Lowell L. Wood, Jr. as inventors, filed Dec. 21, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/005,170 now U.S. Pat. No. 7,975,699; entitled Condoms Configured to Facilitate Release of Nitric Oxide, naming Roderick A. Hyde, Muriel Y. Ishikawa and Lowell L. Wood, Jr. as inventors, filed Dec. 21, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/006,090 now abandoned, entitled Sleeves Configured to Facilitate Release of Nitric Oxide, naming Roderick A. Hyde, Muriel Y. Ishikawa and Lowell L. Wood, Jr. as inventors, filed Dec. 28, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/006,069 now abandoned, entitled Nitric Oxide Permeable Housings, naming Roderick A. Hyde, Muriel Y. Ishikawa and Lowell L. Wood, Jr. as inventors, filed Dec. 28, 2007, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/006,049 now abandoned, entitled Substrates For Nitric Oxide Releasing Devices, naming Roderick A. Hyde, Muriel Y. Ishikawa, Leif T. Stordal and Lowell L. Wood, Jr. as inventors, filed Dec. 28, 2007, which is currently co-pending, or is an application of which a currently co-pending application is entitled to the benefit of the filing date.

For purposes of the USPTO extra-statutory requirements, the present application constitutes a continuation of U.S. patent application Ser. No. 12/008,708, entitled Substrates For Nitric Oxide Releasing Devices, naming Roderick A. Hyde, Muriel Y. Ishikawa, Leif T. Stordal and Lowell L. Wood, Jr. as inventors, filed Jan. 11, 2008 now U.S. Pat. No. 7,846,400, which is currently co-pending, or is an application of which a currently co-pending application is entitled to the benefit of the filing date.

For purposes of the USPTO extra-statutory requirements, the present application constitutes a continuation-in-part of U.S. patent application Ser. No. 12/008,694 now U.S. Pat. No. 8,349,262, entitled Nitric Oxide Permeable Housings, naming Roderick A. Hyde, Muriel Y. Ishikawa and Lowell L. Wood, Jr. as inventors, filed Jan. 11, 2008, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

TECHNICAL FIELD

The present disclosure relates to substrates associated with nitric oxide.

SUMMARY

In some embodiments an apparatus is provided that includes one or more substrates that are configured for operable association with one or more light sources that are configured to emit light that facilitates release of nitric oxide from one or more photolyzable nitric oxide donors. The apparatus may optionally include one or more photolyzable nitric oxide donors. The apparatus may optionally include one or more light sources that are configured to emit light that facilitates release of nitric oxide from the one or more photolyzable nitric oxide donors. In addition to the foregoing, other aspects are described in the claims, drawings, and text forming a part of the present disclosure.

In some embodiments, means include but are not limited to circuitry and/or programming for effecting the herein referenced functional aspects; the circuitry and/or programming can be virtually any combination of hardware, software, and/or firmware configured to effect the herein referenced functional aspects depending upon the design choices of the system designer. In addition to the foregoing, other system aspects means are described in the claims, drawings, and/or text forming a part of the present disclosure.

In some embodiments, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer. In addition to the foregoing, other system aspects are described in the claims, drawings, and/or text forming a part of the present application.

The foregoing summary is illustrative only and is not intended to be in any way limiting. In addition to the illustrative aspects, embodiments, and features described above, further aspects, embodiments, and features will become apparent by reference to the drawings, claims, and the following detailed description.

BRIEF DESCRIPTION OF THE FIGURES

FIG. 4 illustrates alternate embodiments of module 210 of embodiment 200 of apparatus 102 within system 100.

FIG. 5 illustrates alternate embodiments of module 210 of embodiment 200 of apparatus 102 within system 100.

FIG. 6 illustrates alternate embodiments of module 210 of embodiment 200 of apparatus 102 within system 100.

FIG. 11 illustrates alternate embodiments of module 930 of embodiment 900 of apparatus 102 within system 100.

FIG. 17A illustrates a side-view of an embodiment of dressing 102 within system 100 as illustrated in FIG. 16.

FIG. 17B illustrates a side-view of an embodiment of dressing 102 within system 100 as illustrated in FIG. 16.

FIG. 17C illustrates a side-view of an embodiment of dressing 102 within system 100 as illustrated in FIG. 16.

FIG. 19A illustrates a side-view of an embodiment of dressing 102 within system 100 as illustrated in FIG. 18.

FIG. 19B illustrates a side-view of an embodiment of dressing 102 within system 100 as illustrated in FIG. 18.

FIG. 19C illustrates a side-view of an embodiment of dressing 102 within system 100 as illustrated in FIG. 18.

FIG. 21A illustrates a side-view of an embodiment of dressing 1010 within system 1000 as illustrated in FIG. 20.

FIG. 21B illustrates a side-view of an embodiment of dressing 1010 within system 1000 as illustrated in FIG. 20.

FIG. 21C illustrates a side-view of an embodiment of dressing 1010 within system 1000 as illustrated in FIG. 20.

FIG. 23A illustrates a side-view of embodiment of dressing 1010 within system 1000 as illustrated in FIG. 22.

FIG. 23B illustrates a side-view of an embodiment of dressing 1010 within system 1000 as illustrated in FIG. 22.

FIG. 23C illustrates a side-view of an embodiment of dressing 1010 within system 1000 as illustrated in FIG. 22.

DETAILED DESCRIPTION

Figure 1:
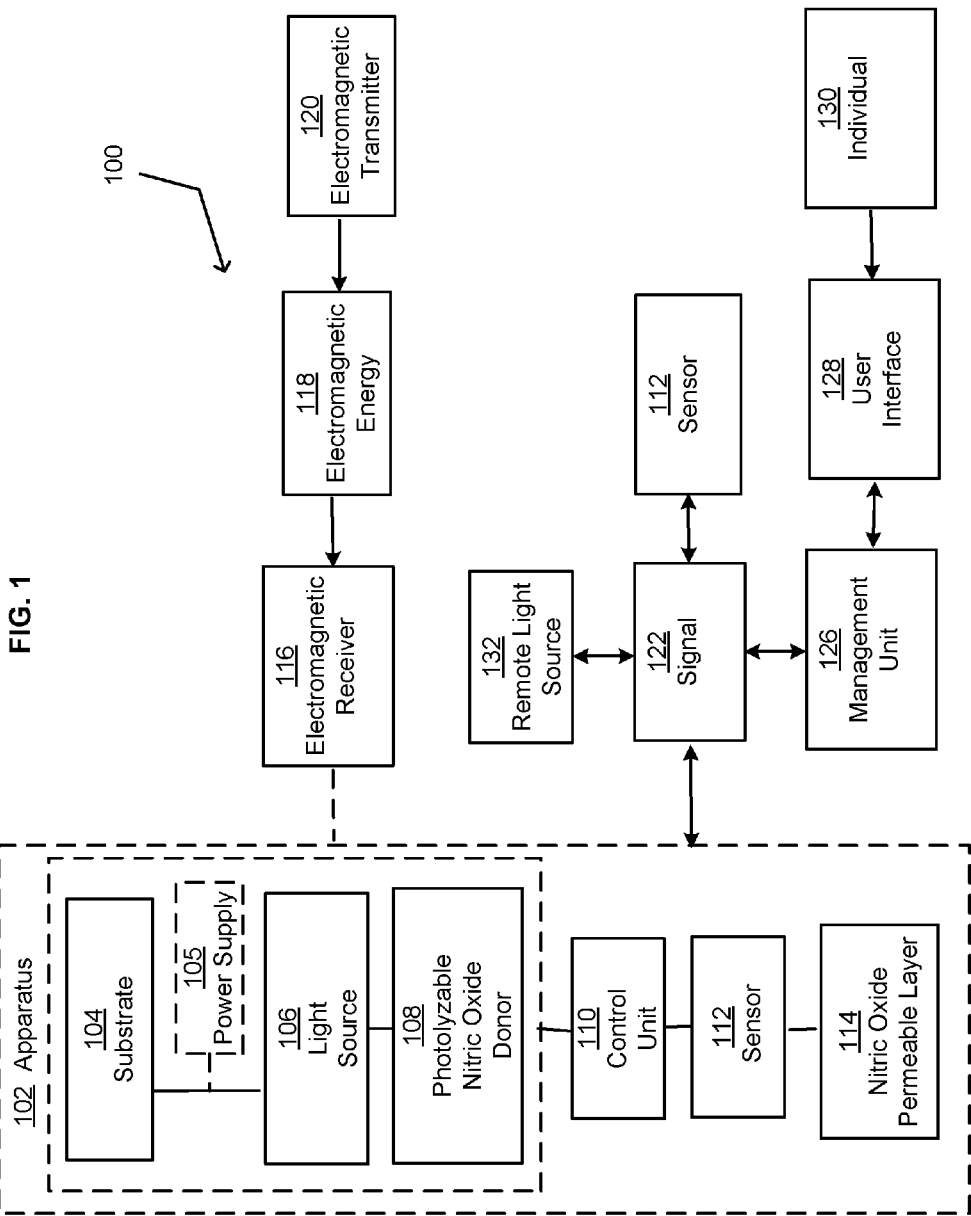
FIG. 1 illustrates an example system 100 in which embodiments may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

FIG. 1 illustrates a system 100 in which embodiments may be implemented. System 100 may include one or more apparatuses 102 that include one or more substrates 104. In some embodiments, one or more apparatuses 102 may include one or more light sources 106. In some embodiments, one or more apparatuses 102 may include one or more photolyzable nitric oxide donors 108. In some embodiments, system 100 may include one or more control units 110, one or more sensors 112, one or more nitric oxide permeable layers 114, and substantially any combination thereof. In some embodiments, the photolyzable nitric oxide donors 108 may be physically coupled with the one or more light sources 106. For example, in some embodiments, the one or more light sources 106 may be coated with the one or more photolyzable nitric oxide donors 108. In some embodiments, the one or more light sources 106 may include one or more polymeric materials that are coupled to at least one of the photolyzable nitric oxide donors 108. In some embodiments, one or more light sources 106 may be coated with a composition that includes one or more photolyzable nitric oxide donors 108. In some embodiments, one or more light sources 106 may be included within a substrate 104 that is coated with one or more photolyzable nitric oxide donors 108. Accordingly, in some embodiments, one or more light sources 106 may be in direct contact with one or more photolyzable nitric oxide donors 108. In some embodiments, one or more light sources 106 may be in indirect contact with one or more photolyzable nitric oxide donors 108. In some embodiments, the apparatus 102 may include one or more operably coupled control units 110. In some embodiments, the one or more control units 110 may be operably coupled to the one or more light sources 106. In some embodiments, the one or more control units 110 may be operably coupled to the one or more light sources 106 and may be used to control the operation of the one or more light sources 106. In some embodiments, the one or more control units 110 may be configured to receive one or more signals 122. In some embodiments, the one or more control units 110 may be configured to receive one or more signals 122 from one or more transmitters. In some embodiments, the one or more control units 110 may be configured to receive one or more signals 122 from one or more sensors 112. In some embodiments, one or more nitric oxide permeable layers 114 may be configured to enclose one or more photolyzable nitric oxide donors 108. In some embodiments, one or more nitric oxide permeable layers 114 may be configured to enclose one or more photolyzable nitric oxide donors 108 and one or more light sources 106. In some embodiments, one or more nitric oxide permeable layers 114 may be configured to enclose one or more photolyzable nitric oxide donors 108, one or more light sources 106, and one or more control units 110. In some embodiments, one or more nitric oxide permeable layers 114 may be configured to enclose one or more photolyzable nitric oxide donors 108, one or more light sources 106, one or more control units 110, and one or more sensors 112. In some embodiments, one or more nitric oxide permeable layers 114 may be configured to enclose one or more photolyzable nitric oxide donors 108, one or more light sources 106, one or more control units 110, one or more sensors 112, or substantially any combination thereof. In some embodiments, one or more apparatuses 102 may be operably coupled to one or more electromagnetic receivers 116. In some embodiments, system 100 may include one or more electromagnetic receivers 116 that are configured to receive electromagnetic energy 118. In some embodiments, system 100 may include one or more electromagnetic receivers 116 that are configured to receive electromagnetic energy 118 that is transmitted by one or more electromagnetic transmitters 120. In some embodiments, the one or more electromagnetic receivers 116 may be operably coupled to the apparatus 102. In some embodiments, the one or more electromagnetic receivers 116 may be operably coupled to the one or more light sources 106. In some embodiments, the one or more electromagnetic receivers 116 may be operably coupled to the one or more light sources 106 such that the one or more light sources 106 are energized through receipt of electromagnetic energy 118. In some embodiments, system 100 may include one or more light sources 106, one or more photolyzable nitric oxide donors 108, one or more control units 110, one or more nitric oxide permeable layers 114, one or more sensors 112, one or more electromagnetic receivers 116, one or more electromagnetic transmitters 120, or substantially any combination thereof.

Apparatus

System 100 includes one or more apparatuses 102. An apparatus 102 may be configured in numerous ways. In some embodiments, an apparatus 102 may be configured to deliver nitric oxide to a surface of an individual 130. In some embodiments, an apparatus 102 may be configured for application to an inside surface of an individual 130. For example, in some embodiments, an apparatus 102 may be configured to deliver nitric oxide to an oral surface, a nasal surface, and the like. In some embodiments, an apparatus 102 may be configured for application to an outside surface of an individual 130. For example, in some embodiments, an apparatus 102 may be configured to deliver nitric oxide to the skin of an individual 130. Accordingly, an apparatus 102 may be configured in numerous ways to deliver nitric oxide to a surface or region of an individual 130. In some embodiments, an apparatus 102 may be configured to deliver nitric oxide as a therapeutic agent (e.g., U.S. Patent Application No. 2007/0088316). For example, in some embodiments, an apparatus 102 may be configured to deliver nitric oxide to a person to combat infection. In some embodiments, an apparatus 102 may be configured to deliver nitric oxide to a person to assist in removal of necrotic tissue. In some embodiments, an apparatus 102 may be configured to deliver nitric oxide to a person to reduce inflammation. In some embodiments, an apparatus 102 may be configured to deliver nitric oxide to a person to upregulate the expression of collagenase. In some embodiments, an apparatus 102 may be configured to deliver nitric oxide to a person to facilitate vascularisation. In some embodiments, an apparatus 102 may be configured to deliver nitric oxide to a person suffering from diabetes. For example, in some embodiments, an apparatus 102 may be configured to deliver nitric oxide to tissue lesions. In some embodiments, an apparatus 102 may be configured to deliver nitric oxide as a sanitizing agent. In some embodiments, an apparatus may be configured to deliver nitric oxide to an accident victim. For example, in some embodiments, an apparatus 102 may be configured as a bag into which a burn victim may be inserted. In some embodiments, an apparatus 102 may be configured to deliver nitric oxide to the surface of a table, a chair, to surgical instruments, and the like.

In some embodiments, an apparatus 102 may be configured as a wearable article. Examples of such wearable articles include, but are not limited to, hats, gloves, mittens, socks, pants, shirts, hoods, patches, tapes, wraps, and the like. In some embodiments, an apparatus 102 may be configured as a bag. For example, in some embodiments, an apparatus 102 may be configured as a bag that will enclose a person. In some embodiments, such a bag may be used to deliver nitric oxide to the surface of an individual 130. In some embodiments, an apparatus 102 may be configured as a sleeve that will enclose a portion of a person. In some embodiments, such a sleeve may be used to deliver nitric oxide to the surface of an individual 130.

In some embodiments, an apparatus 102 may be configured to deliver nitric oxide in a controlled manner. For example, in some embodiments, an apparatus 102 may be associated with a nitric oxide sensor 112 that facilitates generation of nitric oxide in a controlled manner. For example, in some embodiments, one or more light sources 106 may be operably coupled with one or more sensors 112 such that the light sources 106 act in response to the one or more sensors 112. Accordingly, in some embodiments, the light sources 106 may be regulated to facilitate release of nitric oxide from one or more photolyzable nitric oxide donors 108 in a controlled manner. In some embodiments, such a configuration allows the nitric oxide concentration within an area to be maintained within a selected range. Numerous concentrations of nitric oxide may be maintained. For example, in some embodiments, the nitric oxide concentration within a wound area may be maintained at about 160 to about 400 parts per million. Such a concentration range has been reported to reduce microbial infection within a wound site, reduce inflammation, and increase collagenase expression without inducing toxicity to healthy cells within the wound site (e.g., U.S. Patent Application No. 2007/0088316).

Light Source

Numerous light sources 106 may be used within system 100. In some embodiments, one or more light sources 106 may be used to facilitate release of nitric oxide from one or more photolyzable nitric oxide donors 108. In some embodiments, one or more light sources 106 may be configured to emit light of multiple wavelengths. In some embodiments, one or more light sources 106 may be configured to emit light that is selected to facilitate release of nitric oxide from one or more photolyzable nitric oxide donors 108. For example, in some embodiments, one or more light sources 106 may be configured to emit one or more wavelengths of light that are selected to facilitate release of nitric oxide from one or more identified photolyzable nitric oxide donors 108. In some embodiments, one or more light sources 106 may emit one or more wavelengths of light that are selected based on the absorption spectrum of one or more photolyzable nitric oxide donors 108. In some embodiments, one or more light sources 106 may emit one or more wavelengths of light that are selected based on decomposition of one or more photolyzable nitric oxide donors 108. For example, in some embodiments, one or more light sources 106 may be configured to emit one or more wavelengths of light that cause decomposition of one or more photolyzable nitric oxide donors 108 without causing injury to adjacent structures and/or tissues. In some embodiments, a first light source 106 may be configured to emit one or more wavelengths of light that cause a first photolyzable nitric oxide donor 108 to release nitric oxide and a second light source 106 may be configured to emit one or more wavelengths of light that cause a second photolyzable nitric oxide donor 108 to release nitric oxide. Accordingly, numerous light sources 106 may be coupled with numerous types of photolyzable nitric oxide donors 108 to provide for selective release of nitric oxide.

In some embodiments, one or more light sources 106 may include one or more quantum dots (e.g., U.S. Pat. No. 7,235,361; herein incorporated by reference). For example, in some embodiments, one or more light sources 106 may be configured to emit one or more wavelengths of light that are absorbed by one or more quantum dots. In some embodiments, one or more quantum dots may be configured to absorb light and then emit one or more wavelengths of light that cause release of nitric oxide from one or more photolyzable nitric oxide donors 108. Accordingly, in some embodiments, emission from one or more first quantum dots may be tuned to facilitate release of nitric oxide from one or more first photolyzable nitric oxide donors 108 and emission from one or more second quantum dots may be tuned to facilitate release of nitric oxide from one or more second photolyzable nitric oxide donors 108.

A light source 106 may be configured in numerous ways. For example, in some embodiments, one or more light sources 106 may be configured to include one or more energy sources (e.g., power supply 105, one or more batteries, one or more thin-film batteries, one or more solar cells, one or more capacitors, and the like). In some embodiments, one or more light sources 106 may be configured to include one or more light emitters (e.g., one or more light emitting diodes, one or more filaments, and the like). In some embodiments, one or more light sources 106 may be configured to include one or more optical fibers. In some embodiments, one or more light sources 106 may be configured to include one or more control units 110.

In some embodiments, a light source 106 may be remotely controlled. For example, in some embodiments, one or more light sources 106 may be configured to receive one or more signals 122 that include instructions for operation of the one or more light sources 106. Such instructions may be associated with emission of light, non-emission of light, time when light is emitted, length of light emission, intensity of light emission, wavelengths of emitted light, and the like.

In some embodiments, light sources 106 may be configured to include one or more control units 110. In some embodiments, one or more light sources 106 may be configured to include a switch that may be used to turn the light source 106 on and off. For example, in some embodiments, a light source 106 may be configured to include a push button switch to turn the light source 106 on and off.

In some embodiments, one or more light sources 106 may include one or more light emitters that are coupled to one or more electromagnetic receivers 116. The one or more electromagnetic receivers 116 may be configured to couple with one or more electromagnetic transmitters 120 that produce one or more electromagnetic fields that induce an electrical current to flow in the one or more electromagnetic receivers 116 to energize the light emitters (e.g., U.S. Pat. No. 5,571,152; herein incorporated by reference). Accordingly, in some embodiments, one or more light sources 106 may be configured such that they are remotely coupled to an energy source.

A light source 106 may be configured to emit numerous types of light. In some embodiments, emitted light may be visible light. In some embodiments, emitted light may be infrared light. In some embodiments, emitted light may be ultraviolet light. In some embodiments, emitted light may be substantially any combination of visible light, infrared light, and/or ultraviolet light. In some embodiments, one or more light sources 106 may emit fluorescent light. In some embodiments, one or more light sources 106 may emit phosphorescent light.

In some embodiments, one or more light sources 106 may be configured to emit light continuously. In some embodiments, one or more light sources 106 may be configured to emit light as a pulse. In some embodiments, one or more light sources 106 may be configured to emit light as a flash. In some embodiments, one or more light sources 106 may be configured to emit light continuously, as a pulse, as a flash, or substantially any combination thereof.

In some embodiments, one or more light emitters and/or light sources 106 may be configured to provide for upconversion of energy. In some embodiments, infrared light may be upconverted to visible light (e.g., Mendioroz et al., Optical Materials, 26:351-357 (2004)). In some embodiments, infrared light may be upconverted to ultraviolet light (e.g., Mendioroz et al., Optical Materials, 26:351-357 (2004)). In some embodiments, one or more light sources 106 may include one or more rare-earth materials (e.g., ytterbium-erbium, ytterbium-thulium, or the like) that facilitate upconversion of energy (e.g., U.S. Pat. No. 7,088,040; herein incorporated by reference). For example, in some embodiments, one or more light sources 106 may be associated with $Nd^{3+}$ doped $KPb_2Cl_5$ crystals. In some embodiments, one or more light sources 106 may be associated with thiogallates doped with rare earths, such as $CaGa_2S_4:Ce^{3+}$ and $SrGa_2S_4:Ce^{3+}$. In some embodiments, one or more light sources 106 may be associated with aluminates that are doped with rare earths, such as $YAlO_3:Ce^{3+}$, $YGaO_3:Ce^{3+}$, $Y(Al,Ga)O_3:Ce^{3+}$, and orthosilicates $M_2SiO_5:Ce^{3+}$ (M:Sc, Y, Sc) doped with rare earths, such as, for example, $Y_2SiO_5$: $Ce^{3+}$. In some embodiments, yttrium may be replaced by scandium or lanthanum (e.g., U.S. Pat. Nos. 6,812,500 and 6,327,074; herein incorporated by reference). Numerous materials that may be used to upconvert energy have been described (e.g., U.S. Pat. Nos. 5,956,172; 5,943,160; 7,235,189; 7,215,687; herein incorporated by reference).

Remote Light Source

Numerous remote light sources 132 may be used within system 100. In some embodiments, one or more remote light sources 132 may be used to facilitate release of nitric oxide from one or more photolyzable nitric oxide donors 108. In some embodiments, one or more remote light sources 132 may be configured to emit light of multiple wavelengths. In some embodiments, one or more remote light sources 132 may be configured to emit light that is selected to facilitate release of nitric oxide from one or more photolyzable nitric oxide donors 108. For example, in some embodiments, one or more remote light sources 132 may be configured to emit one or more wavelengths of light that are selected to facilitate release of nitric oxide from one or more identified photolyzable nitric oxide donors 108. In some embodiments, one or more light sources 106 may emit one or more wavelengths of light that are selected based on the absorption spectrum of one or more photolyzable nitric oxide donors 108. In some embodiments, one or more remote light sources 132 may emit one or more wavelengths of light that are selected based on decomposition of one or more photolyzable nitric oxide donors 108. For example, in some embodiments, one or more remote light sources 132 may be configured to emit one or more wavelengths of light that cause decomposition of one or more photolyzable nitric oxide donors 108 without causing injury to adjacent structures and/or tissues. In some embodiments, a first light source 106 may be configured to emit one or more wavelengths of light that cause a first photolyzable nitric oxide donor 108 to release nitric oxide and a second light source 106 may be configured to emit one or more wavelengths of light that cause a second photolyzable nitric oxide donor 108 to release nitric oxide. Accordingly, numerous remote light sources 132 may be coupled with numerous types of photolyzable nitric oxide donors 108 to provide for selective release of nitric oxide.

In some embodiments, one or more remote light sources 132 may include one or more quantum dots (e.g., U.S. Pat. No. 7,235,361; herein incorporated by reference). For example, in some embodiments, one or more remote light sources 132 may be configured to emit one or more wavelengths of light that are absorbed by one or more quantum dots. In some embodiments, one or more quantum dots may be configured to absorb light and then emit one or more wavelengths of light that cause release of nitric oxide from one or more photolyzable nitric oxide donors 108. Accordingly, in some embodiments, emission from one or more first quantum dots may be tuned to facilitate release of nitric oxide from one or more first photolyzable nitric oxide donors 108 and emission from one or more second quantum dots may be tuned to facilitate release of nitric oxide from one or more second photolyzable nitric oxide donors 108.

A remote light source 132 may be configured in numerous ways. For example, in some embodiments, one or more remote light sources 132 may be configured to include one or more energy sources (e.g., one or more batteries, one or more thin-film batteries, one or more solar cells, one or more capacitors, and the like). In some embodiments, one or more remote light sources 132 may be configured to include one or more light emitters (e.g., one or more light emitting diodes, one or more filaments, and the like). In some embodiments, one or more remote light sources 132 may be configured to include one or more optical fibers. In some embodiments, one or more remote light sources 132 may be configured to include one or more control units.

In some embodiments, a remote light source 132 may be remotely controlled. For example, in some embodiments, one or more remote light sources 132 may be configured to receive one or more signals 122 that include instructions for operation of the one or more remote light sources 132. Such instructions may be associated with emission of light, non-emission of light, time when light is emitted, length of light emission, intensity of light emission, wavelengths of emitted light, and the like.

In some embodiments, remote light sources 132 may be configured to include one or more control units. In some embodiments, one or more remote light sources 132 may be configured to include a switch that may be used to turn the remote light source 132 on and off. For example, in some embodiments, a remote light source 132 may be configured to include a push button switch to turn the remote light source 132 on and off.

In some embodiments, one or more remote light sources 132 may include one or more light emitters that are coupled to one or more electromagnetic receivers 116. The one or more electromagnetic receivers 116 may be configured to couple with one or more electromagnetic transmitters 120 that produce one or more electromagnetic fields that induce an electrical current to flow in the one or more electromagnetic receivers 116 to energize the light emitters (e.g., U.S. Pat. No. 5,571,152; herein incorporated by reference). Accordingly, in some embodiments, one or more remote light sources 132 may be configured such that they are remotely coupled to an energy source.

A light source 106 may be configured to emit numerous types of light. In some embodiments, emitted light may be visible light. In some embodiments, emitted light may be infrared light. In some embodiments, emitted light may be ultraviolet light. In some embodiments, emitted light may be substantially any combination of visible light, infrared light, and/or ultraviolet light. In some embodiments, one or more remote light sources 132 may emit fluorescent light. In some embodiments, one or more remote light sources 132 may emit phosphorescent light.

In some embodiments, one or more remote light sources 132 may be configured to emit light continuously. In some embodiments, one or more remote light sources 132 may be configured to emit light as a pulse. In some embodiments, one or more remote light sources 132 may be configured to emit light as a flash. In some embodiments, one or more remote light sources 132 may be configured to emit light continuously, as a pulse, as a flash, or substantially any combination thereof.

In some embodiments, one or more light emitters and/or remote light sources 132 may be configured to provide for upconversion of energy. In some embodiments, infrared light may be upconverted to visible light (e.g., Mendioroz et al., Optical Materials, 26:351-357 (2004)). In some embodiments, infrared light may be upconverted to ultraviolet light (e.g., Mendioroz et al., Optical Materials, 26:351-357 (2004)). In some embodiments, one or more remote light sources 132 may include one or more rare-earth materials (e.g., ytterbium-erbium, ytterbium-thulium, or the like) that facilitate upconversion of energy (e.g., U.S. Pat. No. 7,088,040; herein incorporated by reference). For example, in some embodiments, one or more remote light sources 132 may be associated with $Nd^{3+}$ doped $KPb_2Cl_5$ crystals. In some embodiments, one or more remote light sources 132 may be associated with thiogallates doped with rare earths, such as $CaGa_2S_4:Ce^{3+}$ and $SrGa_2S_4:Ce^{3+}$. In some embodiments, one or more remote light sources 132 may be associated with aluminates that are doped with rare earths, such as $YAlO_3:Ce^{3+}$, $YGaO_3:Ce^{3+}$, $Y(Al,Ga)O_3:Ce^{3+}$, and orthosilicates $M_2SiO_5:Ce^{3+}$ (M:Sc, Y, Sc) doped with rare earths, such as, for example, $Y_2SiO_5:Ce^{3+}$. In some embodiments, yttrium may be replaced by scandium or lanthanum (e.g., U.S. Pat. Nos. 6,812,500 and 6,327,074; herein incorporated by reference). Numerous materials that may be used to upconvert energy have been described (e.g., U.S. Pat. Nos. 5,956,172; 5,943,160; 7,235,189; 7,215,687; herein incorporated by reference).

Photolyzable Nitric Oxide Donor/Nitric Oxide

Numerous photolyzable nitric oxide donors 108 may be used within system 100. Examples of such photolyzable nitric oxide donors 108 include, but are not limited to, diazeniumdiolates (e.g., U.S. Pat. Nos. 7,105,502; 7,122,529; 6,673,338; herein incorporated by reference), trans-[RuCl([15]aneN4)NO]+2 (Ferezin et al., Nitric Oxide, 13:170-175 (2005), Bonaventura et al., Nitric Oxide, 10:83-91 (2004)), nitrosyl ligands (e.g., U.S. Pat. No. 5,665,077; herein incorporated by reference, Chmura et al., Nitric Oxide, 15:370-379 (2005), Flitney et al., Br. J. Pharmacol., 107:842-848 (1992), Flitney et al., Br. J. Pharmacol., 117:1549-1557 (1996), Matthews et al., Br. J. Pharmacol., 113:87-94 (1994)), 6-Nitrobenzo[a]pyrene (e.g., Fukuhara et al., J. Am. Chem. Soc., 123:8662-8666 (2001)), S-nitroso-glutathione (e.g., Rotta et al., Braz. J. Med. Res., 36:587-594 (2003), Flitney and Megson, J. Physiol., 550:819-828 (2003)), S-nitrosothiols (e.g., Andrews et al., British Journal of Pharmacology, 138:932-940 (2003), Singh et al., FEBS Lett., 360:47-51 (1995)), 2-Methyl-2-nitrosopropane (e.g., Pou et al., Mol. Pharm., 46:709-715 (1994), Wang et al., Chem. Rev., 102:1091-1134 (2002)), imidazolyl derivatives (e.g., U.S. Pat. No. 5,374,710; herein incorporated by reference).

In some embodiments, one or more photolyzable nitric oxide donors 108 may be used in association with additional nitric oxide donors that are not photolyzable. In some embodiments, one or more photolyzable nitric oxide donors 108 may be used in association with additional agents. Examples of such additional agents include, but are not limited to, enzyme inhibitors (e.g., U.S. Pat. No. 6,943,166; herein incorporated by reference), agents that increase the effects and/or concentration of nitric oxide (e.g., methylene blue and N(w)-nitro-L-arginine (L-NOARG) (see Chen and Gillis, Biochem. Biophys. Res. Commun., 190, 559-563 (1993) and Kim et al., J. Vet. Sci., 1:81-86 (2000)), L-arginine (e.g., U.S. Published Patent Application No. 20020068365 and U.S. Pat. No. 6,635,273; herein incorporated by reference), agents that stabilize nitric oxide donors (e.g., dimethly sulfoxide and ethanol), agents that increase the half life of nitric oxide (e.g., U.S. Published Patent Application No. 20030039697; herein incorporated by reference), and the like.

Control Unit

Numerous types of control units 110 may be used within system 100. In some embodiments, one or more control units 110 may be operably coupled with one or more light sources 106, one or more remote light sources 132, one or more sensors 112, one or more electromagnetic receivers 116, one or more electromagnetic transmitters 120, or substantially any combination thereof. In some embodiments, one or more control units 110 may be operably coupled to other components through use of one or more wireless connections, one or more hardwired connections, or substantially any combination thereof. Control units 110 may be configured in numerous ways. For example, in some embodiments, a control unit 110 may be configured as an on/off switch.

In some embodiments, a control unit 110 may be configured to turn a light source 106 on and/or off. In some embodiments, a control unit 110 may be configured to control the emission of light from one or more light sources 106. For example, in some embodiments, one or more control units 110 may regulate the intensity of light emitted from one or more light sources 106, the duration of light emitted from one or more light sources 106, the frequency of light emitted from one or more light sources 106, wavelengths of light emitted from one or more light sources 106, one or more times when light is emitted from one or more light sources 106, one or more times when light is not emitted from one or more light sources 106, or substantially any combination thereof. In some embodiments, one or more control units 110 may be configured to receive one or more signals 122 from one or more sensors 112. Accordingly, in some embodiments, one or more control units 110 may be configured to control one or more light sources 106 in response to one or more signals 122 received from one or more sensors 112. For example, in some embodiments, one or more sensors 112 may sense a low concentration of nitric oxide in one or more tissues and send one or more signals 122 to one or more control units 110. The one or more control units 110 may then turn one or more light sources 106 on to facilitate release of nitric oxide from one or more photolyzable nitric oxide donors 108. Accordingly, in some embodiments, one or more sensors 112 may sense a high concentration of nitric oxide in one or more tissues and send one or more signals 122 to one or more control units 110. The one or more control units 110 may then turn one or more light sources 106 off to end release of nitric oxide from one or more photolyzable nitric oxide donors 108. In some embodiments, one or more control units 110 may be programmed to control one or more light sources 106. For example, in some embodiments, one or more control units 110 may be programmed to turn one or more light sources 106 on for a predetermined amount of time and then turn off. Accordingly, in some embodiments, one or more control units 110 may be preprogrammed. In some embodiments, one or more control units 110 may be dynamically programmed. For example, in some embodiments, one or more management units 126 may receive one or more signals 122 from one or more sensors 112 and program one or more control units 110 in response to the one or more signals 122 received from the one or more sensors 112. In some embodiments, one or more control units 110 may include one or more receivers that are able to receive one or more signals 122, one or more information packets, or substantially any combination thereof. Control units 110 may be configured in numerous ways. For example, in some embodiments, one or more control units 110 may be operably coupled to one or more light sources 106 that include numerous light emitting diodes that emit light of different wavelengths. Accordingly, in some embodiments, one or more control units 110 may control the wavelengths of light emitted by the one or more light sources 106 by controlling the operation of light emitting diodes that emit light of the selected wavelength. Accordingly, control units 110 may be configured in numerous ways and utilize numerous types of mechanisms.

In some embodiments, a control unit 110 may be configured to turn a remote light source 132 on and/or off. In some embodiments, a control unit 110 may be configured to control the emission of light from one or more remote light sources 132. For example, in some embodiments, one or more control units 110 may regulate the intensity of light emitted from one or more remote light sources 132, the duration of light emitted from one or more remote light sources 132, the frequency of light emitted from one or more remote light sources 132, wavelengths of light emitted from one or more remote light sources 132, one or more times when light is emitted from one or more remote light sources 132, one or more times when light is not emitted from one or more remote light sources 132, or substantially any combination thereof. In some embodiments, one or more control units 110 may be configured to receive one or more signals 122 from one or more sensors 112. Accordingly, in some embodiments, one or more control units 110 may be configured to control one or more remote light sources 132 in response to one or more signals 122 received from one or more sensors 112. For example, in some embodiments, one or more sensors 112 may sense a low concentration of nitric oxide in one or more tissues and send one or more signals 122 to one or more control units 110. The one or more control units 110 may then turn one or more remote light sources 132 on to facilitate release of nitric oxide from one or more photolyzable nitric oxide donors 108. Accordingly, in some embodiments, one or more sensors 112 may sense a high concentration of nitric oxide in one or more tissues and send one or more signals 122 to one or more control units 110. The one or more control units 110 may then turn one or more remote light sources 132 off to end release of nitric oxide from one or more photolyzable nitric oxide donors 108. In some embodiments, one or more control units 110 may be programmed to control one or more remote light sources 132. For example, in some embodiments, one or more control units 110 may be programmed to turn one or more remote light sources 132 on for a predetermined amount of time and then turn off. Accordingly, in some embodiments, one or more control units 110 may be preprogrammed. In some embodiments, one or more control units 110 may be dynamically programmed. For example, in some embodiments, one or more management units 126 may receive one or more signals 122 from one or more sensors 112 and program one or more control units 110 in response to the one or more signals 122 received from the one or more sensors 112. In some embodiments, one or more control units 110 may include one or more receivers that are able to receive one or more signals 122, one or more information packets, or substantially any combination thereof. Control units 110 may be configured in numerous ways. For example, in some embodiments, one or more control units 110 may be operably coupled to one or more remote light sources 132 that include numerous light emitting diodes that emit light of different wavelengths. Accordingly, in some embodiments, one or more control units 110 may control the wavelengths of light emitted by the one or more remote light sources 132 by controlling the operation of light emitting diodes that emit light of the selected wavelength. Accordingly, control units 110 may be configured in numerous ways and utilize numerous types of mechanisms.

Substrate

Numerous substrates 104 may be used within system 100. Substrates 104 may be constructed from numerous types of materials and combinations of materials. Examples of such materials include, but are not limited to, metals, metal alloys, polymers, copolymers, ceramics, cloth, fabric, and the like. Substrates 104 may be configured in numerous ways. For example, in some embodiments, a substrate 104 may be one or more sheets of one or more materials to which one or more light sources 106 and one or more photolyzable nitric oxide donors 108 may be associated. In some embodiments, a substrate 104 may be configured to accept one or more light sources 106. For example, in some embodiments, a substrate 104 may include electrical connections that may be operably coupled to one or more light sources 106. In some embodiments, a substrate 104 may be configured to be associated with one or more power supplies (e.g. power supply 105). For example, in some embodiments, one or more substrates 104 may be configured to associate with one or more solar cells. In some embodiments, one or more substrates 104 may be configured to associate with one or more batteries (e.g., thin-film batteries). In some embodiments, one or more substrates 104 may be configured to associate with one or more capacitors.

Substrates 104 may exhibit numerous physical characteristics. For example, in some embodiments, substrates 104 may be elastomeric. Methods to prepare elastomeric materials are known and have been reported (e.g., U.S. Pat. Nos. 6,639,007; 6,673,871; 7,105,607). In some embodiments, substrates 104 may be inelastic. For example, in some embodiments, a substrate 104 may be fabricated from one or more metal foils. In some embodiments, substrates 104 may be fabricated with pressure sensitive fibers. For example, in some embodiments, a substrate 104 may include one or more elastomeric materials that self-adhere. Accordingly, in some embodiments, a substrate 104 may be configured in the form of self-adhering athletic tape. In some embodiments, a substrate 104 may include one or more adhesives that are applied to one or more portions of the substrate 104. Accordingly, substrates 104 may be fabricated in numerous configurations. In some embodiments, one or more substrates 104 may include one or more storage films that are configured for energy storage and energy conversion (e.g., U.S. Pat. No. 7,238,628).

Nitric Oxide Permeable Layer

Numerous types of nitric oxide permeable layers 114 may be used within system 100. Nitric oxide permeable layers 114 may be configured for application to an individual 130. Nitric oxide permeable layers 114 may be configured to facilitate application of nitric oxide to a surface. In some embodiments, one or more nitric oxide permeable layers 114 may be configured to facilitate application of nitric oxide to one or more surfaces of an individual 130. For example, in some embodiments, one or more nitric oxide permeable layers 114 may be configured as a sheet that may be positioned on a skin surface of an individual 130 to deliver nitric oxide to the skin surface. In some embodiments, a nitric oxide permeable layer 114 may be configured as a wearable article. Examples of such wearable articles include, but are not limited to, hats, gloves, mittens, pants, shirts, hoods, patches, tapes, wraps, and the like. In some embodiments, nitric oxide permeable layers 114 may be configured as bags. For example, in some embodiments, one or more nitric oxide permeable layers 114 may be configured as a bag that will enclose a person. In some embodiments, such a bag may be used to deliver nitric oxide to the surface of an individual 130. In some embodiments, one or more nitric oxide permeable layers 114 may be configured as a sleeve that will enclose a portion of a person. In some embodiments, such a sleeve may be used to deliver nitric oxide to the surface of an individual 130. In some embodiments, one or more nitric oxide permeable layers 114 may be configured to enclose at least a portion of one or more photolyzable nitric oxide donors 108. In some embodiments, one or more nitric oxide permeable layers 114 may be configured to enclose at least a portion of one or more light sources 106. In some embodiments, one or more nitric oxide permeable layers 114 may be configured to enclose at least a portion of one or more control units 110. In some embodiments, one or more nitric oxide permeable layers 114 may be configured to enclose at least a portion of one or more sensors 112. In some embodiments, one or more nitric oxide permeable layers 114 may be configured to enclose one or more photolyzable nitric oxide donors 108. In some embodiments, one or more nitric oxide permeable layers 114 may be configured to enclose one or more light sources 106. In some embodiments, one or more nitric oxide permeable layers 114 may be configured to enclose one or more photolyzable nitric oxide donors 108 and one or more light sources 106. In some embodiments, one or more nitric oxide permeable layers 114 may be configured to enclose one or more photolyzable nitric oxide donors 108, one or more light sources 106, and one or more control units 110. In some embodiments, one or more nitric oxide permeable layers 114 may be configured to enclose one or more photolyzable nitric oxide donors 108, one or more light sources 106, one or more control units 110, and one or more electromagnetic receivers 116. In some embodiments, one or more nitric oxide permeable layers 114 may be configured to enclose one or more photolyzable nitric oxide donors 108, one or more light sources 106, one or more control units 110, one or more electromagnetic receivers 116, or substantially any combination thereof.

Nitric oxide permeable layers 114 may be constructed of numerous types of materials and combinations of materials. Examples of such materials include, but are not limited to, ceramics, polymeric materials, metals, plastics, and the like. In some embodiments, nitric oxide permeable layers 114 may include numerous combinations of materials. For example, in some embodiments, a nitric oxide permeable layer 114 may include a nitric oxide impermeable material that is coupled to a nitric oxide permeable material. In some embodiments, a nitric oxide permeable layer 114 may include one or more nitric oxide permeable membranes (e.g., U.S. Patent Application No. 20020026937). In some embodiments, a nitric oxide permeable layer 114 may include a selectively permeable membrane. For example, in some embodiments, a nitric oxide permeable layer 114 may include a selectively permeable membrane that is a hydrophilic polyester co-polymer membrane system that includes a copolymer with 70% polyester and 30% polyether (e.g., Sympatex™ 10 μm membrane, see Hardwick et al., Clinical Science, 100:395-400 (2001)). In some embodiments, a nitric oxide permeable layer 114 may include a scintered glass portion that is permeable to nitric oxide. Accordingly, nitric oxide permeable layers 114 may include numerous types of porous ceramics that are permeable to nitric oxide. In some embodiments, a nitric oxide permeable layer 114 may include a porous metal portion that is permeable to nitric oxide. In some embodiments, a nitric oxide permeable layer 114 may include a nitric oxide permeable coating (e.g., U.S. Patent Application Nos. 20050220838 and 20030093143).

Sensor

Numerous types of sensors 112 may be used within system 100. In some embodiments, one or more sensors 112 may be used to determine the presence of nitric oxide in one or more tissues. In some embodiments, a sensor 112 may be configured for use on the outside surface of an individual 130. For example, in some embodiments, one or more sensors 112 may be configured to detect the concentration of nitric oxide on the surface of skin, a wound, a surface of a table, and the like. In some embodiments, one or more sensors 112 may be configured to be included within one or more substrates 104. In some embodiments, one or more sensors 112 may be configured to be included within one or more nitric oxide permeable layers 114. In some embodiments, a sensor 112 may be configured to utilize fluorescence to detect nitric oxide. For example, in some embodiments, a sensor may detect nitric oxide through use of one or more fluorescent probes, such as 4,5-diaminofluorescein diacetate (EMD Chemicals Inc., San Diego, Calif.). In some embodiments, a sensor may detect nitric oxide through use of one or more electrodes. For example, in some embodiments, a sensor may utilize an electrode that includes a single walled carbon nanotube and an ionic liquid to detect nitric oxide (e.g., Li et al., Electroanalysis, 18:713-718 (2006)). Numerous sensors 112 are commercially available and have been described (e.g., World Precision Instruments, Inc., Sarasota, Fla., USA; U.S. Pat. Nos. 6,100,096; 6,280, 604; 5,980,705). In some embodiments, a sensor 112 may include one or more transmitters. In some embodiments, a sensor 112 may include one or more receivers. In some embodiments, a sensor 112 may be configured to transmit one or more signals 122. In some embodiments, a sensor 112 may be configured to receive one or more signals 122. Many types of sensors may be used within system 100. Examples of such sensors include, but are not limited to, temperature sensors 112, pressure sensors 112 (e.g., blood pressure, hydrostatic pressure), pulse rate sensors 112, clocks, bacterial contamination sensors 112, strain sensors 112, light sensors 112, nitric oxide sensors 112, and the like.

Electromagnetic Receiver

Numerous types of electromagnetic receivers 116 may be used within system 100. In some embodiments, one or more electromagnetic receivers 116 may be used to electromagnetically couple power to energize one or more light sources 106 from an external power supply. Methods to construct such electromagnetic receivers 116 have been described (e.g., U.S. Pat. No. 5,571,152). Briefly, in some embodiments, one or more electromagnetic receivers 116 may be associated with one or more rectifier chips. The one or more electromagnetic receivers 116 may include one or more cores about which are wrapped an electrical conductor. In some embodiments, cores may comprise a material, such as a ferrite material, due to its relatively high magnetic permeability and low magnetic hysteresis. However, other materials can be used for this purpose. In some embodiments, the electromagnetic receiver 116 may be operably coupled to a light emitting diode.

Electromagnetic Transmitter

Numerous types of electromagnetic transmitters 120 may be used within system 100. Methods to construct electromagnetic transmitters 120 have been described (e.g., U.S. Pat. No. 5,571,152). Briefly, in some embodiments, the electromagnetic transmitter 120 may include a ferrite core around which is wrapped an electrical conductor. Other types of material having high magnetic permeability and relatively low magnetic hysteresis may be used for the core. Insulating tape may be wrapped around the electrical conductor, or the electromagnetic transmitter 120 may be dipped in a resin to form a coating that stabilizes and fixes the electrical conductor on the core. A return lead from one end of the electrical conductor may include one of two leads that are coupled to an AC power supply.

Electromagnetic Energy

Electrical power may be electromagnetically coupled from one or more electromagnetic transmitters 120 with one or more electromagnetic receivers 116. Accordingly, electrical power that is transferred to the one or more electromagnetic receivers 116 may be used to power one or more operably linked light emitters. Methods and devices that may be used to transmit electrical power to a light emitter have been described (e.g., U.S. Pat. No. 5,571,152).

Management Unit

In some embodiments, system 100 may include one or more management units 126. In some embodiments, a management unit 126 may be configured as a computer. Accordingly, in some embodiments, a management unit 126 may be configured to accept input and provide output. For example, in some embodiments, a management unit 126 may receive one or more signals 122 from one or more sensors 112, process the one or more signals 122, and then transmit one or more signals 122. In some embodiments, one or more transmitted signals 122 may be received by one or more control units 110. In some embodiments, one or more transmitted signals 122 may be received by one or more light sources 106. Accordingly, in some embodiments, a management unit 126 may be configured to manage nitric oxide production by an apparatus 102. For example, in some embodiments, a management unit 126 may include and execute a set of instructions for the operation of one or more control units 110 that facilitate production of nitric oxide by one or more apparatuses 102 at preselected times and for preselected concentrations. In some embodiments, such production may be regulated through control of the intensity of light emitted by one or more light sources 106, the duration of light emitted by one or more light sources 106, the frequency of light emitted by one or more light sources 106, and the like. In some embodiments, a management unit 126 may dynamically control the production of nitric oxide by one or more devices. For example, in some embodiments, a management unit 126 may be configured to maintain a nitric oxide concentration within a range of concentrations. Accordingly, the management unit 126 may receive one or more signals 122 from one or more sensors 112 indicating a current concentration of nitric oxide. The management unit 126 may then determine if the nitric oxide concentration is within a range of nitric oxide concentrations or out of a range of nitric oxide concentrations and then increase nitric oxide production, decrease nitric oxide production, or maintain nitric oxide production to cause the nitric oxide concentration to be maintained within a range. Accordingly, a management unit 126 may be used in numerous ways to regulate nitric oxide production.

Transmitter

The system 100 may include one or more transmitters. In some embodiments, one or more transmitters may be operably coupled to one or more sensors 112. In some embodiments, one or more transmitters may be operably coupled to one or more management units 126. In some embodiments, one or more transmitters may be operably coupled to one or more control units 110. In some embodiments, one or more transmitters may be operably coupled to one or more sensors 112, one or more control units 110, one or more management units 126, or substantially any combination thereof. Numerous types of transmitters may be used in association with system 100. Examples of such transmitters include, but are not limited to, transmitters that transmit one or more optical signals 122, radio signals 122, wireless signals 122, hardwired signals 122, infrared signals 122, ultrasonic signals 122, and the like (e.g., U.S. Pat. Nos. RE39,785; 7,260,768; 7,260,764; 7,260,402; 7,257,327; 7,215,887; 7,218,900; herein incorporated by reference). In some embodiments, one or more transmitters may transmit one or more signals 122 that are encrypted. Numerous types of transmitters are known and have been described (e.g., U.S. Pat. Nos. and Published U.S. patent applications: U.S. Pat. Nos. 7,236,595; 7,260,155; 7,227,956; US2006/0280307; herein incorporated by reference).

Signal

Numerous types of signals 122 may be used in association with system 100. Examples of such signals 122 include, but are not limited to, optical signals 122, radio signals 122, wireless signals 122, hardwired signals 122, infrared signals 122, ultrasonic signals 122, and the like.

In some embodiments, one or more signals 122 may not be encrypted. In some embodiments, one or more signals 122 may be encrypted. In some embodiments, one or more signals 122 may be sent through use of a secure mode of transmission. In some embodiments, one or more signals 122 may be coded for receipt by a specific individual 130. In some embodiments, such code may include anonymous code that is specific for an individual 130. Accordingly, information included within one or more signals 122 may be protected against being accessed by others who are not the intended recipient.

Receiver

System 100 may include one or more receivers. In some embodiments, one or more receivers may be operably coupled to one or more sensors 112. In some embodiments, one or more receivers may be operably coupled to one or more management units 126. In some embodiments, one or more receivers may be operably coupled to one or more control units 110. In some embodiments, one or more receivers may be operably coupled to one or more sensors 112, one or more control units 110, one or more management units, or substantially any combination thereof. Numerous types of receivers may be used in association with system 100. Examples of such receivers include, but are not limited to, receivers that receive one or more optical signals 122, radio signals 122, wireless signals 122, hardwired signals 122, infrared signals 122, ultrasonic signals 122, and the like. Such receivers are known and have been described (e.g., U.S. Pat. Nos. RE39,785; 7,218,900; 7,254,160; 7,245,894; 7,206,605; herein incorporated by reference).

User Interface/User

System 100 may include numerous types of user interfaces 128. For example, one or more users (e.g., individuals 130) may interact through use of numerous user interfaces 128 that utilize hardwired methods, such as through use of an on/off switch, a push button, a keyboard, and the like. In some embodiments, the user interface 128 may utilize wireless methods, such as methods that utilize a transmitter and receiver, utilize the internet, and the like.

Individual

An apparatus 102 may be used to deliver nitric oxide to an individual 130. In some embodiments, an individual 130 may be a human. In some embodiments, an individual 130 may be a human male. In some embodiments, an individual 130 may be a human female. An apparatus 102 may be used within numerous contexts. For example, in some embodiments, an apparatus 102 may be used to deliver nitric oxide to an individual 130 to treat sexual dysfunction. In some embodiments, an apparatus 102 may be used to treat female arousal disorder. In some embodiments, an apparatus 102 may be used to treat male erectile disorder. In some embodiments, sexual dysfunction may be due to a physical condition. For example, in some embodiments, sexual dysfunction may result from surgery, a physical injury, pharmaceutical use, age, or the like. In some embodiments, sexual dysfunction may be due to a mental condition. For example, in some embodiments, sexual dysfunction may be due to depression, lack of interest, insecurity, anxiety, or the like. In some embodiments, an apparatus 102 may deliver nitric oxide to increase sexual performance and/or pleasure. In some embodiments, an apparatus 102 may be used to deliver nitric oxide to the skin of an individual 130. In some embodiments, such delivery may be for cosmetic purposes. In some embodiments, such delivery may be for therapeutic purposes. For example, in some embodiments, an apparatus 102 may be used to deliver nitric oxide to a skin lesion, such as a skin ulcer, a burn, a cut, a puncture, a laceration, a blunt trauma, an acne lesion, a boil, and the like. In some embodiments, an apparatus 102 may be used to deliver nitric oxide to a skin surface to increase the expression of endogenous collagenase. In some embodiments, an apparatus 102 may be used to deliver nitric oxide to a skin surface to regulate the formation of collagen. In some embodiments, an apparatus 102 may be used to deliver nitric oxide to reduce inflammation (e.g., reduce exudate secretion) at the site of a lesion (e.g., U.S. Patent Application No. 2007/0088316). In some embodiments, an apparatus 102 may be used to deliver nitric oxide to reduce the microbial burden within a wound site. For example, in some embodiments, an apparatus 102 may be used to deliver nitric oxide as an antibacterial agent against methicillin-resistant *Staphylococcus aureus*. An apparatus 102 may deliver nitric oxide to an individual 130 at numerous concentrations. For example, in some embodiments, nitric oxide may be delivered at a concentration ranging from about 160 ppm to about 400 ppm. Such concentrations may be used without inducing toxicity in the healthy cells around a wound site (e.g., U.S. Patent Application No. 2007/0088316).

Figure 2:
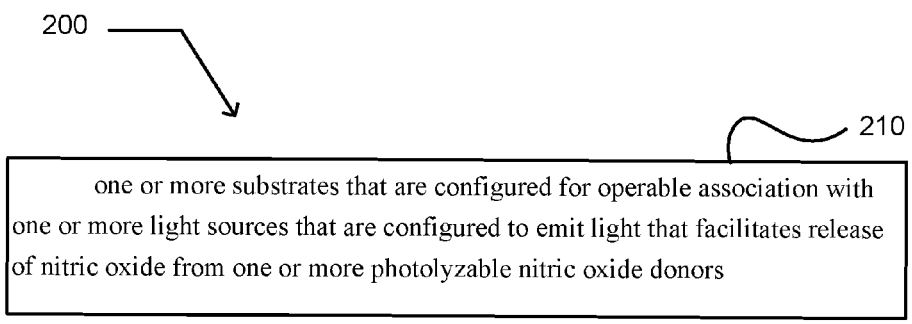
FIG. 2 illustrates embodiment 200 of apparatus 102 within system 100.

FIG. 2 illustrates embodiment 200 of an apparatus 102 within system 100. In FIG. 2, discussion and explanation may be provided with respect to the above-described example of FIG. 1, and/or with respect to other examples and contexts. However, it should be understood that the modules may execute operations in a number of other environments and contexts, and/or modified versions of FIG. 1. Also, although the various modules are presented in the sequence(s) illustrated, it should be understood that the various modules may be configured in numerous orientations.

The embodiment 200 may include module 210 that includes one or more substrates that are configured for operable association with one or more light sources that are configured to emit light that facilitates release of nitric oxide from one or more photolyzable nitric oxide donors. In some embodiments, apparatus 102 may include one or more substrates 104 that are configured for operable association with one or more light sources 106 that are configured to emit light that facilitates release of nitric oxide from one or more photolyzable nitric oxide donors 108. A substrate 104 may be made of numerous materials and combinations of materials. Examples of such materials include, but are not limited to, metals, metal alloys, polymers, copolymers, ceramics, cloth, fabric, and the like. Substrates 104 may be configured in numerous ways. For example, in some embodiments, a substrate 104 may be one or more sheets of one or more materials to which one or more light sources 106 may be associated. In some embodiments, a substrate 104 may be configured to accept one or more light sources 106. For example, in some embodiments, a substrate 104 may include electrical connections that may be operably coupled to one or more light sources 106. In some embodiments, a substrate 104 may be configured to be associated with one or more power supplies. For example, in some embodiments, one or more substrates 104 may be configured to associate with one or more solar cells. In some embodiments, one or more substrates 104 may be configured to associate with one or more batteries (e.g., thin-film batteries). In some embodiments, one or more substrates 104 may be configured to associate with one or more capacitors.

Numerous techniques may be used to fabricate a substrate 104. In some embodiments, a substrate 104 may be fabricated through use of methods used in the computer industry to fabricate circuit boards and/or computer chips. For example, in some embodiments, techniques such as masking and photolithography may be used to fabricate a substrate 104. In some embodiments, circuitry may be printed onto a substrate 104. For example, in some embodiments, circuitry may be sprayed onto a substrate 104 through use of inkjet printing technology. In some embodiments, a substrate 104 may be fabricated through lamination techniques. For example, in some embodiments, one or more electrical connectors may be stamped and/or laminated onto a substrate 104. In some embodiments, laser etching may be used to fabricate a substrate 104. Accordingly, numerous techniques may be used to fabricate one or more substrates 104 that are configured to associate with one or more light sources 106 that are configured to emit light that facilitates release of nitric oxide from one or more photolyzable nitric oxide donors 108.

In some embodiments, a substrate 104 may be configured to be associated with one or more nitric oxide donors. In some embodiments, a substrate 104 may be configured to be associated with one or more photolyable nitric oxide donors 108. In some embodiments, one or more photolyable nitric oxide donors 108 may be sprayed onto one or more substrates 104. In some embodiments, one or more photolyzable nitric oxide donors 108 may be sprayed onto one or more substrates 104. In some embodiments, one or more photolyable nitric oxide donors 108 may be rolled onto one or more substrates 104. In some embodiments, one or more photolyzable nitric oxide donors 108 may be rolled onto one or more substrates 104. In some embodiments, one or more photolyable nitric oxide donors 108 may be chemically coupled to one or more substrates 104. In some embodiments, one or more photolyzable nitric oxide donors 108 may be chemically coupled to one or more substrates 104.

Substrates 104 may exhibit numerous physical characteristics. For example, in some embodiments, substrates 104 may be elastomeric. Methods to prepare elastomeric materials are known and have been reported (e.g., U.S. Pat. Nos. 6,639,007; 6,673,871; 7,105,607). In some embodiments, substrates 104 may be inelastic. For example, in some embodiments, a substrate 104 may be fabricated from one or more metal foils. In some embodiments, substrates 104 may be fabricated with pressure sensitive fibers. For example, in some embodiments, a substrate 104 may include one or more elastomeric materials that self-adhere. Accordingly, in some embodiments, a substrate 104 may be configured in the form of self-adhering athletic tape. In some embodiments, a substrate 104 may include one or more adhesives that are applied to one or more portions of the substrate 104. Accordingly, substrates 104 may be fabricated in numerous configurations.

Figure 3:
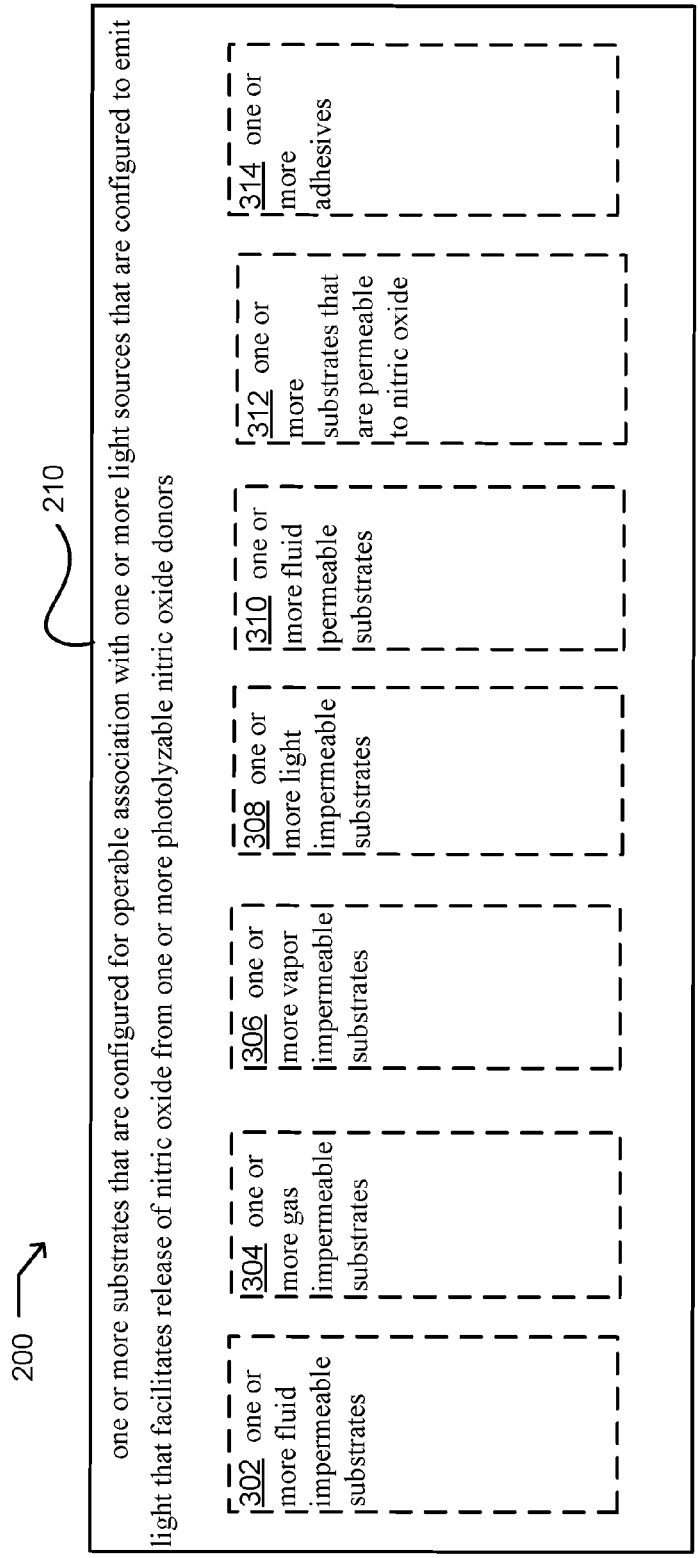
FIG. 3 illustrates alternate embodiments of module 210 of embodiment 200 of apparatus 102 within system 100.

FIG. 3 illustrates alternative embodiments of embodiment 200 of an apparatus 102 within system 100 of FIG. 2. FIG. 3 illustrates example embodiments of module 210 of an apparatus 102. Additional embodiments may include an embodiment 302, an embodiment 304, an embodiment 306, an embodiment 308, an embodiment 310, an embodiment 312, and/or an embodiment 314.

At embodiment 302, module 210 may include one or more fluid impermeable substrates. In some embodiments, one or more substrates 104 may include one or more fluid impermeable substrates 104. Numerous materials may be used to fabricate fluid impermeable substrates 104. Examples of such materials include, but are not limited to, polycarbonates, polystyrenes, latex, metals, ceramics, wood, metal alloys, and the like. Fluid impermeable substrates 104 may be configured in numerous ways. Examples of such configurations include, but are not limited to, clothing and/or protective gear (e.g., hoods, gloves, socks, shirts, pants, condoms, penile sleeves, etc.), surgical drapes, tape, bell jars, and the like. In some embodiments, one or more substrates 104 may be selectively permeable. For example, in some embodiments, one or more substrates 104 may be fluid impermeable and vapor permeable. In some embodiments, a substrate 104 may include a hydrophilic polyester co-polymer membrane system that includes a copolymer with 70% polyester and 30% polyether that is nitric oxide permeable (e.g., Sympatex™ 10 µM membrane, see Hardwick et al., Clinical Science, 100:395-400 (2001)).

At embodiment 304, module 210 may include one or more gas impermeable substrates. In some embodiments, one or more substrates 104 may include one or more gas impermeable substrates 104. Numerous materials may be used to fabricate gas impermeable substrates 104. Examples of such materials include, but are not limited to, polycarbonates, polystyrenes, latex, metals, ceramics, wood, metal alloys, and the like. Gas impermeable substrates 104 may be configured in numerous ways. Examples of such configurations include, but are not limited to, clothing and/or protective gear (e.g., hoods, gloves, socks, shirts, pants, condoms, penile sleeves, etc.), surgical drapes, tape, bell jars, and the like. In some embodiments, one or more substrates 104 that are gas impermeable may be configured to retain nitric oxide in one or more areas. For example, in some embodiments, a gas impermeable substrate 104 may be configured as a bell jar with one or more photolyzable nitric oxide donors 108 associated with the inside of the jar. Accordingly, nitric oxide released from the one or more photolyable nitric oxide donors 108 is retained within the bell jar when the open end of the bell jar is placed against a surface. In some embodiments, such configurations may be used to deliver nitric oxide to a surface. In some embodiments, one or more gas impermeable substrates 104 may be configured as an outside surface of an apparatus 102 having one or more photolyzable nitric oxide donors 108 that are associated with an inside surface of the apparatus 102 such that nitric oxide released from the one or more photolyzable nitric oxide donors 108 is blocked from passage through the gas impermeable substrate 104 For example, in some embodiments, an apparatus 102 may be configured as a sheet of material with one or more gas impermeable substrates 104 forming an outside surface of the material and one or more photolyzable nitric oxide donors 108 associated with the inside surface of the material relative to a surface to which nitric oxide is to be delivered. An example of such an apparatus 102 is a body wrap (e.g., tape) that may be wrapped around one or more surfaces of an individual 130 to which nitric oxide is to be delivered.

At embodiment 306, module 210 may include one or more vapor impermeable substrates. In some embodiments, one or more substrates 104 may include one or more vapor impermeable substrates 104. Numerous materials may be used to fabricate vapor impermeable substrates 104. Examples of such materials include, but are not limited to, polycarbonates, polystyrenes, latex, metals, ceramics, metal alloys, and the like. Vapor impermeable substrates 104 may be configured in numerous ways. In some embodiments, one or more substrates 104 that are vapor impermeable may be configured to retain water vapor in one or more areas. For example, in some embodiments, one or more vapor impermeable substrates 104 may be used to retain water vapor at a site to which nitric oxide is to be delivered. Accordingly, in some embodiments, one or more vapor impermeable substrates 104 may be configured as an outside surface of an apparatus 102 having one or more photolyzable nitric oxide donors 108 that are associated with an inside surface of the apparatus 102 such that water vapor is blocked from passage through the vapor impermeable substrate 104. For example, in some embodiments, an apparatus 102 may be configured as a sheet of material with one or more vapor impermeable substrates 104 forming an outside surface of the material and one or more photolyzable nitric oxide donors 108 associated with the inside surface of the material relative to a surface to which nitric oxide is to be delivered. An example of such an apparatus 102 is a body wrap (e.g., tape) that may be wrapped around one or more surfaces of an individual 130 to which nitric oxide is to be delivered.

At embodiment 308, module 210 may include one or more light impermeable substrates. In some embodiments, one or more substrates 104 may include one or more light impermeable substrates 104. Numerous materials may be used to fabricate light impermeable substrates 104. In some embodiments, one or more substrates 104 may be selectively light impermeable. For example, in some embodiments, one or more substrates 104 may be impermeable to light that facilitates photolysis of one or more photolyzable nitric oxide donors 108. In some embodiments, one or more substrates 104 may be impermeable to ultraviolet light. In some embodiments, one or more substrates 104 may be selectively impermeable to light that causes damage to tissue.

At embodiment 310, module 210 may include one or more fluid permeable substrates. In some embodiments, one or more substrates 104 may include one or more fluid permeable substrates 104. Fluid permeable substrates 104 may be fabricated from numerous types of materials. In some embodiments, such substrates 104 may include porous materials. In some embodiments, such substrates 104 may include perforated materials. In some embodiments, such substrates 104 may include materials into which channels are cut. In some embodiments, such substrates 104 may include capillaries and the like. In some embodiments, one or more fluid permeable substrates 104 may be included within a portion of apparatus 102. For example, in some embodiments, an apparatus 102 may include one or more fluid permeable substrates 104 to facilitate movement of one or more fluids through apparatus 102. In some embodiments, one or more fluid permeable substrates 104 may be configured to facilitate translocation of one or more photolyzable nitric oxide donors 108 that are associated with one or more fluids. For example, in some embodiments, one or more fluid permeable substrates 104 may be configured to deliver one or more fluids to the surface of an individual 130. In some embodiments, one or more fluid permeable substrates 104 may include one or more fluid reservoirs and be configured to facilitate translocation of one or more fluids. For example, in some embodiments, one or more fluid permeable substrates 104 may include one or more reservoirs and one or more channels that are configured to deliver one or more photolyzable nitric oxide donors 108 in fluid form to one or more sites.

At embodiment 312, module 210 may include one or more substrates that are permeable to nitric oxide. In some embodiments, substrate 104 may include one or more substrates 104 that are permeable to nitric oxide. A substrate 104 may include nitric oxide permeable substrates 104 that are fabricated from numerous types of material. Examples of such materials include, but are not limited to, ceramics, polymeric materials, metals, plastics, and the like. In some embodiments, substrates that are permeable to nitric oxide may include numerous combinations of materials. For example, in some embodiments, a substrate 104 that is permeable to nitric oxide may include a nitric oxide impermeable material that is coupled to a nitric oxide permeable material. In some embodiments, a substrate 104 that is permeable to nitric oxide may include one or more nitric oxide permeable membranes (e.g., U.S. Patent Application No. 20020026937). In some embodiments, a substrate 104 that is permeable to nitric oxide may include a selectively permeable membrane. For example, in some embodiments, a substrate 104 that is permeable to nitric oxide may include a selectively permeable membrane that is a hydrophilic polyester co-polymer membrane system that includes a copolymer with 70% polyester and 30% polyether (e.g., Sympatex™ 10 µm membrane, see Hardwick et al., Clinical Science, 100:395-400 (2001)). In some embodiments, a substrate 104 that is permeable to nitric oxide may include a scintered glass portion that is permeable to nitric oxide. Accordingly, a substrate 104 that is permeable to nitric oxide may include numerous types of porous ceramics that are permeable to nitric oxide. In some embodiments, a substrate 104 that is permeable to nitric oxide may include a porous metal portion that is permeable to nitric oxide. In some embodiments, a substrate 104 that is permeable to nitric oxide may include a nitric oxide permeable coating (e.g., U.S. Patent Application Nos. 20050220838 and 20030093143).

Nitric oxide permeable substrates 104 may be configured for application to an individual 130. Nitric oxide permeable substrates 104 may be configured to facilitate application of nitric oxide to a surface. In some embodiments, one or more nitric oxide permeable substrates 104 may be configured to facilitate application of nitric oxide to one or more surfaces of an individual 130. For example, in some embodiments, one or more nitric oxide permeable substrates 104 may be configured as a sheet that may be positioned on a skin surface of an individual 130 to deliver nitric oxide to the skin surface. In some embodiments, a nitric oxide permeable substrate 104 may be configured as a wearable article (e.g., hats, gloves, mittens, pants, shirts, hoods, patches, tapes, wraps, and the like). In some embodiments, nitric oxide permeable substrate 104 may be configured as one or more bags. For example, in some embodiments, one or more nitric oxide permeable substrates 104 may be included within a bag and/or sleeve that is configured to deliver nitric oxide to an individual 130.

In some embodiments, one or more nitric oxide permeable substrates 104 may be configured to enclose at least a portion of one or more photolyzable nitric oxide donors 108. In some embodiments, one or more nitric oxide permeable substrates 104 may be configured to enclose at least a portion of one or more light sources 106, at least a portion of one or more control units 110, at least a portion of one or more sensors 112, at least a portion of one or more electromagnetic receivers 116, or substantially any combination thereof.

At embodiment 314, module 210 may include one or more adhesives. In some embodiments, one or more substrates 104 may include one or more adhesives. In some embodiments, one or more substrates 104 may be configured for adherence to one or more surfaces. Accordingly, in some embodiments, one or more apparatuses 102 may include one or more substrates 104 that include one or more portions that are coated with one or more adhesives to facilitate placement of the one or more apparatuses 102 onto one or more surfaces. For example, in some embodiments, an apparatus 102 may be configured to include one or more adhesives that facilitate placement of the apparatus 102 over a skin lesion and/or wound on an individual 130.

FIG. 4 illustrates alternative embodiments of embodiment 200 of an apparatus 102 within system 100 of FIG. 2. FIG. 4 illustrates example embodiments of module 210 of an apparatus 102. Additional embodiments may include an embodiment 402, an embodiment 404, an embodiment 406, an embodiment 408, an embodiment 410, an embodiment 412, an embodiment 414, and/or an embodiment 416.

At embodiment 402, module 210 may include one or more flexible substrates. In some embodiments, one or more substrates 104 may include one or more flexible substrates 104. In some embodiments, all portions of a substrate 104 may be flexible. In some embodiments, one or more portions of a substrate 104 may be flexible. For example, in some embodiments, a substrate 104 may include one or more inflexible portions and one or more flexible portions. In some embodiments, an apparatus 102 may include one or more substrates 104 that include one or more inflexible portions that are configured to create a closed space above a surface without contacting the surface and one or more substrates 104 that include one or more flexible portions that allow the apparatus 102 to be adhered to the surface. For example, in some embodiments, an apparatus 102 may include an inflexible substrate 104 that is shaped like a bell jar to facilitate delivery of nitric oxide to a surface and a flexible substrate 104 that facilitates adhesion of the apparatus 102 to the surface to which nitric oxide is to be delivered. Accordingly, a flexible substrate 104 may be configured in numerous ways.

At embodiment 404, module 210 may include one or more inflexible substrates. In some embodiments, one or more substrates 104 may include one or more inflexible substrates 104. In some embodiments, all portions of a substrate 104 may be inflexible. In some embodiments, one or more portions of a substrate 104 may be inflexible. For example, in some embodiments, a substrate 104 may include one or more inflexible portions and one or more flexible portions. In some embodiments, an apparatus 102 may include one or more substrates 104 that include one or more inflexible portions that are configured to create a closed space above a surface without contacting the surface and one or more substrates 104 that include one or more flexible portions that allow the apparatus 102 to be adhered to the surface. For example, in some embodiments, an apparatus 102 may include an inflexible substrate 104 that is shaped like a bell jar to facilitate delivery of nitric oxide to a surface and a flexible substrate 104 that facilitates adhesion of the apparatus 102 to the surface to which nitric oxide is to be delivered. Accordingly, a flexible substrate 104 may be configured in numerous ways.

At embodiment 406, module 210 may include one or more metallic substrates. In some embodiments, one or more substrates 104 may include one or more metallic substrates 104. In some embodiments, a substrate 104 may be entirely constructed with one or more metallic materials. For example, in some embodiments, a substrate 104 may be a metal foil. In some embodiments, a substrate 104 may be partially constructed with one or more metallic materials. For example, in some embodiments, a substrate 104 may include one or more portions that are metallic and one or more portions that are non-metallic. In some embodiments, a substrate 104 may include metallic portions that are configured as one or more electrical connections. In some embodiments, a substrate 104 may include metallic portions that include one or more electrical connections that are configured to associate with one or more light sources 106. In some embodiments, a substrate 104 may include metallic portions that include one or more electrical connections that are configured to associate with one or more sensors 112. In some embodiments, a substrate 104 may include metallic portions that include one or more electrical connections that are configured to associate with one or more control units 110. In some embodiments, a substrate 104 may include metallic portions that may be coupled to one or more nitric oxide donors that release nitric oxide in response to electrical current (e.g., Hou et al., Chem. Commun., 1831-1832 (2000)).

At embodiment 408, module 210 may include one or more non-metallic substrates. In some embodiments, one or more substrates 104 may include one or more non-metallic substrates 104. In some embodiments, a substrate 104 may be entirely constructed with one or more non-metallic materials. For example, in some embodiments, a substrate 104 may be a plastic sheet. In some embodiments, a substrate 104 may be partially constructed with one or more non-metallic materials. For example, in some embodiments, a substrate 104 may include one or more portions that are non-metallic and one or more portions that are metallic. In some embodiments, a substrate 104 may include one or more non-metallic portions that are configured as insulators for one or more metallic portions that are configured as electrical connections. Accordingly, in some embodiments, a substrate 104 may include one or more non-metallic portions and one or more metallic portions that are configured as one or more electrical connections that may associate with one or more light sources 106, one or more sensors 112, one or more control units 110, or substantially any combination thereof.

At embodiment 410, module 210 may include one or more polymeric substrates. In some embodiments, one or more substrates 104 may include one or more polymeric substrates 104. Numerous types of polymers may be used to fabricate one or more substrates 104. Examples of such polymers include, but are not limited to, polyethylene, polypropylene, block-copolymers, polycarbonate, polystyrene, and the like.

At embodiment 412, module 210 may include one or more gas permeable substrates. In some embodiments, one or more substrates 104 may include one or more gas permeable substrates 104. Gas permeable substrates 104 may be fabricated from numerous types of materials. In some embodiments, such substrates 104 may include porous materials. In some embodiments, such substrates 104 may include perforated materials. In some embodiments, such substrates 104 may include materials into which channels are cut. In some embodiments, such substrates 104 may include capillaries and the like. In some embodiments, one or more gas permeable substrates 104 may be included within a portion of apparatus 102. For example, in some embodiments, an apparatus 102 may include one or more gas permeable substrates 104 to facilitate movement of one or more gases through apparatus 102. In some embodiments, one or more gas permeable substrates 104 may be configured to facilitate translocation of nitric oxide. For example, in some embodiments, one or more gas permeable substrates 104 may be configured to deliver nitric oxide to the surface of an individual 130.

At embodiment 414, module 210 may include one or more vapor permeable substrates. In some embodiments, one or more substrates 104 may include one or more vapor permeable substrates 104. In some embodiments, a vapor permeable substrate 104 may be selectively permeable. For example, in some embodiments, a vapor permeable substrate 104 may be permeable to vapor but impermeable to fluid. In some embodiments, an apparatus 102 may include one or more portions that include one or more vapor permeable substrates 104 that facilitate release of water vapor. For example, in some embodiments, an apparatus 102 may be a body wrap that is configured to deliver nitric oxide to the surface of an individual 130 and to facilitate release of perspiration from the surface of the individual's 130 skin.

At embodiment 416, module 210 may include one or more light permeable substrates. In some embodiments, one or more substrates 104 may include one or more light permeable substrates 104. In some embodiments, one or more substrates 104 may include one or more selectively light permeable substrates 104. For example, in some embodiments, one or more substrates 104 may be selected to be permeable to light that does not facilitate release of nitric oxide from one or more photolyzable nitric oxide donors 108. In some embodiments, one or more substrates 104 may be selected to be permeable to light that facilitates release of nitric oxide from one or more photolyzable nitric oxide donors 108.

FIG. 5 illustrates alternative embodiments of embodiment 200 of an apparatus 102 within system 100 of FIG. 2. FIG. 5 illustrates example embodiments of module 210 of an apparatus 102. Additional embodiments may include an embodiment 502, an embodiment 504, an embodiment 506, and/or an embodiment 508.

At embodiment 502, module 210 may include one or more sensors. In some embodiments, one or more substrates 104 may include one or more sensors 112. In some embodiments, one or more sensors 112 may be integrated within one or more substrates 104. In some embodiments, one or more sensors 112 may be associated with one or more surfaces of one or more substrates 104. In some embodiments, one or more sensors 112 may be associated with one or more electrical connections associated with one or more substrates 104. Numerous types of sensors 112 may be associated with one or more substrates 104. Examples of such sensors 112 include, but are not limited to, temperature sensors 112, pressure sensors (e.g., blood pressure, hydrostatic pressure), pulse rate sensors 112, clocks, bacterial contamination sensors 112, strain sensors 112, light sensors 112, and the like.

At embodiment 504, module 210 may include one or more sensors that are configured to detect nitric oxide. In some embodiments, one or more substrates 104 may include one or more sensors 112 that are configured to detect nitric oxide. In some embodiments, one or more sensors 112 may be integrated within one or more substrates 104. In some embodiments, one or more sensors 112 may be associated with one or more surfaces of one or more substrates 104. In some embodiments, one or more sensors 112 may be associated with one or more electrical connections associated with one or more substrates 104. In some embodiments, a sensor 112 that is configured to detect nitric oxide may be configured for use on the outside surface of an individual 130. For example, in some embodiments, one or more sensors 112 that are configured to detect nitric oxide may be configured to detect the concentration of nitric oxide on the surface of skin, a wound, a surface of a table, and the like. In some embodiments, a sensor 112 that is configured to detect nitric oxide may be configured to utilize fluorescence to detect nitric oxide. For example, in some embodiments, a sensor 112 may detect nitric oxide through use of one or more fluorescent probes, such as 4,5-diaminofluorescein diacetate (EMD Chemicals Inc., San Diego, Calif.). In some embodiments, a sensor 112 may detect nitric oxide through use of one or more electrodes. For example, in some embodiments, a sensor 112 may utilize an electrode that includes a single walled carbon nanotube and an ionic liquid to detect nitric oxide (e.g., Li et al., Electroanalysis, 18:713-718 (2006)). Numerous sensors 112 are commercially available and have been described (e.g., World Precision Instruments, Inc., Sarasota, Fla., USA; U.S. Pat. Nos. 6,100,096; 6,280,604; 5,980,705). In some embodiments, a sensor 112 that is configured to detect nitric oxide may include one or more transmitters. In some embodiments, a sensor 112 that is configured to detect nitric oxide may include one or more receivers. In some embodiments, a sensor 112 that is configured to detect nitric oxide may be configured to transmit one or more signals 122. In some embodiments, a sensor 112 that is configured to detect nitric oxide may be configured to receive one or more signals 122.

At embodiment 506, module 210 may include one or more sensors that are configured to detect one or more nitric oxide donors. In some embodiments, one or more substrates 104 may include one or more sensors 112 that are configured to detect one or more nitric oxide donors. In some embodiments, one or more sensors 112 may include one or more surface plasmon resonance chemical electrodes that are configured to detect one or more nitric oxide donors. For example, in some embodiments, one or more sensors 112 may include one or more surface plasmon resonance chemical electrodes that include antibodies and/or aptamers that bind to one or more nitric oxide donors. Accordingly, such electrodes may be used to detect the one or more nitric oxide donors through use of surface plasmon resonance. Methods to construct surface plasmon resonance chemical electrodes are known and have been described (e.g., U.S. Pat. No. 5,858,799; Lin et al., Applied Optics, 46:800-806 (2007)). In some embodiments, antibodies and/or aptamers that bind to one or more nitric oxide donors may be used within one or more microelectromechanical systems to detect one or more nitric oxide donors. Methods to construct microelectromechanical detectors have been described (e.g., Gau et al., Biosensors & Bioelectronics, 16:745-755 (2001)).

At embodiment 508, module 210 may include one or more sensors that are configured to detect one or more nitric oxide synthases. In some embodiments, one or more substrates 104 may include one or more sensors 112 that are configured to detect one or more nitric oxide synthases. In some embodiments, one or more sensors 112 may be configured to detect nitric oxide synthase activity. Nitric oxide synthase detection kits are commercially available (e.g., Cell Technology, Inc., Mountain View, Calif.). In some embodiments, one or more sensors 112 may be configured to detect nitric oxide synthase messenger ribonucleic acid (mRNA). Methods that may be used to detect such mRNA have been reported (e.g., Sonoki et al., Leukemia, 13:713-718 (1999)). In some embodiments, one or more sensors 112 may be configured to detect nitric oxide synthase through immunological methods. Methods that may be used to detect nitric oxide synthase directly been reported (e.g., Burrell et al., J. Histochem. Cytochem., 44:339-346 (1996) and Hattenbach et al., Ophthalmologica, 216:209-214 (2002)). In some embodiments, microelectromechanical systems may be used to detect nitric oxide synthase. In some embodiments, antibodies and/or aptamers that bind to nitric oxide synthase may be used within one or more microelectromechanical systems to detect nitric oxide synthase. Methods to construct microelectromechanical detectors have been described (e.g., Gau et al., Biosensors & Bioelectronics, 16:745-755 (2001)). Accordingly, sensors 112 may be configured in numerous ways to detect one or more nitric oxide synthases.

FIG. 6 illustrates alternative embodiments of embodiment 200 of an apparatus 102 within system 100 of FIG. 2. FIG. 6 illustrates example embodiments of module 210 of an apparatus 102. Additional embodiments may include an embodiment 602, an embodiment 604, an embodiment 606, an embodiment 608, an embodiment 610, an embodiment 612, an embodiment 614, and/or an embodiment 616.

At embodiment 602, module 210 may include one or more substrates that include one or more connections configured for operable association with the one or more light sources. In some embodiments, one or more substrates 104 may include one or more substrates 104 that include one or more connections configured for operable association with the one or more light sources 106. In some embodiments, one or more substrates 104 may include one or more plug-in connectors that are configured to associate with one or more light sources 106. In some embodiments, the one or more plug-in connectors may be coupled to one or more conductors (e.g., wires, sheets, circuit boards, etc.) that may be associated with one or more power supplies, sensors 112, control units 110, and the like. In some embodiments, one or more substrates 104 may include one or more solder points where one or more light sources 106 may be soldered into place. For example, in some embodiments, a substrate 104 may include a circuit board onto which one or more light sources 106 may be soldered. Accordingly, numerous types of connectors may be associated with one or more substrates 104.

At embodiment 604, module 210 may include one or more substrates that are configured to associate with one or more batteries. In some embodiments, one or more substrates 104 may include one or more substrates 104 that are configured to associate with one or more batteries. In some embodiments, one or more substrates 104 may include one or more connectors that are configured to associate with one or more batteries. In some embodiments, one or more substrates 104 may be fabricated with one or more materials such that one or more batteries may be laminated onto the one or more substrates 104. A substrate 104 may be configured in numerous ways to facilitate association with one or more batteries. In some embodiments, one or more substrates may be configured to associate with one or more thin-film batteries.

At embodiment 606, module 210 may include one or more substrates that are configured to associate with one or more light emitting diodes. In some embodiments, one or more substrates 104 may include one or more substrates 104 that are configured to associate with one or more light emitting diodes. In some embodiments, one or more substrates 104 may include one or more light emitting diodes within the substrate 104. For example, in some embodiments, a substrate 104 may be formed by casting the substrate 104 around one or more light emitting diodes such that the light emitting diodes are contained with the substrate 104. In some embodiments, a substrate 104 may be formed by laminating two or more layers of material together with one or more light emitting diodes between the two or more layers such that the light emitting diodes are contained with the substrate 104.

At embodiment 608, module 210 may include one or more substrates that are configured to associate with one or more nitric oxide donors. In some embodiments, one or more substrates 104 may include one or more substrates 104 that are configured to associate with one or more nitric oxide donors. In some embodiments, one or more substrates 104 may be porous such that one or more nitric oxide donors may be included within the pores of the substrate 104. In some embodiments, one or more substrates 104 may include one or more reservoirs that are configured to include one or more photolyzable nitric oxide donors 108.

At embodiment 610, module 210 may include one or more substrates that include one or more operably coupled photolyzable nitric oxide donors. In some embodiments, one or more substrates 104 may include one or more substrates 104 that include one or more operably coupled photolyzable nitric oxide donors 108. In some embodiments, one or more substrates 104 may include one or more photolyzable nitric oxide donors 108 that are chemically coupled to the one or more substrates 104.

At embodiment 612, module 210 may include one or more substrates that are configured as a sheet, a hood, a glove, a body wrap, a condom, a penile sleeve, a surgical drape, a mask, pants, a shirt, underwear, a sock, a mitten, a cap, a bag, a bed, a table, a chamber, or tape. In some embodiments, one or more substrates 104 may include one or. more substrates 104 that are configured as a sheet, a hood, a glove, a body wrap, a condom, a penile sleeve, a surgical drape, a mask, pants, a shirt, underwear, a sock, a mitten, a cap, a bag, a bed, a table, a chamber, tape, and the like.

At embodiment 614, module 210 may include one or more status indicators. In some embodiments, one or more substrates 104 may include one or more status indicators. In some embodiments, one or more substrates 104 may include one or more status indicators that indicate the concentration of one or more photolyzable nitric oxide donors 108. Accordingly, in some embodiments, one or more status indicators may be operably associated with one or more sensors 112 that detect one or more photolyzable nitric oxide donors 108. In some embodiments, one or more substrates 104 may include one or more status indicators that indicate output from one or more power supplies. Accordingly, in some embodiments, one or more status indicators may be operably associated with one or more power supplies. In some embodiments, one or more status indicators may be associated with one or more light emitters and indicate output from one or more light sources 106. Accordingly, in some embodiments, one or more status indicators may be used to indicate if a power supply, a light emitter, a photolyzable nitric oxide donor 108, or substantially any combination thereof has been diminished and/or exhausted. In some embodiments, one or more status indicators may be configured to indicate that one or more photolyzable nitric oxide donors 108 should be replaced. In some embodiments, one or more status indicators may be configured to indicate that one or more light emitters should be replaced. In some embodiments, one or more status indicators may be configured to indicate that one or more power supplies should be replaced and/or recharged. A status indicator may be configured in numerous ways. In some embodiments, a status indicator may include one or more lights. For example, in some embodiments, a status indicator that is associated with one or more sensors 112 that detect one or more photolyzable nitric oxide donors 108 may illuminate a green light to indicate and adequate amount of one or more photolyzable nitric oxide donors 108 and illuminate a red light to indicate an inadequate amount of one or more photolyzable nitric oxide donors 108. In some embodiments, a status indicator may display one or more messages on a liquid crystal display. Status indicators may be configured in numerous ways.

At embodiment 616, module 210 may include one or more control units that are configured to control one or more remote light sources. In some embodiments, one or more substrates 104 may include one or more control units 110 that are configured to control one or more remote light sources 132. In some embodiments, one or more substrates 104 may include one or more control units 110 that are configured to control one or more light sources 106 that are physically associated with the one or more substrates 104 and one or more remote light sources 132 that are not physically associated with the one or more substrates 104. For example, in some embodiments, a control unit 110 may be configured to control a remote light source 132 that emits light that facilitates release of nitric oxide from one or more photolyzable nitric oxide donors 108. In some embodiments, the one or more remote light sources 132 may include one or more external light sources (e.g., one or more remote light sources 132 that are configured for external use relative to an individual 130). Accordingly, in some embodiments, one or more control units 110 may include one or more transmitters that are configured to transmit one or more signals 122 that facilitate control of one or more remote light sources 132. In some embodiments, one or more control units 110 may be configured to receive one or more signals 122 from one or more management units 126. In some embodiments, one or more control units 110 may be configured to receive one or more signals 122 from one or more sensors 112. In some embodiments, one or more control units 110 may be configured to receive one or more signals 122 from one or more remote light sources 132. Accordingly, in some embodiments, one or more control units 110 may control one or more remote light sources 132 in response to one or more management units 126, one or more remote light sources 132, one or more sensors 112, or substantially any combination thereof.

Figure 7:
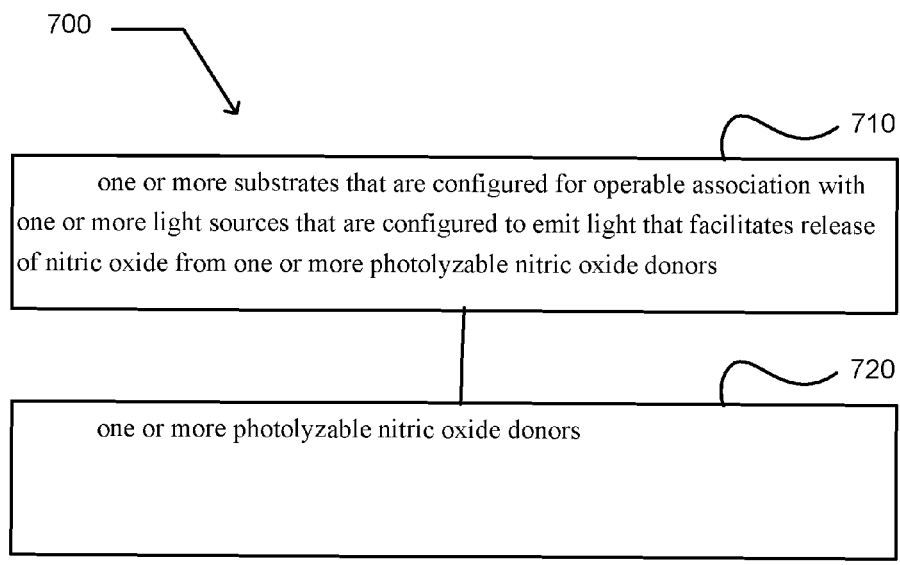
FIG. 7 illustrates embodiment 700 of apparatus 102 within system 100.

FIG. 7 illustrates embodiment 700 of an apparatus 102 within system 100. In FIG. 7, discussion and explanation may be provided with respect to the above-described example of FIG. 1, and/or with respect to other examples and contexts. In some embodiments, module 210 of FIG. 2 may correspond to module 710 as described with respect to embodiment 700 of an apparatus 102 within system 100. However, it should be understood that the modules may execute operations in a number of other environments and contexts, and/or modified versions of FIG. 1. Also, although the various modules are presented in the sequence(s) illustrated, it should be understood that the various modules may be configured in numerous orientations.

The embodiment 700 may include module 710 that includes one or more substrates that are configured for operable association with one or more light sources that are configured to emit light that facilitates release of nitric oxide from one or more photolyzable nitric oxide donors. In some embodiments, apparatus 102 may include one or more substrates 104 that are configured for operable association with one or more light sources 106 that are configured to emit light that facilitates release of nitric oxide from one or more photolyzable nitric oxide donors 108. A substrate 104 may be made of numerous materials and combinations of materials. Examples of such materials include, but are not limited to, metals, metal alloys, polymers, copolymers, ceramics, cloth, fabric, and the like. Substrates 104 may be configured in numerous ways. For example, in some embodiments, a substrate 104 may be one or more sheets of one or more materials to which one or more light sources 106 may be associated. In some embodiments, a substrate 104 may be configured to accept one or more light sources 106. For example, in some embodiments, a substrate 104 may include electrical connections that may be operably coupled to one or more light sources 106. In some embodiments, a substrate 104 may be configured to be associated with one or more power supplies. For example, in some embodiments, one or more substrates 104 may be configured to associate with one or more solar cells. In some embodiments, one or more substrates 104 may be configured to associate with one or more batteries (e.g., thin-film batteries). In some embodiments, one or more substrates 104 may be configured to associate with one or more capacitors.

Numerous techniques may be used to fabricate a substrate 104. In some embodiments, a substrate 104 may be fabricated through use of methods used in the computer industry to fabricate circuit boards and/or computer chips. For example, in some embodiments, techniques such as masking and photolithography may be used to fabricate a substrate 104. In some embodiments, circuitry may be printed onto a substrate 104. For example, in some embodiments, circuitry may be sprayed onto a substrate 104 through use of inkjet printing technology. In some embodiments, a substrate 104 may be fabricated through lamination techniques. For example, in some embodiments, one or more electrical connectors may be stamped and/or laminated onto a substrate 104. In some embodiments, laser etching may be used to fabricate a substrate 104. Accordingly, numerous techniques may be used to fabricate one or more substrates 104 that are configured to associate with one or more light sources 106 that are configured to emit light that facilitates release of nitric oxide from one or more photolyzable nitric oxide donors 108.

In some embodiments, a substrate 104 may be configured to be associated with one or more nitric oxide donors 108. In some embodiments, a substrate 104 may be configured to be associated with one or more photolyable nitric oxide donors 108. In some embodiments, one or more nitric oxide donors 108 may be sprayed onto one or more substrates 104. In some embodiments, one or more photolyzable nitric oxide donors 108 may be sprayed onto one or more substrates 104. In some embodiments, one or more photolyzable nitric oxide donors 108 may be rolled onto one or more substrates 104. In some embodiments, one or more photolyzable nitric oxide donors 108 may be rolled onto one or more substrates 104. In some embodiments, one or more photolyzable nitric oxide donors 108 may be chemically coupled to one or more substrates 104. In some embodiments, one or more photolyzable nitric oxide donors 108 may be chemically coupled to one or more substrates 104.

Substrates 104 may exhibit numerous physical characteristics. For example, in some embodiments, substrates 104 may be elastomeric. Methods to prepare elastomeric materials are known and have been reported (e.g., U.S. Pat. Nos. 6,639,007; 6,673,871; 7,105,607). In some embodiments, substrates 104 may be inelastic. For example, in some embodiments, a substrate 104 may be fabricated from one or more metal foils. In some embodiments, substrates 104 may be fabricated with pressure sensitive fibers. For example, in some embodiments, a substrate 104 may include one or more elastomeric materials that self-adhere. Accordingly, in some embodiments, a substrate 104 may be configured in the form of self-adhering athletic tape. In some embodiments, a substrate 104 may include one or more adhesives that are applied to one or more portions of the substrate 104. Accordingly, substrates 104 may be fabricated in numerous configurations.

The embodiment 700 may include module 720 that includes one or more photolyzable nitric oxide donors. In some embodiments, apparatus 102 may include one or more photolyzable nitric oxide donors 108 that release nitric oxide upon photolysis. Examples of such photolyzable nitric oxide donors 108 include, but are not limited to, diazeniumdiolates (e.g., U.S. Pat. Nos. 7,105,502; 7,122,529; 6,673,338; herein incorporated by reference), trans-[RuCl([15]aneN4)NO]+2 (Ferezin et al., Nitric Oxide, 13:170-175 (2005), Bonaventura et al., Nitric Oxide, 10:83-91 (2004)), nitrosyl ligands (e.g., U.S. Pat. No. 5,665,077; herein incorporated by reference, Chmura et al., Nitric Oxide, 15:370-379 (2005), Flitney et al., Br. J. Pharmacol., 107:842-848 (1992), Flitney et al., Br. J. Pharmacol., 117:1549-1557 (1996), Matthews et al., Br. J. Pharmacol., 113:87-94 (1994)), 6-Nitrobenzo[α]pyrene (e.g., Fukuhara et al., J. Am. Chem. Soc., 123:8662-8666 (2001)), S-nitroso-glutathione (e.g., Rotta et al., Braz. J. Med. Res., 36:587-594 (2003), Flitney and Megson, J. Physiol., 550:819-828 (2003)), S-nitrosothiols (e.g., Andrews et al., British Journal of Pharmacology, 138:932-940 (2003), Singh et al., FEBS Lett., 360:47-51 (1995)), 2-Methyl-2-nitrosopropane (e.g., Pou et al., Mol. Pharm., 46:709-715 (1994), Wang et al., Chem. Rev., 102:1091-1134 (2002)), imidazolyl derivatives (e.g., U.S. Pat. No. 5,374,710; herein incorporated by reference).

Figure 8:
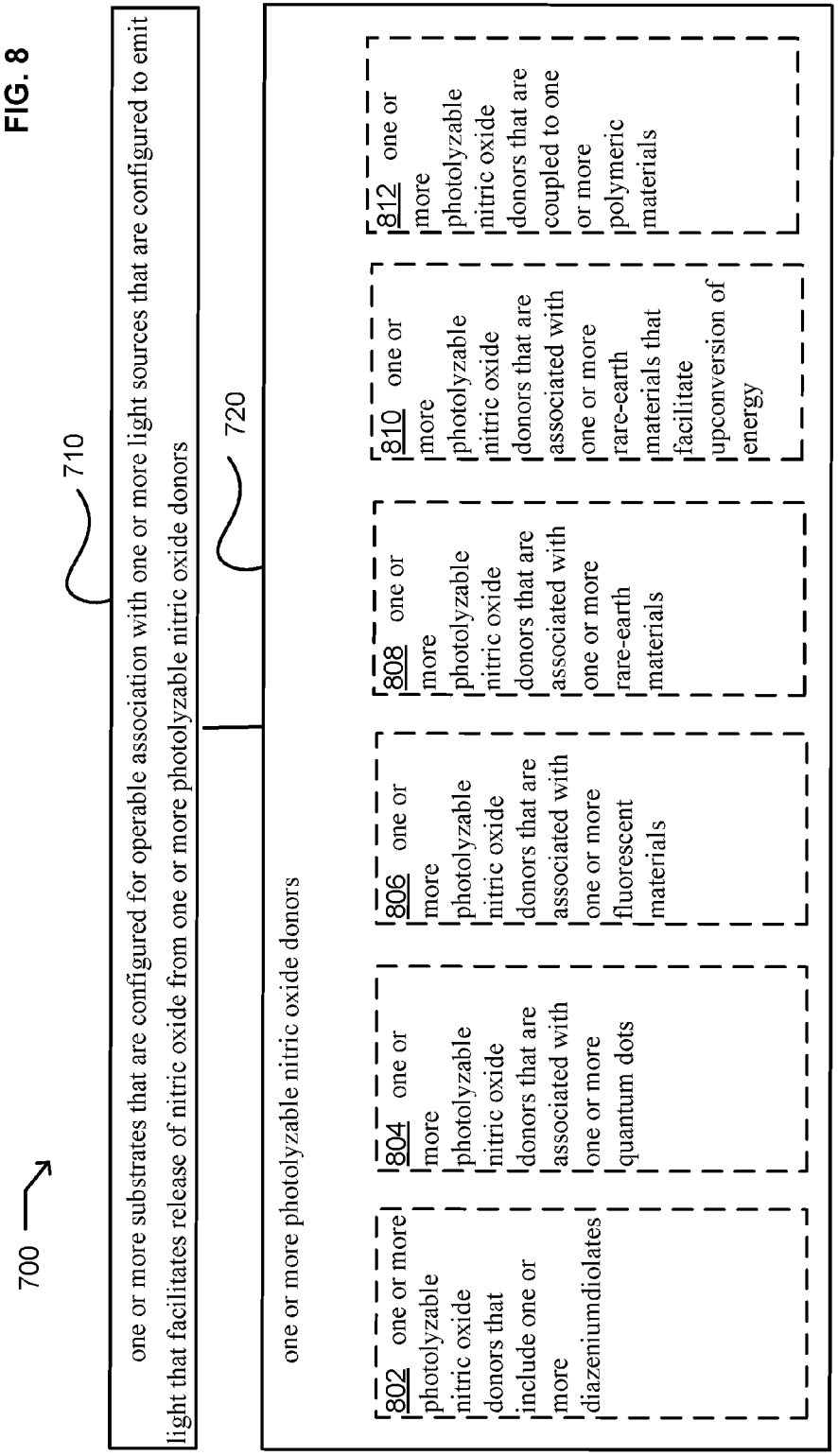
FIG. 8 illustrates alternate embodiments of module 720 of embodiment 700 of apparatus 102 within system 100.

FIG. 8 illustrates alternative embodiments of embodiment 700 of an apparatus 102 within system 100 of FIG. 7. FIG. 8 illustrates example embodiments of module 720 of an apparatus 102. Additional embodiments may include an embodiment 802, an embodiment 804, an embodiment 806, an embodiment 808, an embodiment 810, and/or an embodiment 812.

At embodiment 802, module 720 may include one or more photolyzable nitric oxide donors that include one or more diazeniumdiolates. In some embodiments, one or more photolyzable nitric oxide donors 108 may include one or more photolyzable nitric oxide donors 108 that include one or more diazeniumdiolates. Many photolyzable nitric oxide donors 108 that are diazeniumdiolates are known and have been described (e.g., U.S. Pat. No. 7,122,529). Examples of such diazeniumdiolates include, but are not limited to, $O^2$-benzyl,$O^2$-naphthylmethyl substituted diazeniumdiolates and $O^2$-naphthylallyl substituted diazeniumdiolates.

At embodiment 804, module 720 may include one or more photolyzable nitric oxide donors that are associated with one or more quantum dots. In some embodiments, one or more photolyzable nitric oxide donors 108 may include one or more photolyzable nitric oxide donors 108 that are associated with one or more quantum dots. For example, in some embodiments, one or more diazeniumdiolates may be associated with one or more quantum dots. In some embodiments, one or more quantum dots may be tuned to emit light that facilitates photolysis of one or more photolyzable nitric oxide donors 108. In some embodiments, a quantum dot may be tuned to emit light that specifically facilitates photolysis of one or more photolyzable nitric oxide donors 108. For example, in some embodiments, one or more quantum dots may emit select wavelengths of light that correspond to wavelengths of light that cause photolysis of one or more photolyzable nitric oxide donors 108. In some embodiments, one or more quantum dots may be selected that absorb light emitted by one or more light sources 106 and emit light that facilitates photolysis of one or more photolyzable nitric oxide donors 108.

At embodiment 806, module 720 may include one or more photolyzable nitric oxide donors that are associated with one or more fluorescent materials. In some embodiments, one or more photolyzable nitric oxide donors 108 may include one or more photolyzable nitric oxide donors 108 that are associated with one or more fluorescent materials. Numerous fluorescent materials may be associated with one or more photolyzable nitric oxide donors 108. Examples of such materials include, but are not limited to, 1,4-diphenylbutadiyne; 9,10-diphenylanthracene; benzene; biphenyl; ethyl-p-dimethylaminobenzoate; naphthalene; P-terphenyl; ethyl-p-dimethylaminobenzoate; stilbene; tryptophan; tyrosine; 1,2-diphenylacetylene; 7-methoxycoumarin-4-acetic acid; anthracene; indo-1; POPOP; P-quaterphenyl; pyrene; and the like.

At embodiment 808, module 720 may include one or more photolyzable nitric oxide donors that are associated with one or more rare-earth materials. In some embodiments, one or more photolyzable nitric oxide donors 108 may include one or more photolyzable nitric oxide donors 108 that are associated with one or more rare-earth materials. In some embodiments, one or more rare-earth materials may include one or more rare-earth elements. The rare-earth elements are a collection of sixteen chemical elements in the periodic table, namely scandium, yttrium, and fourteen of the fifteen lanthanoids (excluding promethium). In some embodiments, one or more rare-earth materials may include one or more rare-earth elements that fluoresce.

At embodiment 810, module 720 may include one or more photolyzable nitric oxide donors that are associated with one or more rare-earth materials that facilitate upconversion of energy. In some embodiments, one or more photolyzable nitric oxide donors 108 may include one or more photolyzable nitric oxide donors 108 that are associated with one or more rare-earth materials that facilitate upconversion of energy. In some embodiments, infrared light may be upconverted to visible light (e.g., Mendioroz et al., Optical Materials, 26:351-357 (2004)). In some embodiments, infrared light may be upconverted to ultraviolet light (e.g., Mendioroz et al., Optical Materials, 26:351-357 (2004)). In some embodiments, one or more photolyzable nitric oxide donors 108 may be associated with one or more rare-earth materials (e.g., ytterbium-erbium, ytterbium-thulium, or the like) that facilitate upconversion of energy (e.g., U.S. Pat. No. 7,088,040; herein incorporated by reference). For example, in some embodiments, one or more photolyzable nitric oxide donors 108 may be associated with $Nd^{3+}$ doped $KPb_2Cl_5$ crystals. In some embodiments, one or more photolyzable nitric oxide donors 108 may be associated with thiogallates doped with rare earths, such as $CaGa_2S_4:Ce^{3+}$ and $SrGa_2S_4:Ce^{3+}$. In some embodiments, one or more photolyzable nitric oxide donors 108 may be associated with aluminates that are doped with rare earths, such as $YAlO_3:Ce^{3+}$, $YGaO_3:Ce^{3+}$, $Y(Al,Ga)O_3:Ce^{3+}$, and orthosilicates $M_2SiO_5:Ce^{3+}$ (M:Sc, Y, Sc) doped with rare earths, such as, for example, $Y_2SiO_5:Ce^{3+}$. In some embodiments, yttrium may be replaced by scandium or lanthanum (e.g., U.S. Pat. Nos. 6,812,500 and 6,327,074; herein incorporated by reference). Numerous materials that may be used to upconvert energy have been described (e.g., U.S. Pat. Nos. 5,956,172; 5,943,160; 7,235,189; 7,215,687; herein incorporated by reference).

At embodiment 812, module 720 may include one or more photolyzable nitric oxide donors that are coupled to one or more polymeric materials. In some embodiments, one or more photolyzable nitric oxide donors 108 may include one or more photolyzable nitric oxide donors 108 that are coupled to one or more polymeric materials. For example, in some embodiments, one or more polymer matrices may be impregnated with one or more photolyzable nitric oxide donors 108 (e.g., U.S. Pat. No. 5,994,444). In some embodiments, one or more photolyzable nitric oxide donors 108 may be bound to a polymer. Methods that can be used to couple nitric oxide donors to a polymeric matrix have been reported (e.g., U.S. Pat. No. 5,405,919). In some embodiments, one or more photolyzable nitric oxide donors 108 may be coupled to polymeric materials used to produce condoms. Accordingly, in some embodiments, one or more photolyzable nitric oxide donors 108 may be coupled to a condom.

Figure 9:
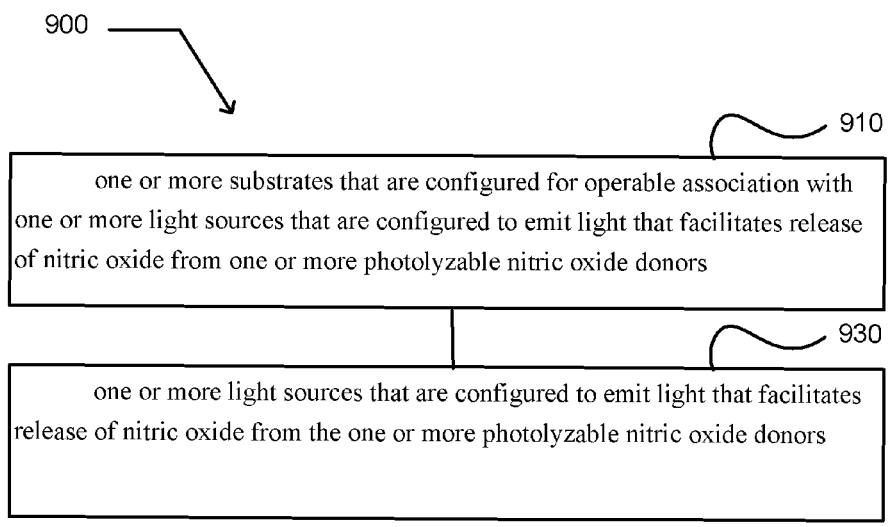
FIG. 9 illustrates embodiment 900 of apparatus 102 within system 100.

FIG. 9 illustrates embodiment 900 of an apparatus 102 within system 100. In FIG. 9, discussion and explanation may be provided with respect to the above-described example of FIG. 1, and/or with respect to other examples and contexts. In some embodiments, module 210 of FIG. 2 may correspond to module 910 as described with respect to embodiment 900 of an apparatus 102 within system 100. However, it should be understood that the modules may execute operations in a number of other environments and contexts, and/or modified versions of FIG. 1. Also, although the various modules are presented in the sequence(s) illustrated, it should be understood that the various modules may be configured in numerous orientations.

The embodiment 900 may include module 910 that includes one or more substrates that are configured for operable association with one or more light sources that are configured to emit light that facilitates release of nitric oxide from one or more photolyzable nitric oxide donors. In some embodiments, apparatus 102 may include one or more substrates 104 that are configured for operable association with one or more light sources 106 that are configured to emit light that facilitates release of nitric oxide from one or more photolyzable nitric oxide donors 108. A substrate 104 may be made of numerous materials and combinations of materials. Examples of such materials include, but are not limited to, metals, metal alloys, polymers, copolymers, ceramics, cloth, fabric, and the like. Substrates 104 may be configured in numerous ways. For example, in some embodiments, a substrate 104 may be one or more sheets of one or more materials to which one or more light sources 106 may be associated. In some embodiments, a substrate 104 may be configured to accept one or more light sources 106. For example, in some embodiments, a substrate 104 may include electrical connections that may be operably coupled to one or more light sources 106. In some embodiments, a substrate 104 may be configured to be associated with one or more power supplies. For example, in some embodiments, one or more substrates 104 may be configured to associate with one or more solar cells. In some embodiments, one or more substrates 104 may be configured to associate with one or more batteries (e.g., thin-film batteries). In some embodiments, one or more substrates 104 may be configured to associate with one or more capacitors.

Numerous techniques may be used to fabricate a substrate 104. In some embodiments, a substrate 104 may be fabricated through use of methods used in the computer industry to fabricate circuit boards and/or computer chips. For example, in some embodiments, techniques such as masking and photolithography may be used to fabricate a substrate 104. In some embodiments, circuitry may be printed onto a substrate 104. For example, in some embodiments, circuitry may be sprayed onto a substrate 104 through use of inkjet printing technology. In some embodiments, a substrate 104 may be fabricated through lamination techniques. For example, in some embodiments, one or more electrical connectors may be stamped and/or laminated onto a substrate 104. In some embodiments, laser etching may be used to fabricate a substrate 104. Accordingly, numerous techniques may be used to fabricate one or more substrates 104 that are configured to associate with one or more light sources 106 that are configured to emit light that facilitates release of nitric oxide from one or more photolyzable nitric oxide donors 108.

In some embodiments, a substrate 104 may be configured to be associated with one or more nitric oxide donors. In some embodiments, a substrate 104 may be configured to be associated with one or more photolyable nitric oxide donors 108. In some embodiments, one or more nitric oxide donors may be sprayed onto one or more substrates 104. In some embodiments, one or more photolyzable nitric oxide donors 108 may be sprayed onto one or more substrates 104. In some embodiments, one or more nitric oxide donors may be rolled onto one or more substrates 104. In some embodiments, one or more photolyzable nitric oxide donors 108 may be rolled onto one or more substrates 104. In some embodiments, one or more nitric oxide donors may be chemically coupled to one or more substrates 104. In some embodiments, one or more photolyzable nitric oxide donors 108 may be chemically coupled to one or more substrates 104.

Substrates 104 may exhibit numerous physical characteristics. For example, in some embodiments, substrates 104 may be elastomeric. Methods to prepare elastomeric materials are known and have been reported (e.g., U.S. Pat. Nos. 6,639,007; 6,673,871; 7,105,607). In some embodiments, substrates 104 may be inelastic. For example, in some embodiments, a substrate 104 may be fabricated from one or more metal foils. In some embodiments, substrates 104 may be fabricated with pressure sensitive fibers. For example, in some embodiments, a substrate 104 may include one or more elastomeric materials that self-adhere. Accordingly, in some embodiments, a substrate 104 may be configured in the form of self-adhering athletic tape. In some embodiments, a substrate 104 may include one or more adhesives that are applied to one or more portions of the substrate 104. Accordingly, substrates 104 may be fabricated in numerous configurations.

The embodiment 900 may include module 930 that includes one or more light sources that are configured to emit light that facilitates release of nitric oxide from the one or more photolyzable nitric oxide donors. In some embodiments, apparatus 102 may include one or more light sources 106 that are configured to emit light that facilitates release of nitric oxide from the one or more photolyzable nitric oxide donors 108. A light source 106 may be configured in numerous ways. For example, in some embodiments, a light source 106 may include a chemiluminescent light source 106. In some embodiments, a light source 106 may include a phosphorescent light source 106. In some embodiments, a light source 106 may include a light emitter that is coupled to a power supply. For example, in some embodiments, a light source 106 may include one or more light emitting diodes that are coupled to one or more power supplies. Examples of power supplies include, but are not limited to, capacitors, batteries, electromagnetic receivers 116, and the like. In some embodiments, one or more light sources 106 may be configured to emit light that specifically facilitates release of nitric oxide from one or more photolyzable nitric oxide donors 108. For example, in some embodiments, one or more light sources 106 may be configured to emit one or more wavelengths of light that facilitate photodecomposition of one or more photolyzable nitric oxide donors 108. In some embodiments, one or more light sources 106 may be configured such that they do not emit one or more wavelengths of light that do not facilitate photodecomposition of one or more photolyzable nitric oxide donors 108. Accordingly, in some embodiments, one or more light sources 106 may be configured to emit light that is matched to one or more photolyzable nitric oxide donors 108 and causes photodecomposition of the one or more photolyzable nitric oxide donors 108. In some embodiments, one or more light sources 106 may be configured such that they do not emit light that cross-links biological structures (e.g., proteins) or that causes the formation of DNA adducts. Accordingly, in some embodiments, one or more light sources 106 may be configured to emit light that photolyzes one or more photolyzable nitric oxide donors 108 with reduced damage to surrounding tissue. For example, in some embodiments, one or more light sources 106 may be configured to emit visible light ($\lambda$=550 nm) to facilitate homolytic decomposition of S-nitrosoglutathione to generate nitric oxide (e.g., Singh et al., FEBS Letters, 360:47-51 (1995)). In some embodiments, ultraviolet light may be used to facilitate release of nitric oxide from one or more photolyzable nitric oxide donors 108. For example, in some embodiments, one or more light sources 106 may be configured to emit ultraviolet light ($\lambda$=355 nm) to release nitric oxide from S-nitrosothiols (e.g., Rotta et al., Braz. J. Med. Biol. Res., 36:587-594 (2003)). In some embodiments, one or more light sources 106 may be configured to emit light over a broad range of wavelengths that will facilitate release of nitric oxide from one or more photolyzable nitric oxide donors 108. For example, in some embodiments, $O^2$-benzyl substituted diazeniumdiolates, $O^2$-napthylmethyl substituted diazeniumdiolates, and/or $O^2$-napththylallyl substituted diazeniumdiolates may be photolyzed by light over a broad range of wavelengths ($\lambda$=254 nm to $\lambda$=700 nm) (e.g., U.S. Pat. No. 7,122,529).

Figure 10:
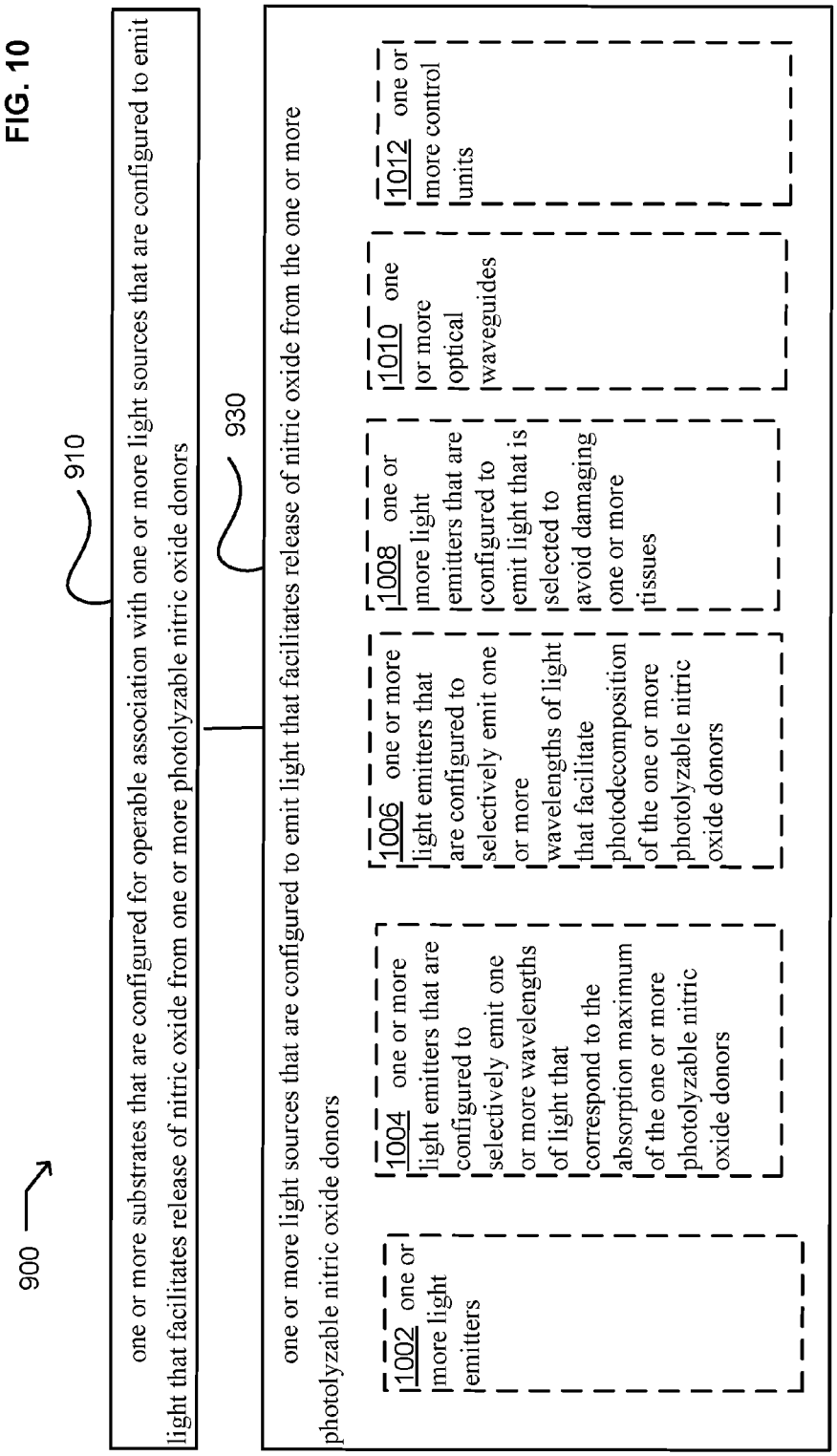
FIG. 10 illustrates alternate embodiments of module 930 of embodiment 900 of apparatus 102 within system 100.

FIG. 10 illustrates alternative embodiments of embodiment 900 of an apparatus 102 within system 100 of FIG. 9. FIG. 10 illustrates example embodiments of module 930 of an apparatus 102. Additional embodiments may include an embodiment 1002, an embodiment 1004, an embodiment 1006, an embodiment 1008, an embodiment 1010, and/or an embodiment 1012.

At embodiment 1002, module 930 may include one or more light emitters. In some embodiments, one or more light sources 106 may include one or more light emitters. Numerous types of light emitters may be associated with one or more light sources 106. Examples of such light emitters include, but are not limited to, light emitting diodes, filaments, arc lamps, fluorescent light emitters, phosphorescent light emitters, chemiluminescent emitters, and the like. In some embodiments, one or more light emitters may be coupled with one or more quantum dots. In some embodiments, one or more light emitters may be coupled with one or more rare-earth materials.

At embodiment 1004, module 930 may include one or more light emitters that are configured to selectively emit one or more wavelengths of light that correspond to the absorption maximum of the one or more photolyzable nitric oxide donors. In some embodiments, one or more light sources 106 may include one or more light emitters that are configured to selectively emit one or more wavelengths of light that correspond to the absorption maximum of one or more photolyzable nitric oxide donors 108.

At embodiment 1006, module 930 may include one or more light emitters that are configured to selectively emit one or more wavelengths of light that facilitate photodecomposition of the one or more photolyzable nitric oxide donors. In some embodiments, one or more light sources 106 may include one or more light emitters that are configured to selectively emit one or more wavelengths of light that facilitate photodecomposition of one or more photolyzable nitric oxide donors 108. In some embodiments, one or more light emitters may emit light that includes a broad range of wavelengths. In some embodiments, one or more light emitters may emit light that includes a narrow range of wavelengths. In some embodiments, one or more light emitters may emit light that includes wavelengths of light that cause photolysis of one or more photolyzable nitric oxide donors 108 and that does not include one or more wavelengths of light that do not cause photolysis of one or more photolyzable nitric oxide donors 108.

At embodiment 1008, module 930 may include one or more light emitters that are configured to emit light that is selected to avoid damaging one or more tissues. In some embodiments, one or more light sources 106 may include one or more light emitters that are configured to emit light that is selected to avoid damaging one or more tissues. In some embodiments, one or more light sources 106 may emit light that is selected to avoid and/or reduce damage to structures and/or tissues of an individual 130. For example, in some embodiments, one or more light sources 106 may emit light that does not include wavelengths of light that are absorbed by nucleic acids. In some embodiments, one or more light sources 106 may emit light that does not include wavelengths of light that are absorbed by polypeptides. In some embodiments, one or more light sources 106 may emit light that does not include one or more wavelengths of light within the following range: 250-320 nm. For example, in some embodiments, one or more light sources 106 may not emit 260 nm light. In some embodiments, one or more light sources 106 may not emit 280 nm light. In some embodiments, one or more light sources 106 may not emit 260 nm light or 280 nm light. Accordingly, numerous combinations of wavelengths of light may be excluded from emission by one or more light sources 106. In some embodiments, light may be emitted continuously. In some embodiments, light may be emitted as a flash. In some embodiments, light may be emitted alternately as continuous light and a flash. In some embodiments, light may be emitted as a pulse.

At embodiment 1010, module 930 may include one or more optical waveguides. In some embodiments, one or more light sources 106 may include one or more light sources 106 that include one or more optical waveguides. Numerous types of optical waveguides may be associated with one or more light sources 106. For example, in some embodiments, a waveguide may be an optical fiber waveguide. In some embodiments, a waveguide may be a rectangular waveguide. In some embodiments, a waveguide may be a dielectric slab waveguide. In some embodiments, optical waveguides may include, but are not limited to, planar waveguides, strip waveguides, and/or fiber waveguides. In some embodiments, an optical waveguide may have a single-mode structure. In some embodiments, an optical waveguide may have a multi-mode structure. In some embodiments, an optical waveguide may exhibit a step refractive index distribution. In some embodiments, an optical waveguide may exhibit a gradient refractive index distribution. An optical waveguide may be constructed from numerous types of materials that include, but are not limited to, glass, polymers, semiconductors, and the like. Methods to construct optical waveguides have been described (e.g., U.S. Pat. No. 7,283,710).

At embodiment 1012, module 930 may include one or more control units. In some embodiments, one or more light sources 106 may include one or more control units 110. In some embodiments, the one or more control units 110 may be operably associated with one or more light sources 106 through use of a hardwired connection. In some embodiments, the one or more control units 110 may be operably associated with one or more light sources 106 through use of a wireless connection. In some embodiments, one or more control units 110 may include numerous types of receivers. Examples of such receivers include, but are not limited to, receivers that receive one or more optical signals 122, radio signals 122, wireless signals 122, hardwired signals 122, infrared signals 122, ultrasonic signals 122, and the like. Such receivers are known and have been described (e.g., U.S. Pat. Nos. RE39,785; 7,218,900; 7,254,160; 7,245,894; 7,206,605; herein incorporated by reference).

FIG. 11 illustrates alternative embodiments of embodiment 900 of an apparatus 102 within system 100 of FIG. 9. FIG. 11 illustrates example embodiments of module 930 of an apparatus 102. Additional embodiments may include an embodiment 1102, an embodiment 1104, an embodiment 1106, an embodiment 1108, an embodiment 1110, an embodiment 1112, an embodiment 1114, and/or an embodiment 1116.

At embodiment 1102, module 930 may include one or more optical fibers. In some embodiments, one or more light sources 106 may include one or more light sources 106 that include one or more optical fibers. Accordingly, in some embodiments, a substrate 104 may be configured to include one or more optical fibers that are configured to associate with one or more light sources 106. Methods to construct optical fibers have been described. Examples of optical fibers include, but are not limited to, optical fibers that include a single core and/or one or more cores. In some embodiments, an optical fiber may include silica glass. In some embodiments, an optical fiber may include a cladding. Optical fibers have been described (e.g., U.S. Pat. Nos. 7,295,741; 7,295,737).

At embodiment 1104, module 930 may include one or more light emitting diodes. In some embodiments, one or more light sources 106 may include one or more light sources 106 that include one or more light emitting diodes. One or more light sources 106 may include one or more light emitting diodes that are configured to emit light of select wavelengths. For example, light emitting diodes may be configured to emit infrared light, visible light, near-ultraviolet light, or ultraviolet light. In some embodiments, a light source 106 may include a conventional light emitting diode that can include a variety of inorganic semiconductor materials. Examples of such materials and the emitting light include, but are not limited to, aluminium gallium arsenide (red and infrared), aluminium gallium phosphide (green), aluminium gallium indium phosphide (high-brightness orange-red, orange, yellow, and green), gallium arsenide phosphide (red, orange-red, orange, and yellow), gallium phosphide (red, yellow and green), gallium nitride (green, pure green, emerald green, blue, and white (if it has an AlGaN Quantum Barrier)), indium gallium nitride (near ultraviolet, bluish-green and blue), silicon carbide (blue), silicon (blue), sapphire (blue), zinc selenide (blue), diamond (ultraviolet), aluminium nitride (near to far ultraviolet), aluminium gallium nitride (near to far ultraviolet), aluminium gallium indium nitride (near to far ultraviolet).

At embodiment 1106, module 930 may include one or more power supplies. In some embodiments, one or more light sources 106 may include one or more power supplies. Numerous types of power supplies may be associated with one or more light sources 106. Examples of such power supplies include, but are not limited to, batteries (e.g., thin film batteries), electromagnetic receivers 116, solar cells, capacitors, line power, and the like.

At embodiment 1108, module 930 may include one or more power supplies that include one or more batteries. In some embodiments, one or more light sources 106 may include one or more power supplies that include one or more batteries. In some embodiments, a battery may include a thin-film fuel cell for providing electrical power. In some embodiments, the fuel cell may be of a solid oxide type (SOFC), a solid polymer type (SPFC), a proton exchange membrane type (PEMFC), and/or substantially any combination thereof. Methods to fabricate such thin-film fuel cells are known and have been described (e.g., U.S. Pat. No. 7,189,471). In some embodiments, one or more batteries may include one or more storage films that are configured for energy storage and energy conversion. Methods to fabricate such storage films are known and have been described (e.g., U.S. Pat. No. 7,238,628). In some embodiments, a battery may be a biobased battery (e.g., U.S. Pat. No. 6,994,934). In some embodiments, one or more batteries may be thin film batteries. Methods to fabricate thin-film batteries are known and have been described (e.g., U.S. Pat. Nos. 7,194,801; 7,144,655; 6,818,356). In some embodiments, one or more thin-film batteries may be laminated onto one or more substrates 104. In some embodiments, laminates that include a substrate 104 and a thin-film battery may be additionally laminated with one or more light emitting diodes. In some embodiments, laminates that include a substrate 104, a thin-film battery, and one or more light emitting diodes may be additionally laminated with one or more photolyzable nitric oxide donors 108. In some embodiments, laminates that include a substrate 104, a thin-film battery, one or more light emitting diodes, and one or more photolyzable nitric oxide donors 108 may be additionally laminated with one or more nitric oxide permeable layers 114. Accordingly, numerous types of batteries may be used.

At embodiment 1110, module 930 may include one or more power supplies that include one or more solar cells. In some embodiments, one or more light sources 106 may include one or more power supplies that include one or more solar cells. Solar cells may be configured in numerous ways. For example, in some embodiments, a solar cell may be configured as a two junction cell. In some embodiments, a solar cell may be configured as a three junction cell. In some embodiments, a solar cell may be configured to selectively absorb energy in a selected photon range. For example, in some embodiments, a cell may be constructed that include an alloy that includes In, Ga, and N having an energy bandgap range of approximately 0.7 eV to 3.4 eV. Such cells provide a good match to the solar energy spectrum (e.g., U.S. Pat. No. 7,217,882). Methods that may be used to fabricate solar cells are known and have been described (e.g., U.S. Pat. No. 7,294,779).

At embodiment 1112, module 930 may include one or more power supplies that include one or more capacitors. In some embodiments, one or more light sources 106 may include one or more power supplies that include one or more capacitors. Capacitors may be configured in numerous ways. For example, in some embodiments, a battery may include a micro-supercapacitor. In some embodiments, such a micro-supercapacitor may include a capacitor substrate; a pair of spaced apart electrodes; a separator disposed between the spaced apart electrodes that define a pair of cavities between the separator and the electrodes; a porous insulator disposed on an outside surface of the spaced apart electrodes; and a top layer closing the pair of cavities (e.g., U.S. Pat. No. 6,621,687). Methods that may be used to fabricate capacitors are known and have been described (e.g., U.S. Pat. Nos. 7,301,754; 7,301,751 and 7,298,605).

At embodiment 1114, module 930 may include one or more electromagnetic receivers. In some embodiments, one or more light sources 106 may include one or more light sources 106 that include one or more electromagnetic receivers 116. In some embodiments, one or more electromagnetic receivers 116 may be used to receive electromagnetic energy 118 for use in providing power to one or more light emitters. Methods to construct electromagnetic receivers 116 have been described (e.g., U.S. Pat. No. 5,571,152).

At embodiment 1116, module 930 may include one or more light sources that are coated with at least one of the one or more photolyzable nitric oxide donors. In some embodiments, one or more light sources 106 may include one or more light sources 106 that are coated with at least one of the one or more photolyzable nitric oxide donors 108. For example, in some embodiments, a light source 106 may be configured as a sheet that is coated with one or more photolyzable nitric oxide donors 108. In some embodiments, one or more light sources 106 may be partially coated with one or more photolyzable nitric oxide donors 108.

Figure 12:
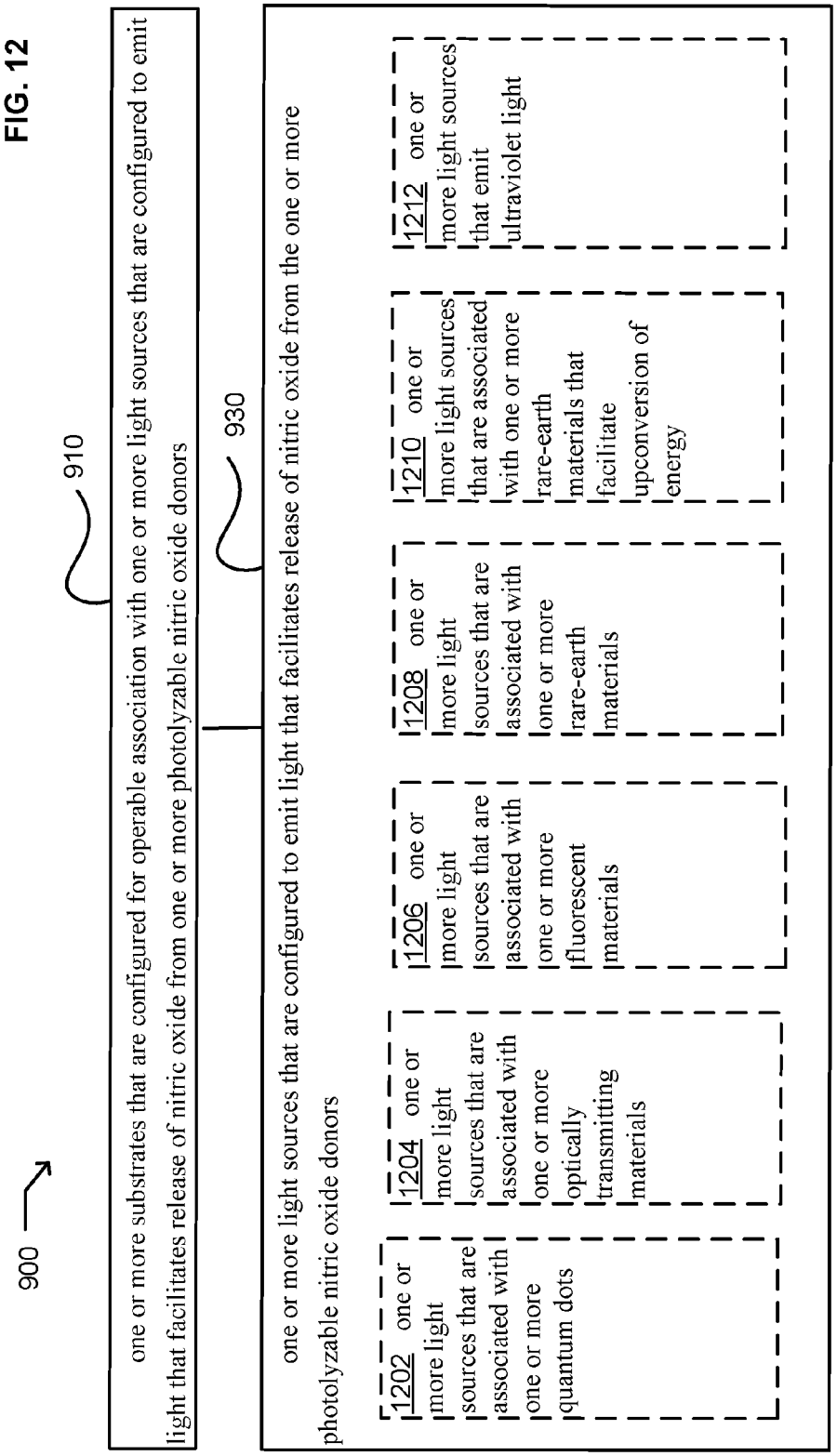
FIG. 12 illustrates alternate embodiments of module 930 of embodiment 900 of apparatus 102 within system 100.

FIG. 12 illustrates alternative embodiments of embodiment 900 of an apparatus 102 within system 100 of FIG. 9. FIG. 12 illustrates example embodiments of module 930 of an apparatus 102. Additional embodiments may include an embodiment 1202, an embodiment 1204, an embodiment 1206, an embodiment 1208, an embodiment 1210, and/or an embodiment 1212.

At embodiment 1202, module 930 may include one or more light sources that are associated with one or more quantum dots. In some embodiments, one or more light sources 106 may include one or more light sources 106 that are associated with one or more quantum dots (e.g., U.S. Pat. No. 7,235,361; herein incorporated by reference). For example, in some embodiments, one or more light sources 106 may be configured to emit one or more wavelengths of light that are absorbed by one or more quantum dots. In some embodiments, one or more quantum dots may be configured to absorb light and then emit one or more wavelengths of light that cause release of nitric oxide from one or more nitric oxide donors 108. Accordingly, in some embodiments, emission from one or more first quantum dots may be tuned to facilitate release of nitric oxide from one or more first photolyzable nitric oxide donors 108 and emission from one or more second quantum dots may be tuned to facilitate release of nitric oxide from one or more second photolyzable nitric oxide donors 108.

At embodiment 1204, module 930 may include one or more light sources that are associated with one or more optically transmitting materials. In some embodiments, one or more light sources 106 may be associated with one or more optically transmitting materials. In some embodiments, optically transmitting materials include all substances that function to alter or control electromagnetic radiation in the ultraviolet, visible, or infrared spectral regions. Such materials may be fabricated into optical elements such as lenses, mirrors, windows, prisms, polarizers, detectors, and modulators. These materials may refract, reflect, transmit, disperse, polarize, detect, and/or transform light. Examples of optically transmitting materials include, but are not limited to, glass, crystalline materials, polymers, plastics, and the like. In some embodiments, one or more light sources 106 may include fused silica which transmits to about 180 nm. In some embodiments, one or more light sources 106 may include calcium fluoride which transmits into the ultraviolet region to about 140 nm. Accordingly, a light source 106 may include numerous types of optically transmitting materials.

At embodiment 1206, module 930 may include one or more light sources that are associated with one or more fluorescent materials. In some embodiments, one or more light sources 106 may include one or more light sources 106 that are associated with one or more fluorescent materials. Numerous fluorescent materials may be associated with one or more light sources 106. Examples of such materials include, but are not limited to, 1,4-diphenylbutadiyne; 9,10-diphenylanthracene; benzene; biphenyl; ethyl-p-dimethylaminobenzoate; naphthalene; P-terphenyl; ethyl-p-dimethylaminobenzoate; stilbene; tryptophan; tyrosine; 1,2-diphenylacetylene; 7-methoxycoumarin-4-acetic acid; anthracene; indo-1; POPOP; P-quaterphenyl; pyrene; and the like.

At embodiment 1208, module 930 may include one or more light sources that are associated with one or more rare-earth materials. In some embodiments, one or more light sources 106 may include one or more light sources 106 that are associated with one or more rare-earth materials. In some embodiments, one or more rare-earth materials may include one or more rare-earth elements. The rare-earth elements are a collection of sixteen chemical elements in the periodic table, namely scandium, yttrium, and fourteen of the fifteen lanthanoids (excluding promethium). In some embodiments, one or more rare-earth materials may include one or more rare-earth elements that fluoresce.

At embodiment 1210, module 930 may include one or more light sources that are associated with one or more rare-earth materials that facilitate upconversion of energy. In some embodiments, one or more light sources 106 may include one or more light sources 106 that are associated with one or more rare-earth materials that facilitate upconversion of energy. In some embodiments, infrared light may be upconverted to visible light (e.g., Mendioroz et al., Optical Materials, 26:351-357 (2004)). In some embodiments, infrared light may be upconverted to ultraviolet light (e.g., Mendioroz et al., Optical Materials, 26:351-357 (2004)). In some embodiments, one or more light sources 106 may include one or more rare-earth materials (e.g., ytterbium-erbium, ytterbium-thulium, or the like) that facilitate upconversion of energy (e.g., U.S. Pat. No. 7,088,040; herein incorporated by reference). For example, in some embodiments, one or more light sources 106 may be associated with $Nd^{3+}$ doped $KPb_2Cl_5$ crystals. In some embodiments, one or more light sources 106 may be associated with thiogallates doped with rare earths, such as $CaGa_2S_4:Ce^{3+}$ and $SrGa_2S_4:Ce^{3+}$. In some embodiments, one or more light sources 106 may be associated with aluminates that are doped with rare earths, such as $YAlO_3:Ce^{3+}$, $YGaO_3:Ce^{3+}$, $Y(Al,Ga)O_3:Ce^{3+}$, and orthosilicates $M_2SiO_5:Ce^{3+}$ (M:Sc, Y, Sc) doped with rare earths, such as, for example, $Y_2SiO_5$: $Ce^{3+}$. In some embodiments, yttrium may be replaced by scandium or lanthanum (e.g., U.S. Pat. Nos. 6,812,500 and 6,327,074; herein incorporated by reference). Numerous materials that may be used to upconvert energy have been described (e.g., U.S. Pat. Nos. 5,956,172; 5,943,160; 7,235, 189; 7,215,687; herein incorporated by reference).

At embodiment 1212, module 930 may include one or more light sources that emit ultraviolet light. In some embodiments, one or more light sources 106 may include one or more light sources 106 that emit ultraviolet light. In some embodiments, one or more light sources 106 may emit a broad spectrum of ultraviolet light. In some embodiments, one or more light sources 106 may emit a narrow spectrum of ultraviolet light. In some embodiments, one or more light sources 106 that emit one or more wavelengths of ultraviolet light that are specifically selected to release nitric oxide from one or more photolyzable nitric oxide donors 108. In some embodiments, one or more light sources 106 may emit ultraviolet light that does not include one or more wavelengths of light. In some embodiments, one or more light sources 106 may emit ultraviolet light that is selected to avoid and/or reduce damage to structures and/or tissues of an individual 130. For example, in some embodiments, one or more light sources 106 may emit ultraviolet light that does not include wavelengths of light that are absorbed by nucleic acids. In some embodiments, one or more light sources 106 may emit ultraviolet light that does not include wavelengths of light that are absorbed by polypeptides. In some embodiments, one or more light sources 106 may emit light that does not include one or more wavelengths of ultraviolet light within the following range: 250-320 nm. For example, in some embodiments, one or more light sources 106 may not emit 260 nm light. In some embodiments, one or more light sources 106 may not emit 280 nm light. In some embodiments, one or more light sources 106 may not emit 260 nm light or 280 nm light. Accordingly, numerous combinations of wavelengths of light may be excluded from emission by one or more light sources 106. In some embodiments, light may be emitted continuously. In some embodiments, light may be emitted as a flash. In some embodiments, light may be emitted alternately as continuous light and a flash. In some embodiments, light may be emitted as a pulse. In some embodiments, light may be emitted continuously, as a flash, as a pulse, or substantially any combination thereof.

Figure 13:
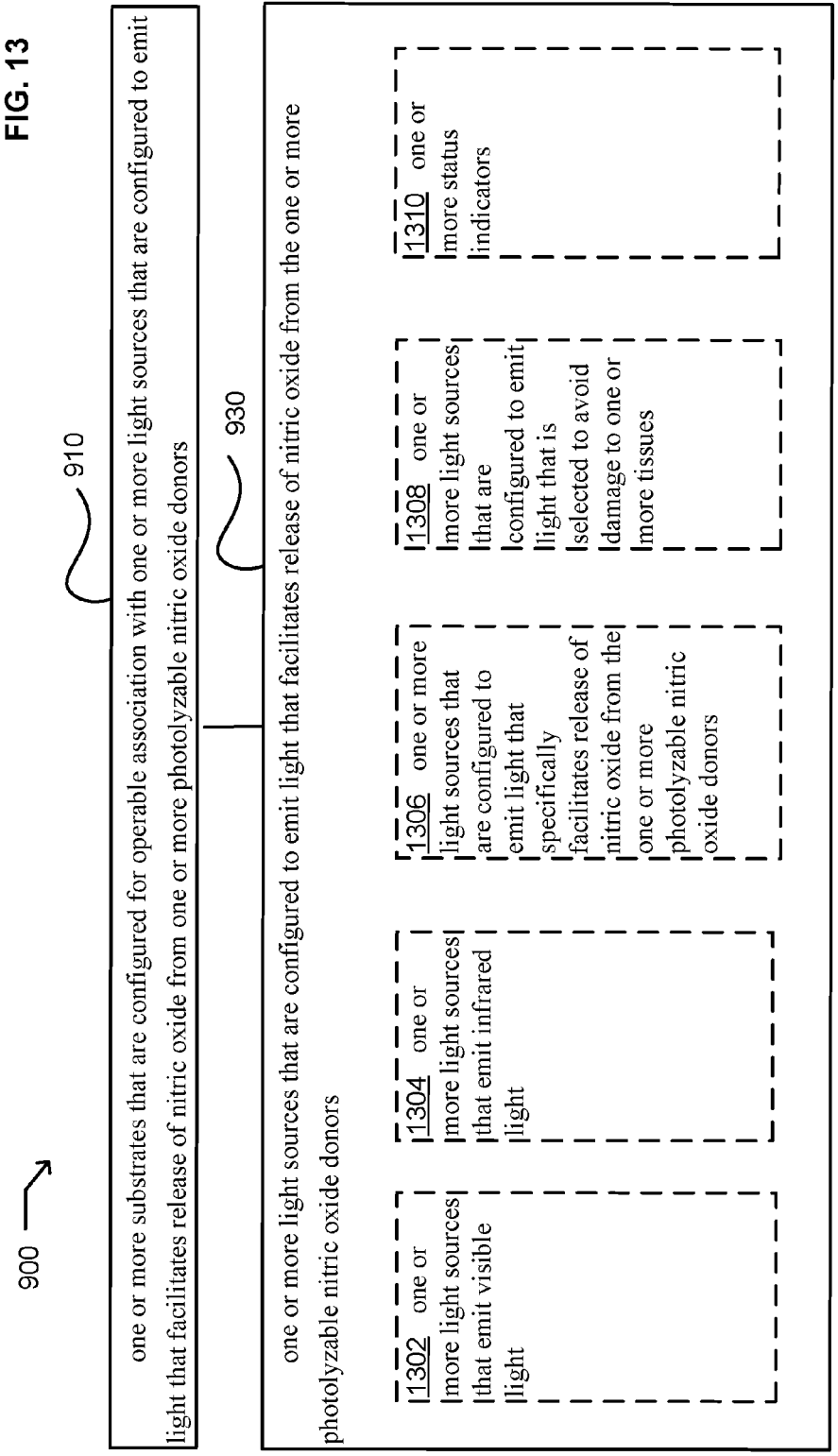
FIG. 13 illustrates alternate embodiments of module 930 of embodiment 900 of apparatus 102 within system 100.

FIG. 13 illustrates alternative embodiments of embodiment 900 of an apparatus 102 within system 100 of FIG. 9. FIG. 13 illustrates example embodiments of module 930 of an apparatus 102. Additional embodiments may include an embodiment 1302, an embodiment 1304, an embodiment 1306, an embodiment 1308, and/or an embodiment 1310.

At embodiment 1302, module 930 may include one or more light sources that emit visible light. In some embodiments, one or more light sources 106 may include one or more light sources 106 that emit visible light. In some embodiments, one or more light sources 106 may emit a broad spectrum of visible light. In some embodiments, one or more light sources 106 may emit a narrow spectrum of visible light. In some embodiments, one or more light sources 106 may emit one or more wavelengths of visible light that are specifically selected to release nitric oxide from one or more photolyzable nitric oxide donors 108. In some embodiments, one or more light sources 106 may emit visible light that does not include one or more wavelengths of light. In some embodiments, one or more light sources 106 may emit visible light that is selected to avoid and/or reduce damage to structures and/or tissues of an individual 130. Accordingly, numerous combinations of wavelengths of light may be excluded from emission by one or more light sources 106. In some embodiments, light may be emitted continuously. In some embodiments, light may be emitted as a flash. In some embodiments, light may be emitted alternately as continuous light and a flash. In some embodiments, light may be emitted as a pulse. In some embodiments, light may be emitted continuously, as a flash, as a pulse, or substantially any combination thereof. In some embodiments, the visible light may be upconverted.

At embodiment 1304, module 930 may include one or more light sources that emit infrared light. In some embodiments, one or more light sources 106 may include one or more light sources 106 that emit infrared light. In some embodiments, one or more light sources 106 may emit a broad spectrum of infrared light. In some embodiments, one or more light sources 106 may emit a narrow spectrum of infrared light. In some embodiments, one or more light sources 106 may emit one or more wavelengths of infrared light that are specifically selected to release nitric oxide from one or more photolyzable nitric oxide donors 108. In some embodiments, one or more light sources 106 may emit infrared light that does not include one or more wavelengths of light. In some embodiments, one or more light sources 106 may emit infrared light that is selected to avoid and/or reduce damage to structures and/or tissues of an individual 130. Accordingly, numerous combinations of wavelengths of light may be excluded from emission by one or more light sources 106. In some embodiments, light may be emitted continuously. In some embodiments, light may be emitted as a flash. In some embodiments, light may be emitted alternately as continuous light and a flash. In some embodiments, light may be emitted as a pulse. In some embodiments, light may be emitted continuously, as a flash, as a pulse, or substantially any combination thereof. In some embodiments, the infrared light may be upconverted.

At embodiment 1306, module 930 may include one or more light sources that are configured to emit light that specifically facilitates release of nitric oxide from the one or more photolyzable nitric oxide donors. In some embodiments, one or more light sources 106 may include one or more light sources 106 that are configured to emit light that specifically facilitates release of nitric oxide from the one or more photolyzable nitric oxide donors 108. For example, in some embodiments, one or more light sources 106 may be configured to emit light that includes one or more wavelengths of light that correspond to the absorption maximum for one or more photolyzable nitric oxide donors 108. Examples of nitric oxide donors and their associated $\lambda_{max}$ (nm) are provided in Table I below. Accordingly, one or more light sources 106 may be configured to emit numerous wavelengths of light.

TABLE I

Example Nitric Oxide Donors

| Compound Name | $\lambda_{max}$ (nm) |
|---|---|
| $O^2$-(Acetoxymethyl) 1-(N, N-Diethylamino)diazen-1-ium-1,2-diolate | 230 |
| $O^2$-(Acetoxymethyl) 1-(Pyrrolidin-1-yl)diazen-1-ium-1,2-diolate | 256 |
| Sodium 1-(N-Benzyl-N-methylamino)diazen-1-ium-1,2-diolate | 252 |
| $O^2$-[(2,3,4,6-Tetra-O-acetyl)-β-D-glucosyl] 1-[4-(2,3-Dihydroxypropyl)piperazin-1 | 232 |
| Sodium 1-[4-(2,3-Dihydroxypropyl)piperazin-1-yl-]diazen-1-ium-1,2-diolate | 248.5 |
| $O^2$-Methyl 1-[(4-Carboxamido)piperidin-1-yl]diazen-1-ium-1,2-diolate | 241 |

TABLE I-continued

Example Nitric Oxide Donors

| Compound Name | $\lambda_{max}$ (nm) |
|---|---|
| $O^2$-(2-Chloropyrimidin-4-yl) 1-(Pyrrolidin-1-yl)diazen-1-ium-1,2-diolate | 274 |
| $O^2$-(2,4-Dinitrophenyl) 1-[4-(N,N-Diethylcarboxamido)piperazin-1-yl]diazen-1-ium-1,2-diolate | 300 |
| $O^2$-(2,4-Dinitrophenyl) 1-(4-Nicotinylpiperazin-1-yl)diazen-1-ium-1,2-diolate | 300 |
| $O^2$-(2,4-Dinitrophenyl) 1-{4-[2-(4-{2-Methylpropyl}phenyl)propionyl]piperazin-1-yl}diazen-1-ium-1,2-diolate | 300 |
| Sodium 1-(4-Benzyloxycarbonylpiperazin-1-yl)diazen-1-ium-1,2-diolate | 252 |
| $O^2$-(2,4-Dinitrophenyl) 1-[4-(tert-Butoxycarbonyl)piperazin-1-yl]diazen-1-ium-1,2-diolate | 299 |
| $O^2$-(2,4-Dinitrophenyl) 1-(4-Acetylpiperazin-1-yl)diazen-1-ium-1,2-diolate | 394 |
| $O^2$-(2,4-Dinitrophenyl) 1-[4-(Succinimidoxycarbonyl)piperazin-1-yl]diazen-1-ium-1,2-diolate | 300 |
| $O^2$-(2,4-Dinitrophenyl) 1-(Piperazin-1-yl)diazen-1-ium-1,2-diolate, Hydrochloride Salt | 297 |
| $O^2$-(2,3,4,6-Tetra-O-acetyl-D-glucopyranosyl) 1-(N,N-Diethylamino)diazen-1-ium-1,2-diolate | 228 |
| $O^2$-(-D-Glucopyranosyl) 1-(N,N-Diethylamino)diazen-1-ium-1,2-diolate | 228 |
| Sodium (Z)-1-(N,N-Diethylamino)diazen-1-ium-1,2-diolate | 250 |
| 1-[N-(2-Aminoethyl)-N-(2-ammonioethyl)amino]diazen-1-ium-1,2-diolate | 252 |
| Sodium 1-(N,N-Dimethylamino)diazen-1-ium-1,2-diolate | 250 |
| $O^2$-(2,4-Dinitrophenyl) 1-(N,N-Diethylamino)diazen-1-ium-1,2-diolate | 302 |
| 1-[N-(3-Aminopropyl)-N-(3-ammoniopropyl]diazen-1-ium-1,2-diolate | 252 |
| 1-[N-(3-Aminopropyl)-N-(3-ammoniopropyl]diazen-1-ium-1,2-diolate | 252 |
| Bis-diazeniumdiolated benzyl imidate dehydrate | 264 |
| p-Bisdiazeniumdiolated benzene | 316 |
| Methane Trisdiazeniumdiolate trihydrate | 316 |
| $O^2$-(β-D-Glucopyranosyl) 1-(Isopropylamino)diazen-1-ium-1,2-diolate | 278 |
| Sodium 1-[4-(5-Dimethylamino-1-naphthalenesulfonyl)piperazin-1-yl]diazen-1-ium-1,2-diolate | 344 |
| 1-(2-Methyl-1-propenyl)piperidine diazeniumdiolate | 246 |
| 1-(2-Methyl-1-propenyl)pyrrolidine diazeniumdiolate | 246 |
| $O^2$-Vinyl 1-(Pyrrolidin-1-yl)diazen-1-ium-1,2-diolate | 268 |
| 1-{N-[3-Aminopropyl]-N-[4-(3-aminopropylammoniobutyl)]}diazen-1-ium-1,2-diolate | 252 |
| Disodium 1-[(2-Carboxylato)pyrrolidin-1-yl]diazen-1-ium-1,2-diolate | 252 |
| 1-[N-(3-Ammoniopropyl)-N-(n-propyl)amino]diazen-1-ium-1,2-diolate | 250 |
| (Z)-1-{N-Methyl-N-[6-(N-methylammoniohexyl)amino]}diazen-1-ium-1,2-diolate | 250 |
| $O^2$-(2,4-Dinitrophenyl) 1-[(4-Ethoxycarbonyl)piperazin-1-yl]diazen-1-ium-1,2-diolate | 300 |

At embodiment 1308, module 930 may include one or more light sources that are configured to emit light that is selected to avoid damage to one or more tissues. In some embodiments, one or more light sources 106 may include one or more light sources 106 that are configured to emit light that is selected to avoid damaging one or more tissues. In some embodiments, one or more light sources 106 may emit light that is selected to avoid and/or reduce damage to structures and/or tissues of an individual 130. For example, in some embodiments, one or more light sources 106 may emit light that does not include wavelengths of light that are absorbed by nucleic acids. In some embodiments, one or more light sources 106 may emit light that does not include wavelengths of light that are absorbed by polypeptides. In some embodiments, one or more light sources 106 may emit light that does not include one or more wavelengths of light within the following range: 250-320 nm. For example, in some embodiments, one or more light sources 106 may not emit 260 nm light. In some embodiments, one or more light sources 106 may not emit 280 nm light. In some embodiments, one or more light sources 106 may not emit 260 nm light or 280 nm light. Accordingly, numerous combinations of wavelengths of light may be excluded from emission by one or more light sources 106. In some embodiments, light may be emitted continuously. In some embodiments, light may be emitted as a flash. In some embodiments, light may be emitted alternately as continuous light and a flash. In some embodiments, light may be emitted as a pulse.

At embodiment 1310, module 930 may include one or more status indicators. In some embodiments, one or more light sources 106 may include one or more light sources 106 that include one or more status indicators. In some embodiments, one or more light sources 106 may include one or more status indicators that indicate output from one or more power supplies. Accordingly, in some embodiments, one or more status indicators may be operably associated with one or more power supplies. In some embodiments, one or more status indicators may be associated with one or more light emitters and indicate output from one or more light sources 106. Accordingly, in some embodiments, one or more status indicators may be used to indicate if a power supply, a light emitter, a photolyzable nitric oxide donor 108, or substantially any combination thereof has been diminished and/or exhausted. In some embodiments, one or more status indicators may be configured to indicate that one or more light emitters should be replaced. In some embodiments, one or more status indicators may be configured to indicate that one or more power supplies should be replaced and/or recharged. A status indicator may be configured in numerous ways. In some embodiments, a status indicator may include one or more lights. For example, in some embodiments, a status indicator that is associated with one or more power supplies may illuminate a green light to indicate an adequate amount of battery power and illuminate a red light to indicate a diminished amount of battery power. In some embodiments, a status indicator may display one or more messages on a liquid crystal display. Accordingly, status indicators may be configured in numerous ways.

Figure 14:
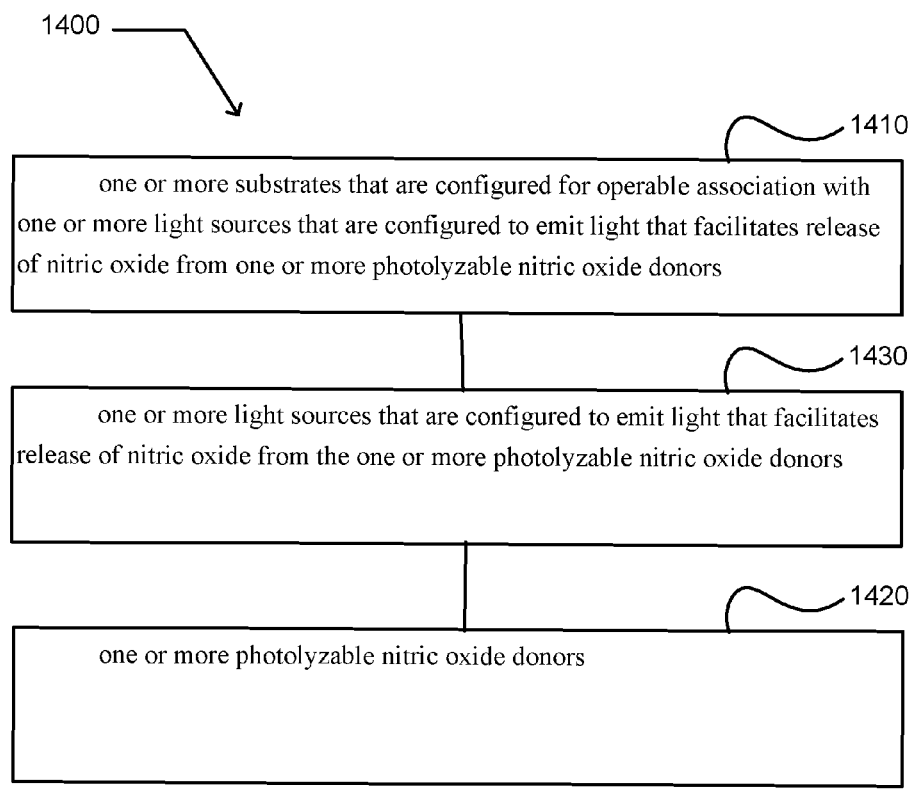
FIG. 14 illustrates embodiment 1400 of apparatus 102 within system 100.

FIG. 14 illustrates embodiment 1400 of an apparatus 102 within system 100. In FIG. 14, discussion and explanation may be provided with respect to the above-described example of FIG. 1, and/or with respect to other examples and contexts. In some embodiments, module 210 of FIG. 2 may correspond to module 1410 as described with respect to embodiment 1400 of an apparatus 102 within system 100. In some embodiments, module 720 of FIG. 7 may correspond to module 1420 as described with respect to embodiment 1400 of an apparatus 102 within system 100. In some embodiments, module 930 of FIG. 9 may correspond to module 1430 as described with respect to embodiment 1400 of an apparatus 102 within system 100. However, it should be understood that the modules may execute operations in a number of other environments and contexts, and/or modified versions of FIG. 1. Also, although the various modules are presented in the sequence(s) illustrated, it should be understood that the various modules may be configured in numerous orientations.

The embodiment 1400 may include module 1410 that includes one or more substrates that are configured for operable association with one or more light sources that are configured to emit light that facilitates release of nitric oxide from one or more photolyzable nitric oxide donors. In some embodiments, apparatus 102 may include one or more substrates 104 that are configured for operable association with one or more light sources 106 that are configured to emit light that facilitates release of nitric oxide from one or more photolyzable nitric oxide donors 108. A substrate 104 may be made of numerous materials and combinations of materials. Examples of such materials include, but are not limited to, metals, metal alloys, polymers, copolymers, ceramics, cloth, fabric, and the like. Substrates 104 may be configured in numerous ways. For example, in some embodiments, a substrate 104 may be one or more sheets of one or more materials to which one or more light sources 106 may be associated. In some embodiments, a substrate 104 may be configured to accept one or more light sources 106. For example, in some embodiments, a substrate 104 may include electrical connections that may be operably coupled to one or more light sources 106. In some embodiments, a substrate 104 may be configured to be associated with one or more power supplies. For example, in some embodiments, one or more substrates 104 may be configured to associate with one or more solar cells. In some embodiments, one or more substrates 104 may be configured to associate with one or more batteries (e.g., thin-film batteries). In some embodiments, one or more substrates 104 may be configured to associate with one or more capacitors.

Numerous techniques may be used to fabricate a substrate 104. In some embodiments, a substrate may be fabricated through use of methods used in the computer industry to fabricate circuit boards and/or computer chips. For example, in some embodiments, techniques such as masking and photolithography may be used to fabricate a substrate 104. In some embodiments, circuitry may be printed onto a substrate 104. For example, in some embodiments, circuitry may be sprayed onto a substrate 104 through use of inkjet printing technology. In some embodiments, a substrate 104 may be fabricated through lamination techniques. For example, in some embodiments, one or more electrical connectors may be stamped and/or laminated onto a substrate 104. In some embodiments, laser etching may be used to fabricate a substrate 104. Accordingly, numerous techniques may be used to fabricate one or more substrates 104 that are configured to associate with one or more light sources 106 that are configured to emit light that facilitates release of nitric oxide from one or more photolyzable nitric oxide donors 108.

In some embodiments, a substrate 104 may be configured to be associated with one or more nitric oxide donors. In some embodiments, a substrate 104 may be configured to be associated with one or more photolyable nitric oxide donors 108. In some embodiments, one or more nitric oxide donors may be sprayed onto one or more substrates 104. In some embodiments, one or more photolyzable nitric oxide donors 108 may be sprayed onto one or more substrates 104. In some embodiments, one or more nitric oxide donors may be rolled onto one or more substrates 104. In some embodiments, one or more photolyzable nitric oxide donors 108 may be rolled onto one or more substrates 104. In some embodiments, one or more nitric oxide donors may be chemically coupled to one or more substrates 104. In some embodiments, one or more photolyzable nitric oxide donors 108 may be chemically coupled to one or more substrates 104.

Substrates 104 may exhibit numerous physical characteristics. For example, in some embodiments, substrates 104 may be elastomeric. Methods to prepare elastomeric materials are known and have been reported (e.g., U.S. Pat. Nos. 6,639,007; 6,673,871; 7,105,607). In some embodiments, substrates 104 may be inelastic. For example, in some embodiments, a substrate 104 may be fabricated from one or more metal foils. In some embodiments, substrates 104 may be fabricated with pressure sensitive fibers. For example, in some embodiments, a substrate 104 may include one or more elastomeric materials that self-adhere. Accordingly, in some embodiments, a substrate 104 may be configured in the form of self-adhering athletic tape. In some embodiments, a substrate 104 may include one or more adhesives that are applied to one or more portions of the substrate 104. Accordingly, substrates 104 may be fabricated in numerous configurations.

The embodiment 1400 may include module 1430 that includes one or more light sources that are configured to emit light that facilitates release of nitric oxide from the one or more photolyzable nitric oxide donors. In some embodiments, apparatus 102 may include one or more light sources 106 that are configured to emit light that facilitates release of nitric oxide from the one or more photolyzable nitric oxide donors 108. A light source 106 may be configured in numerous ways. For example, in some embodiments, a light source 106 may include a chemiluminescent light source 106. In some embodiments, a light source 106 may include a phosphorescent light source 106. In some embodiments, a light source 106 may include a light emitter that is coupled to a power supply. For example, in some embodiments, a light source 106 may include one or more light emitting diodes that are coupled to one or more power supplies. Examples of power supplies include, but are not limited to, capacitors, batteries, electromagnetic receivers 116, and the like. In some embodiments, one or more light sources 106 may be configured to emit light that specifically facilitates release of nitric oxide from one or more photolyzable nitric oxide donors 108. For example, in some embodiments, one or more light sources 106 may be configured to emit one or more wavelengths of light that facilitate photodecomposition of one or more photolyzable nitric oxide donors 108. In some embodiments, one or more light sources 106 may be configured such that they do not emit one or more wavelengths of light that do not facilitate photodecomposition of one or more photolyzable nitric oxide donors 108. Accordingly, in some embodiments, one or more light sources 106 may be configured to emit light that is matched to one or more photolyzable nitric oxide donors 108 and causes photodecomposition of the one or more photolyzable nitric oxide donors 108. In some embodiments, one or more light sources 106 may be configured such that they do not emit light that cross-links biological structures (e.g., proteins) or that causes the formation of DNA adducts. Accordingly, in some embodiments, one or more light sources 106 may be configured to emit light that photolyzes one or more photolyzable nitric oxide donors 108 with reduced damage to surrounding tissue. For example, in some embodiments, one or more light sources 106 may be configured to emit visible light ($\lambda=550$ nm) to facilitate homolytic decomposition of S-nitrosoglutathione to generate nitric oxide (e.g., Singh et al., FEBS Letters, 360:47-51 (1995)). In some embodiments, ultraviolet light may be used to facilitate release of nitric oxide from one or more photolyzable nitric oxide donors 108. For example, in some embodiments, one or more light sources 106 may be configured to emit ultraviolet light ($\lambda=355$ nm) to release nitric oxide from S-nitrosothiols (e.g., Rotta et al., Braz. J. Med. Biol. Res., 36:587-594 (2003)). In some embodiments, one or more light sources 106 may be configured to emit light over a broad range of wavelengths that will facilitate release of nitric oxide from one or more photolyzable nitric oxide donors 110. For example, in some embodiments, $O^2$-benzyl substituted diazeniumdiolates, $O^2$-napthylmethyl substituted diazeniumdiolates, and/or $O^2$-napththylallyl substituted diazeniumdiolates may be photolyzed by light over a broad range of wavelengths ($\lambda=254$ nm to $\lambda=700$ nm) (e.g., U.S. Pat. No. 7,122,529).

The embodiment 1400 may include module 1420 that includes one or more photolyzable nitric oxide donors. In some embodiments, apparatus 102 may include one or more photolyzable nitric oxide donors 108 that release nitric oxide upon photolysis. Examples of such photolyzable nitric oxide donors 108 include, but are not limited to, diazeniumdiolates (e.g., U.S. Pat. Nos. 7,105,502; 7,122,529; 6,673,338; herein incorporated by reference), trans-[RuCl([15]aneN4)NO]+2 (Ferezin et al., Nitric Oxide, 13:170-175 (2005), Bonaventura et al., Nitric Oxide, 10:83-91 (2004)), nitrosyl ligands (e.g., U.S. Pat. No. 5,665,077; herein incorporated by reference, Chmura et al., Nitric Oxide, 15:370-379 (2005), Flitney et al., Br. J. Pharmacol., 107:842-848 (1992), Flitney et al., Br. J. Pharmacol., 117:1549-1557 (1996), Matthews et al., Br. J. Pharmacol., 113:87-94 (1994)), 6-Nitrobenzo[a]pyrene (e.g., Fukuhara et al., J. Am. Chem. Soc., 123:8662-8666 (2001)), S-nitroso-glutathione (e.g., Rotta et al., Braz. J. Med. Res., 36:587-594 (2003), Flitney and Megson, J. Physiol., 550:819-828 (2003)), S-nitrosothiols (e.g., Andrews et al., British Journal of Pharmacology, 138:932-940 (2003), Singh et al., FEBS Lett., 360:47-51 (1995)), 2-Methyl-2-nitrosopropane (e.g., Pou et al., Mol. Pharm., 46:709-715 (1994), Wang et al., Chem. Rev., 102:1091-1134 (2002)), imidazolyl derivatives (e.g., U.S. Pat. No. 5,374,710; herein incorporated by reference).

Figure 15:
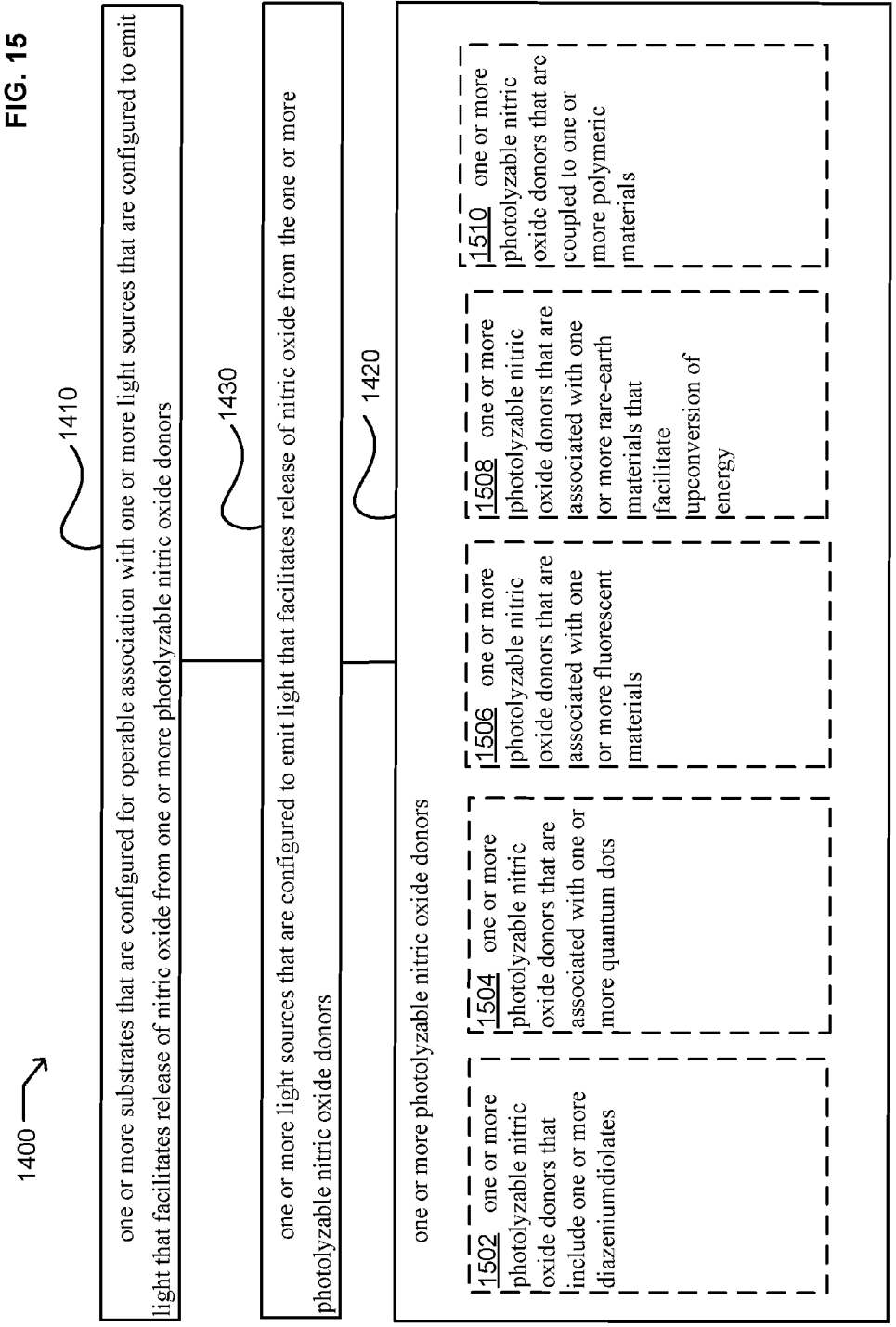
FIG. 15 illustrates alternate embodiments of module 1420 of embodiment 1400 of apparatus 102 within system 100.

FIG. 15 illustrates alternative embodiments of embodiment 1400 of an apparatus 102 within system 100 of FIG. 14. FIG. 15 illustrates example embodiments of module 1420 of an apparatus 102. Additional embodiments may include an embodiment 1502, an embodiment 1504, an embodiment 1506, an embodiment 1508, and/or an embodiment 1510.

At embodiment 1502, module 1420 may include one or more photolyzable nitric oxide donors that include one or more diazeniumdiolates. In some embodiments, one or more photolyzable nitric oxide donors 108 may include one or more photolyzable nitric oxide donors 108 that include one or more diazeniumdiolates. Many photolyzable nitric oxide donors 108 that are diazeniumdiolates are known and have been described (e.g., U.S. Pat. No. 7,122,529). Examples of such diazeniumdiolates include, but are not limited to, $O^2$-benzyl,$O^2$-naphthylmethyl substituted diazeniumdiolates and $O^2$-naphthylallyl substituted diazeniumdiolates.

At embodiment 1504, module 1420 may include one or more photolyzable nitric oxide donors that are associated with one or more quantum dots. In some embodiments, one or more photolyzable nitric oxide donors 108 may include one or more photolyzable nitric oxide donors 108 that are associated with one or more quantum dots. For example, in some embodiments, one or more diazeniumdiolates may be associated with one or more quantum dots. In some embodiments, one or more quantum dots may be tuned to emit light that facilitates photolysis of one or more photolyzable nitric oxide donors 108. In some embodiments, a quantum dot may be tuned to emit light that specifically facilitates photolysis of one or more photolyzable nitric oxide donors 108. For example, in some embodiments, one or more quantum dots may emit select wavelengths of light that correspond to wavelengths of light that cause photolysis of one or more photolyzable nitric oxide donors 108. In some embodiments, one or more quantum dots may be selected that absorb light emitted by one or more light sources 106 and emit light that facilitates photolysis of one or more photolyzable nitric oxide donors 108.

At embodiment 1506, module 1420 may include one or more photolyzable nitric oxide donors that are associated with one or more fluorescent materials. In some embodiments, one or more photolyzable nitric oxide donors 108 may include one or more photolyzable nitric oxide donors 108 that are associated with one or more fluorescent materials. Numerous fluorescent materials may be associated with one or more photolyzable nitric oxide donors 108. Examples of such materials include, but are not limited to, 1,4-diphenylbutadiyne; 9,10-diphenylanthracene; benzene; biphenyl; ethyl-p-dimethylaminobenzoate; naphthalene; P-terphenyl; ethyl-p-dimethylaminobenzoate; stilbene; tryptophan; tyrosine; 1,2-diphenylacetylene; 7-methoxycoumarin-4-acetic acid; anthracene; indo-1; POPOP; P-quaterphenyl; pyrene; and the like.

At embodiment 1508, module 1420 may include one or more photolyzable nitric oxide donors that are associated with one or more rare-earth materials that facilitate upconversion of energy. In some embodiments, one or more photolyzable nitric oxide donors 108 may include one or more photolyzable nitric oxide donors 108 that are associated with one or more rare-earth materials that facilitate upconversion of energy. In some embodiments, infrared light may be upconverted to visible light (e.g., Mendioroz et al., Optical Materials, 26:351-357 (2004)). In some embodiments, infrared light may be upconverted to ultraviolet light (e.g., Mendioroz et al., Optical Materials, 26:351-357 (2004)). In some embodiments, one or more photolyzable nitric oxide donors 108 may be associated with one or more rare-earth materials (e.g., ytterbium-erbium, ytterbium-thulium, or the like) that facilitate upconversion of energy (e.g., U.S. Pat. No. 7,088,040; herein incorporated by reference). For example, in some embodiments, one or more photolyzable nitric oxide donors 108 may be associated with $Nd^{3+}$ doped $KPb_2Cl_5$ crystals. In some embodiments, one or more photolyzable nitric oxide donors 108 may be associated with thiogallates doped with rare earths, such as $CaGa_2S_4:Ce^{3+}$ and $SrGa_2S_4:Ce^{3+}$. In some embodiments, one or more photolyzable nitric oxide donors 108 may be associated with aluminates that are doped with rare earths, such as $YAlO_3$: $Ce^{3+}$, $YGaO_3:Ce^{3+}$, $Y(Al,Ga)O_3:Ce^{3+}$, and orthosilicates $M_2SiO_5:Ce^{3+}$ (M:Sc, Y, Sc) doped with rare earths, such as, for example, $Y_2SiO_5:Ce^{3+}$. In some embodiments, yttrium may be replaced by scandium or lanthanum (e.g., U.S. Pat. Nos. 6,812,500 and 6,327,074; herein incorporated by reference). Numerous materials that may be used to upconvert energy have been described (e.g., U.S. Pat. Nos. 5,956,172; 5,943,160; 7,235,189; 7,215,687; herein incorporated by reference).

At embodiment 1510, module 1420 may include one or more photolyzable nitric oxide donors that are coupled to one or more polymeric materials. In some embodiments, one or more photolyzable nitric oxide donors 108 may include one or more photolyzable nitric oxide donors 108 that are coupled to one or more polymeric materials. For example, in some embodiments, one or more polymer matrices may be impregnated with one or more photolyzable nitric oxide donors 108 (e.g., U.S. Pat. No. 5,994,444). In some embodiments, one or more photolyzable nitric oxide donors 108 may be bound to a polymer. Methods that can be used to couple nitric oxide donors to a polymeric matrix have been reported (e.g., U.S. Pat. No. 5,405,919). In some embodiments, one or more photolyzable nitric oxide donors 108 may be coupled to polymeric materials used to produce condoms. Accordingly, in some embodiments, one or more photolyzable nitric oxide donors 108 may be coupled to a condom.

Figure 16:
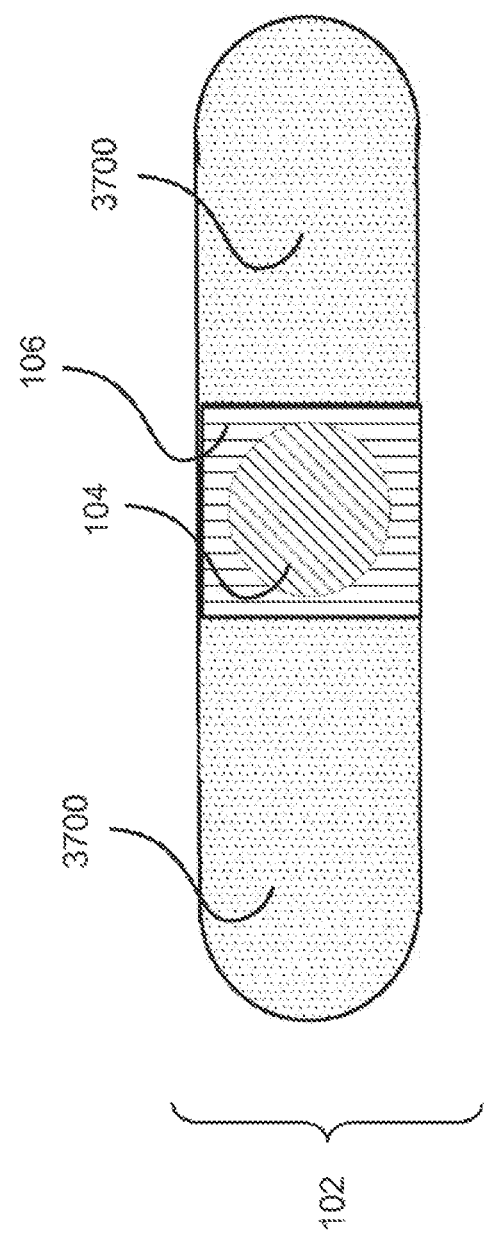
FIG. 16 illustrates embodiment of dressing 102 within system 100.

FIG. 16 illustrates an embodiment of dressing 102. In FIG. 16, an embodiment of dressing 102 is configured as a bandage. A backing sheet 106 that is light transmissive is shown operably associated with one or more photolyzable nitric oxide donors 104. The backing sheet 106 that is light transmissive and the one or more photolyzable nitric oxide donors 104 are shown operably associated with a second backing sheet 3700. In some embodiments, the second backing sheet 3700 may be transmissive to light. In some embodiments, the second backing sheet 3700 may be non-transmissive to light. In some embodiments, the second backing sheet 3700 may include one or more adhesives. In some embodiments, the second backing sheet 3700 may be porous.

FIG. 17A illustrates a side-view of an embodiment of dressing 102 as illustrated in FIG. 16. A backing sheet 106 that is transmissive to light is shown operably associated with one or more photolyzable nitric oxide donors 104, The backing sheet 106 that is transmissive to light is shown operably associated with second backing sheet 3700 that includes one or more adhesives 3710. In some embodiments, the second backing sheet 3700 may be transmissive to light. In some embodiments, the second backing sheet 3700 may be non-transmissive to light.

FIG. 17B illustrates a side-view of an embodiment of dressing 102 as illustrated in FIG. 16. A backing sheet 106 that is transmissive to light is shown operably associated with one or more photolyzable nitric oxide donors 104. The backing sheet 106 that is transmissive to light is shown operably associated with second backing sheet 3700 that includes one or more adhesives 3810. A closed space 3820 is shown adjacent to the one or more photolyzable nitric oxide donors 104. In some embodiments, the second backing sheet 3700 may be transmissive to light. In some embodiments, the second backing sheet 3700 may be non-transmissive to light.

FIG. 17C illustrates a side-view of an embodiment of dressing 102 as illustrated in FIG. 16. A backing sheet 106 that is transmissive to light is shown operably associated with one or more photolyzable nitric oxide donors 104. The backing sheet 106 that is transmissive to light is shown operably associated with second backing sheet 3700. In some embodiments, the second backing sheet 3700 may be transmissive to light. In some embodiments, the second backing sheet 3700 may be non-transmissive to light. A nitric oxide permeable layer 108 is shown operably associated with the backing sheet 3700 and one or more adhesives 3810. A closed space 3820 is shown proximate to the nitric oxide permeable layer 108.

Figure 18:
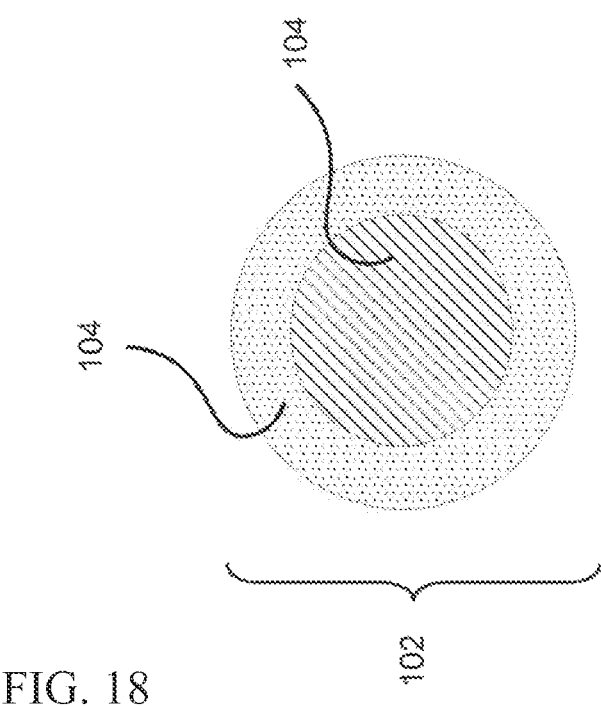
FIG. 18 illustrates embodiment of dressing 102 within system 100.

FIG. 18 illustrates an embodiment of dressing 102. In FIG. 18, an embodiment of dressing 102 is configured as a patch. A backing sheet 106 is shown operably associated with one or more photolyzable nitric oxide donors 104. In some embodiments, the backing sheet 106 may include one or more adhesives. In some embodiments, the backing sheet 106 may be porous.

FIG. 19A illustrates a side-view of an embodiment of dressing 102 as illustrated in FIG. 18. Backing sheet 106 that is transmissive to light is shown operably associated with one or more photolyzable nitric oxide donors 104. Backing sheet 106 that is transmissive to light is shown operably associated with backing sheet 4000 that includes one or more adhesives 4010. In some embodiments, the second backing sheet 4000 may be transmissive to light. In some embodiments, the second backing sheet 4000 may be non-transmissive to light.

FIG. 19B illustrates a side-view of an embodiment of dressing 102 as illustrated in FIG. 18. Backing sheet 106 that is transmissive to light is shown operably associated with one or more photolyzable nitric oxide donors 104. Backing sheet 106 that is transmissive to light is shown operably associated with backing sheet 4000 that includes one or more adhesives 4010. In some embodiments, backing sheet 4000 may be transmissive to light. In some embodiments, backing sheet 4000 may be non-transmissive to light. A closed space 4020 is shown adjacent to the one or more photolyzable nitric oxide donors 104.

FIG. 19C illustrates a side-view of an embodiment of dressing 102 as illustrated in FIG. 18. Backing sheet 106 that is transmissive to light is shown operably associated with one or more photolyzable nitric oxide donors 104. Backing sheet 106 that is transmissive to light is shown operably associated with backing sheet 4000. In some embodiments, backing sheet 4000 may be transmissive to light. In some embodiments, backing sheet 4000 may be non-transmissive to light. A nitric oxide permeable layer 108 is shown operably associated with backing sheet 4000 and one or more adhesives 4010. A closed space 4020 is shown adjacent to the nitric oxide permeable layer 108.

Figure 20:
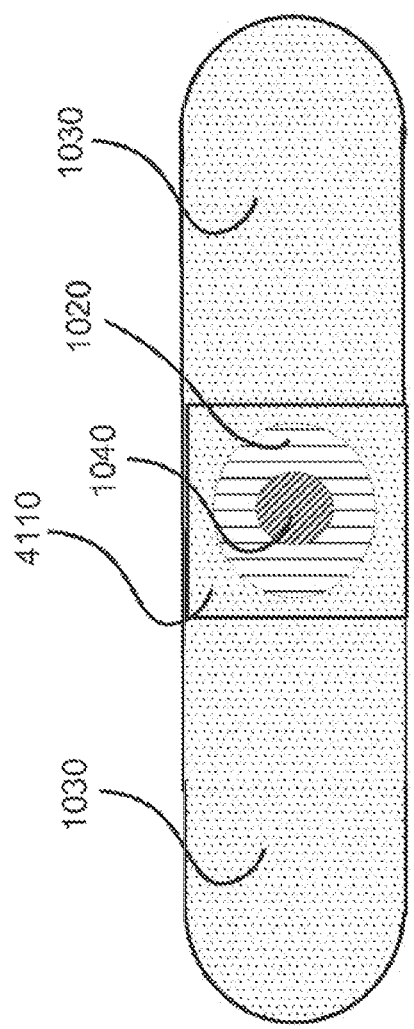
FIG. 20 illustrates embodiment of dressing 1010 within system 1000.

FIG. 20 illustrates an embodiment of dressing 1010. In FIG. 20, an embodiment of dressing 1010 is configured as a bandage. A backing sheet 1030 and a light source 1040 are shown operably associated with one or more photolyzable nitric oxide donors 1020. Adhesive 4110 is illustrated as encircling the one or more photolyzable nitric oxide donors 1020.

FIG. 21A illustrates a side-view of an embodiment of dressing 1010 as illustrated in FIG. 20. Backing sheet 1030 is shown operably associated with a light source 1040 that is operably associated with one or more photolyzable nitric oxide donors 1020. Backing sheet 1030 is shown associated with one or more adhesives 4110.

FIG. 21B illustrates a side-view of an embodiment of dressing 1010 as illustrated in FIG. 20. Backing sheet 1030 is shown operably associated with a light source 1040 that is operably associated with one or more photolyzable nitric oxide donors 1020. Backing sheet 1030 is shown associated with one or more adhesives 4110. A closed space 4220 is shown adjacent to the one or more photolyzable nitric oxide donors 1020.

FIG. 21C illustrates a side-view of an embodiment of dressing 1010 as illustrated in FIG. 20. Backing sheet 1030 is shown operably associated with a light source 1040 that is operably associated with one or more photolyzable nitric oxide donors 1020. Backing sheet 1030 is shown associated with a nitric oxide permeable layer 1050 that includes one or more adhesives 4110.

Figure 22:
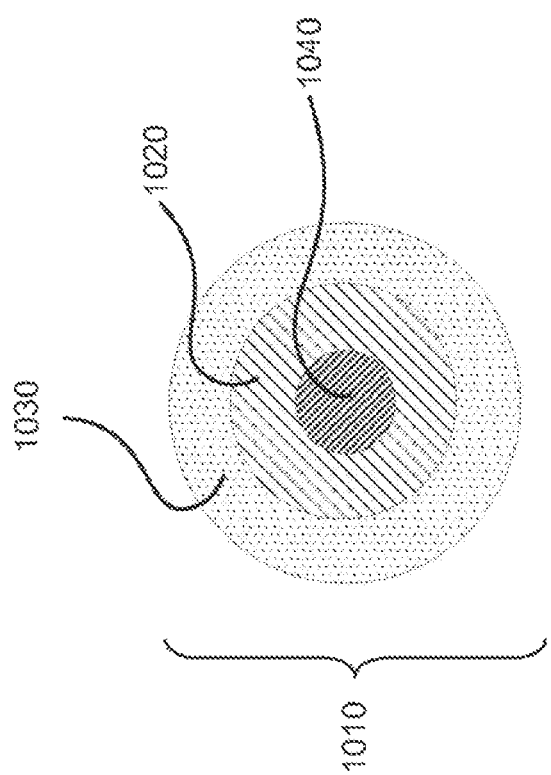
FIG. 22 illustrates embodiment of dressing 1010 within system 1000.

FIG. 22 illustrates an embodiment of dressing 1010. In FIG. 22, an embodiment of dressing 1010 is configured as a patch. A backing sheet 1030 is shown operably associated with one or more photolyzable nitric oxide donors 1020 that are operably associated with a light source 1040.

FIG. 23A illustrates a side-view of an embodiment of dressing 1010 as illustrated in FIG. 22. Backing sheet 1030 is shown operably associated with a light source 1040 that is operably associated with one or more photolyzable nitric oxide donors 1020. Backing sheet 1030 is shown associated with one or more adhesives 4110.

FIG. 23B illustrates a side-view of an embodiment of dressing 1010 as illustrated in FIG. 22. Backing sheet 1030 is shown operably associated with a light source 1040 that is operably associated with one or more photolyzable nitric oxide donors 1020. Backing sheet 1030 is shown associated with one or more adhesives 4110. A closed space 4220 is shown adjacent to the one or more photolyzable nitric oxide donors 1020.

FIG. 23C illustrates a side-view of an embodiment of dressing 1010 as illustrated in FIG. 22. Backing sheet 1030 is shown operably associated with a light source 1040 that is operably associated with one or more photolyzable nitric oxide donors 1020. Backing sheet 1030 is shown associated with a nitric oxide permeable layer 1050 that includes one or more adhesives 4110.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal-bearing medium used to actually carry out the distribution. Examples of a signal-bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, hovercraft, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a voice-over IP system, etc.), (f) a business entity (e.g., an Internet Service Provider (ISP) entity such as Comcast Cable, Quest, Southwestern Bell, etc), or (g) a wired/wireless services entity (e.g., such as Sprint, Cingular, Nextel, etc.), etc.

Although the user interface 128 is shown/described herein as a single illustrated figure that is associated with an individual 130, those skilled in the art will appreciate that a user interface 128 may be utilized by a user that is a representative of a human user, a robotic user (e.g., computational entity), and/or substantially any combination thereof (e.g., a user may be assisted by one or more robotic based systems). In addition, a user as set forth herein, although shown as a single entity may in fact be composed of two or more entities. Those skilled in the art will appreciate that, in general, the same may be said of "sender" and/or other entity-oriented terms as such terms are used herein.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

All publications, patents and patent applications cited herein are incorporated herein by reference. The foregoing specification has been described in relation to certain embodiments thereof, and many details have been set forth for purposes of illustration, however, it will be apparent to those skilled in the art that the invention is susceptible to additional embodiments and that certain of the details described herein may be varied considerably without departing from the basic principles of the invention.

What is claimed is:

1. An apparatus comprising:
   at least one light permeable substrate having a first surface configured to be positioned proximate a skin surface of a subject and having one or more photolyzable nitric oxide donors operatively coupled thereto, and a second surface opposite from the first surface; and
   at least one light emitting diode operatively coupled to the at least one light permeable substrate and operable to emit light onto at least a portion of the second surface of the at least one light permeable substrate to cause light to pass through the at least one light permeable substrate that facilitates release of nitric oxide from the one or more photolyzable nitric oxide donors coupled with the first surface proximate the skin surface of the subject.

2. The apparatus of claim 1, further comprising:
   one or more of the following types of sensors operatively coupled with the at least one control unit: nitric oxide, temperature, pressure, pulse rate, bacteria, strain, or light.

3. The apparatus of claim 1, further comprising:
   one or more electromagnetic receivers and/or transmitters operatively coupled with the at least one control unit.

4. The apparatus of claim 1, wherein the apparatus is configured as a wearable article that wraps around at least one portion of an individual.

5. The apparatus of claim 1, further comprising:
   one or more energy sources operatively coupled with the at least one control unit.

6. The apparatus of claim 1, further comprising:
   at least one electromagnetic receiver operatively coupled with the at least one control unit and operable to facilitate remote control of the at least one light emitting diode.

7. The apparatus of claim 1, further comprising:
   at least one electromagnetic receiver operatively coupled with the at least one light emitting diode and operable to receive one or more instructions associated with one or more of the following types of operations associated with the at least one light emitting diode: emission, non-emission, time, length, intensity, or wavelength.

8. The apparatus of claim 1, wherein the at least one light emitting diode is operable to emit light via one or more of the following ways: continuous, pulse, or flash.

9. The apparatus of claim 1, further comprising:
   at least one of the following types of user interfaces operatively coupled with the at least one control unit: on/off switch, push button, or key.

10. The apparatus of claim 1, wherein the at least one control unit is configured to regulate one or more of the following with respect to the at least one light emitting diode: emission, intensity, duration, frequency, wavelength, or time.

11. The apparatus of claim 1, wherein the at least one light permeable substrate comprises one or more of the following materials: metal, metal alloy, polymer, copolymer, ceramic, cloth, or fabric.

12. The apparatus of claim 1, wherein the at least one light permeable substrate comprises at least one elastomeric portion.

13. The apparatus of claim 1, wherein the at least one substrate at least partially encloses the at least one light emitting diode and/or the at least one control unit.

14. The apparatus of claim 1, further comprising:
   at least one status indicator operatively coupled with at least one of the at least one light permeable substrate, the at least one light emitting diode, or the at least one control unit, the at least one status indicator being operable to indicate a status of at least one photolyzable nitric oxide donor, the at least one light emitting diode, or the at least one control unit.

15. The apparatus of claim 1, wherein the at least one light permeable substrate includes at least one wrap portion configured to be wrapped around one or more portions of an individual,
   wherein the at least one light emitting diode is operable to emit blue light that facilitates release of nitric oxide from one or more photolyzable nitric oxide donors, wherein the apparatus further comprises at least one receiver operatively coupled with at least one control unit and that is operable to receive one or more wireless signals to facilitate remote control of one or more operations, and wherein the at least one control unit is configured to at least turn the at least one light emitting diode off after at least one predetermined amount of time has elapsed.

16. The apparatus of claim 1, wherein the one or more photolyzable nitric oxide donors are at least one of disposed on the first surface of, or integrally formed with the first surface of, the at least one light permeable substrate.

17. The apparatus of claim 1, wherein the at least one light emitting diode is operable to emit one or more of the following types of light: red, green, orange, yellow, blue, or white.

18. The apparatus of claim 1, wherein the at least one light emitting diode is operable to emit one or more of the following types of light: infrared, visible, near-ultraviolet, or ultraviolet.

19. An apparatus comprising:

at least one light permeable substrate having a first surface configured to be positioned proximate a skin surface of a subject, and a second surface opposite from the first surface;

at least one photolyzable nitric oxide donor that is operatively coupled with the first surface of the at least one light permeable substrate and that is operable to release nitric oxide in response to light; and at least one control unit operatively coupled to the at least one light permeable substrate and configured to control a permeability of the at least one light permeable substrate to cause light passing through the at least one light permeable substrate to activate release of nitric oxide from the at least one photolyzable nitric oxide donor coupled with the first surface proximate the skin surface of the subject.

20. An apparatus comprising:

at least one light permeable substrate having a first surface configured to be positioned proximate a skin surface of a subject, and a second surface opposite from the first surface;

at least one photolyzable nitric oxide donor that is operatively coupled with the first surface of the at least one light permeable substrate and that is operable to release nitric oxide in response to light; and at least one optical waveguide configured to guide a photolyzing light onto the second surface of the at least one light permeable substrate to cause light passing through the at least one light permeable substrate to activate release of nitric oxide from the at least one photolyzable nitric oxide donor coupled with the first surface proximate the skin surface of the subject.

21. An apparatus comprising:

at least one light permeable substrate having a first surface configured to be positioned proximate a skin surface of a subject, and a second surface opposite from the first surface;

least one photolyzable nitric oxide donor that is operatively coupled with the first surface of the at least one light permeable substrate and that is operable to release nitric oxide in response to light; and one or more solar cells operatively coupled to the at least one light permeable substrate and configured to provide power to facilitate light passing through the at least one light permeable substrate to activate release of nitric oxide from the at least one photolyzable nitric oxide donor coupled with the first surface proximate the skin surface of the subject.

22. An apparatus comprising:

at least one light permeable substrate having a first surface configured to be positioned proximate a skin surface of a subject, and a second surface opposite from the first surface;

at least one photolyzable nitric oxide donor that is operatively coupled with the first surface of the at least one light permeable substrate and that is operable to release nitric oxide in response to light; and at least one status indicator operatively coupled with the at least one light permeable substrate and operable to indicate a status of at least one of the at least one photolyzable nitric oxide donor or nitric oxide released by the at least one photolyzable nitric oxide donor as light passing through the at least one light permeable substrate activates release of nitric oxide from the at least one photolyzable nitric oxide donor coupled with the first surface proximate the skin surface of the subject.

* * * * *

UNITED STATES PATENT AND TRADEMARK OFFICE
CERTIFICATE OF CORRECTION

PATENT NO. : 10,080,823 B2
APPLICATION NO. : 12/927610
DATED : September 25, 2018
INVENTOR(S) : Roderick A. Hyde et al.

Page 1 of 1

It is certified that error appears in the above-identified patent and that said Letters Patent is hereby corrected as shown below:

In the Specification

Column 1, Lines 59-60:
Please replace "filed Dec. 27, 2007, which is currently co-pending" with --filed Dec. 21, 2007, which is currently co-pending--

Signed and Sealed this
Thirtieth Day of October, 2018

Andrei Iancu
*Director of the United States Patent and Trademark Office*